(12) United States Patent
Kurrasch et al.

(10) Patent No.: US 11,013,219 B2
(45) Date of Patent: May 25, 2021

(54) METABOLISM-BASED DRUG SCREENING PLATFORM IN BIOENGINEERED ZEBRAFISH

(71) Applicant: Path Therapeutics, Inc., Calgary (CA)

(72) Inventors: Deborah M. Kurrasch, Calgary (CA); Jong Rho, Calgary (CA); Kingsley Ibhazehiebo, Calgary (CA)

(73) Assignee: Path Therapeutics, Inc., Calgary (CA)

( * ) Notice: Subject to any disclaimer, the term of this patent is extended or adjusted under 35 U.S.C. 154(b) by 0 days.

(21) Appl. No.: 15/112,136

(22) PCT Filed: Jan. 16, 2015

(86) PCT No.: PCT/IB2015/000644
§ 371 (c)(1),
(2) Date: Jul. 15, 2016

(87) PCT Pub. No.: WO2015/107431
PCT Pub. Date: Jul. 23, 2015

(65) Prior Publication Data
US 2016/0338327 A1 Nov. 24, 2016

Related U.S. Application Data

(60) Provisional application No. 61/928,988, filed on Jan. 17, 2014.

(51) Int. Cl.
| | |
|---|---|
| *G01N 33/00* | (2006.01) |
| *A01K 67/027* | (2006.01) |
| *A61K 49/00* | (2006.01) |
| *C12N 15/113* | (2010.01) |

(52) U.S. Cl.
CPC ...... *A01K 67/0278* (2013.01); *A61K 49/0008* (2013.01); *C12N 15/113* (2013.01); *A01K 2207/05* (2013.01); *A01K 2207/15* (2013.01); *A01K 2217/072* (2013.01); *A01K 2227/40* (2013.01); *A01K 2267/0318* (2013.01); *C12N 2310/3233* (2013.01)

(58) Field of Classification Search
CPC ............ A61K 49/0008; A01K 2227/40; A01K 2207/05
USPC ...................................... 800/3, 20
See application file for complete search history.

(56) References Cited

FOREIGN PATENT DOCUMENTS

WO WO-2007/075753 A2 7/2007

OTHER PUBLICATIONS

Kumar (2016, eNeuro, 3(2) pp. 1-12).*
Matsuda. Autophagy, 2015, 11:1700-1701.*
Elia (2009, Mol Psychiatry, 15:637-646).*
Arjona et al., "CNNM2 mutations cause impaired brain development and seizures in patients with hypomagnesemia", PLOS Genetics, vol. 10, Issue 4, e1004267, Apr. 2014, 17 pages.
Baraban et al., "Drug screening in Scn1a zebrafish mutant identifies clemizole as a potential Dravet Syndrome treatment", Nat. Commun, 4: 2410, Mar. 3, 2014, 20 pages.
Chakravarty et al., "Chronic unpredictable stress (CUS)—induced anxiety and related mood disorders in a zebrafish model: altered brain proteome profile implicates mitochondrial dysfunction", PLOS One, vol. 8, Issue 5, e63302, May 2013, 11 pages.
Rahn et al., "Novel vitamin k analogs suppress seizures in zebrafish and mouse models of epilepsy", Neuroscience, 259: 142-154, Feb. 14, 2014, 27 pages.
International Search Report dated Sep. 22, 2015 for International Application No. PCT/IB2015/000644, filed Jan. 16, 2015, 6 pages.
Agrawal et al. (2019), "Novel proteomic changes in brain mitochondria provide insights into mitochondrial dysfunction in mouse models of Huntington's disease", Mitochondrion S1567-7249(18):30075-30078.
Aoto et al. (2015), "Co-ordinated brain and craniofacial development depend upon Patched1/XIAP regulation of cell survival", Hum. Mol. Genet. 24(3):698-713.
Arber et al. (2017), "iPSC-derived neuronal models of PANK2-associated neurodegeneration reveal mitochondrial dysfunction contributing to early disease", PLoS One 12(9):e0184104.
Bartkova et al. (2014), "A short acidic motif in ARF guards against mitochondrial dysfunction and melanoma susceptibility" Nature Comm. 5(1):5348.
Bertaggia et al. (2014), "Haptoglobin Is Required to Prevent Oxidative Stress and Muscle Atrophy", PLoS One 9(6):e100745.
Brown et al. (2017), "WNT/β-catenin signaling regulates mitochondrial activity to alter the oncogenic potential of melanoma in a PTENdependent manner", Oncogene 36:3119-3136.
Chittaranjan et al. (2014), "Mutations in CIC and IDH1 cooperatively regulate 2-hydroxyglutarate levels and cell clonogenicity", Oncotarget 5(17):7960-7979.
Cohen et al. (1999), "Monoamine Oxidase and Mitochondrial Respiration", J. Neurochem. 73(6):2310-2315.
Corda et al. (2001), "Rapid Reactive Oxygen Species Production by Mitochondria in Endothelial Cells Exposed to Tumor Necrosis Factor-_ Is Mediated by Ceramide", Am. J. Respir. Cell Mol. Biol. 24:762-768.
De-Lima-Júnior et al. (2019), "Abnormal brown adipose tissue mitochondrial structure and function in IL10 deficiency", EBioMedicine 39:436-447.

(Continued)

Primary Examiner — Valarie E Bertoglio
(74) Attorney, Agent, or Firm — Brian E. Davy; Bozicevic, Field & Francis LLP

(57) ABSTRACT

The present application provides a novel drug screening platform designed to identify drugs that favorably modulate cellular bioenergetics in the human brain of a zebrafish which has been modified by altering a teleost gene that corresponds to a human gene associated with a brain dysfunction disorder (such as epilepsy). The drug screening platform are also useful for determining a mutation in a human gene associated with a brain dysfunction disorder that is associated with a human individual responsive to the treatment of a compound. Also provided are modified teleosts useful for the methods described herein.

9 Claims, 17 Drawing Sheets

Specification includes a Sequence Listing.

(56) References Cited

OTHER PUBLICATIONS

Devi et al. (2006), "Accumulation of Amyloid Precursor Protein in the Mitochondrial Import Channels of Human Alzheimer's Disease Brain Is Associated with Mitochondrial Dysfunction", The Journal of Neuroscience 26(35):9057-9068.
Dixit et al. (2017), "Mitochondrial dysfunction in the APP/PSEN1 mouse model of Alzheimer's disease and a novel protective role for ascorbate", Free Radic. Biol. Med. 112: 515-523.
Doccini et al. (2015), "Mitochondrial respiratory chain defects in skin fibroblasts from patients with Dravet syndrome", Neurol. Sci. 36:2151-2155.
Ennequin et al. (2017), "Neuregulin 1 improves complex 2-mediated mitochondrial respiration in skeletal muscle of healthy and diabetic mice", Sci. Rep. 7:1742, 1-9.
Fiorillo et al. (2018), "The ER-alpha mutation Y537S confers Tamoxifen-resistance via enhanced mitochondrial metabolism, glycolysis and Rho-GDI/PTEN signaling: Implicating TIGAR in somatic resistance to endocrine therapy", Aging 10(12):4000-4023.
Frezza et al. (2010), "IDH1 Mutations in Gliomas: When an Enzyme Loses Its Grip", Sci. Direct 17(1):7-9.
Frye et al. (2016), "Mitochondrial Dysfunction may explain symptom variation in Phelan-McDermid Syndrome", Sci. Rep. 6:19544, 1-12.
Grassian et al. (2014), "IDH1 Mutations Alter Citric Acid Cycle Metabolism and Increase Dependence on Oxidative Mitochondrial Metabolism", Can. Res. 74(12):3317-3331.
Gresh et al. (2005), "The SWI/SNF chromatin-remodeling complex subunit SNF5 is essential for hepatocyte differentiation", EMBO J. 24(18):3313-3324.
Haasio et al. (2002), "Effects of entacapone and tolcapone on mitochondrial membrane potential", Eur. J. Pharmacol. 453(1):21-26.
Hervouet et al. (2005), "A new role for the von Hippel-Lindau tumor suppressor protein: stimulation of mitochondrial oxidative phosphorylation complex biogenesis", Carcinogenesis 26(3):531-539.
Iguchi et al. (2018), "Costimulation of Murine Osteoblasts with Interferon-γ and Tumor Necrosis Factor-α Induces Apoptosis through Downregulation of Bcl-2 and Release of Cytochrome c from Mitochondria", Mediators Inflamm. Article ID:3979606, 1-10.
James et al. (2004), "Disrupted in Schizophrenia 1 (DISC1) is a multicompartmentalized protein that predominantly localizes to mitochondria", Mol. Cell Neurosci. 26(1):112-122.
Kamp et al. (2016), "TP53 mutation, mitochondria and cancer", Sci. Direct 38,16-22.
Kaneko et al. (2001), "Calpain-Dependent Proteolysis of Merlin Occurs by Oxidative Stress in Meningiomas", Cancer 92(10):2662-2672.
Kastl et al. (2014), "TNF-a mediates mitochondrial uncoupling and enhances ROS-dependent cell migration via NF-jB activation in liver cells", Sci. Direct 588(1):175-183.
Kinghorn et al. (2015), "Loss of PLA2G6 leads to elevated mitochondrial lipid peroxidation and mitochondrial dysfunction", Brain 138(7):1801-1816.
Kristensen et al. (2014), "A PGC-1α- and muscle fibre type-related decrease in markers of mitochondrial oxidative metabolism in skeletal muscle of humans with inherited insulin resistance", Diabetologia 57(5):1006-1015.
Kumar et al. (2016), "Altered Glycolysis and Mitochondrial Respiration in a Zebrafish Model of Dravet Syndrome1,2,3", eNeuro, 3(2), 1-12.
Kvajo et al. (2008), "Evidence implicating the candidate schizophrenia/bipolar disorder susceptibility gene G72 in mitochondrial function", Molecular Psychiatry 13, 685-696.
Lee et al. (2017), "Characterization of the zinc-induced Shank3 interactome of mouse Synaptosome", Sci. Direct 494(3-4):581-586.
Little et al. (2018), "A single cell high content assay detects mitochondrial dysfunction in iPSC-derived neurons with mutations in SNCA", Sci. Rep. 13; 8(1):9033, 1-16.
Mariappan et al. (2009), "TNF-induced mitochondrial damage: a link between mitochondrial complex I activity and left ventricular dysfunction", Free Radic. Biol. Med. 46(4):462-470.
Markham et al. (2004), "BDNF increases rat brain mitochondrial respiratory coupling at complex I, but not complex II", European J. of Neurosci. 20:1189-1196.
Masgras et al. (2017), "Absence of Neurofibromin Induces an Oncogenic Metabolic Switch via Mitochondrial ERK-Mediated Phosphorylation of the Chaperone TRAP1", Sci. Direct 18(3):659-672.
Naresh et al. (2006), "The ERBB4/HER4 Intracellular Domain 4ICD Is a BH3-Only Protein Promoting Apoptosis ofBreast Cancer Cells", Cancer Res. 66:12, 6412-6420.
Neethling et al. (2019), "Wild-type and mutant (G2019S) leucine-rich repeat kinase 2 (LRRK2) associate with subunits of the translocase of outer mitochondrial membrane (TOM) complex", Experimental Cell Research 375(2):72-79.
Nocito et al. (2007), "Basic—Liver, Pancreas, and Biliary Tract", Gastroenterology 133(2):608-618.
Ogawa et al. (2003), "Binding of the human homolog of the *Drosophila* discs large tumor suppressor protein to the mitochondrial ribosomal protein MRP-S34". Biochem. Biophys. Res. Commun. 300(3):789-792.
Otte et al. (2014), "Identification of the Mitochondrial MSRB2 as a Binding Partner of LG72", Cell Mol Neurobiol, 34, 1123-1130.
Pang et al. (2011), "Apoptotic role of TGF-β mediated by Smad4 mitochondria translocation and cytochrome c oxidase subunit II interaction", Experimental Cell Research 317(11):1608-1620.
Park et al. (2014), "Parkinson's disease-associated human ATP13A2 (PARK9) deficiency causes zinc dyshomeostasis and mitochondrial dysfunction", Hum. Mol. Genet. 23(11):2802-2815.
Park et al. (2017), "DISC1 Modulates Neuronal Stress Responses by Gate-Keeping ER-Mitochondria Ca2+ Transfer through the MAM", Cell Rep. 21(10):2748-2759.
Parrado-Fernández et al. (2018), "Reduction of PINK1 or DJ-1 impair mitochondrial motility in neurites and alter ER-mitochondria contacts", J. Cell. Mol. Med. 22(11): 5439-5449.
Roudebush et al. (1997), "Neurofibromin Colocalizes with Mitochondria in Cultured Cells", Sci. Direct 236(1):161-172.
Sacchi et al. (2011), "Evidence for the interaction of D-amino acid oxidase with pLG72 in a glial cell line", Molecular and Cellular Neuroscience, 48, 20-28.
Sarasija et al. (2018), "Presenilin mutations deregulate mitochondrial Ca2+ homeostasis and metabolic activity causing neurodegeneration in Caenorhabditis elegans", eLife 7:e33052, 1-30.
Shaltouki et al. (2015), "Mitochondrial Alterations by PARKIN in Dopaminergic Neurons Using PARK2 Patient-Specific and PARK2 Knockout Isogenic iPSC Lines", Stem Cell Reports 12; 4(5): 847-859.
Shen et al. (2015), "Novel Interactive Partners of Neuroligin 3: New Aspects for Pathogenesis of Autism", J. of Mol. Neuroscience 56(1):89-101.
Shi et al. (2018) "Angiotensin-converting enzyme 2 regulates mitochondrial function in Pancreatic b-cells", Biochem. Biophys. Res. Commun. 495(1):860-866.
Simón-Carrasco et al. (2018), "The Capicua tumor suppressor: a gatekeeper of Ras signaling in development and cancer", Cell Cycle 17(6):702-711.
Su et al. (2011), "Mitochondrial dysfunction in CA1 hippocampal neurons of the Ube3a deficient mouse model for Angelman syndrome", Neurosci Lett. 487(2),129-133.
Thomas et al. (2011), "DJ-1 acts in parallel to the PINK1/parkin pathway to control mitochondrial function and autophagy", Hum. Mol. Genet. 20(1):40-50.
Tong et al. (2007), "Life extension through neurofibromin mitochondrial regulation and antioxidant therapy for neurofibromatosis-1 in *Drosophila melanogaster*", Nat. Gen. 39:476-485.
Tyagi et al. (2017), "Loss of p16INK4A stimulates aberrant mitochondrial biogenesis through a CDK4/Rb-independent pathway", Oncotarget 8(34):55848-55862.

(56) References Cited

OTHER PUBLICATIONS

Vergara et al. (2017), "b-Catenin Knockdown Affects Mitochondrial Biogenesis and Lipid Metabolism in Breast Cancer Cells", Front Physiol. 8:544.
Visalli et al. (2015), "Mitochondrial dysfunction by pro-oxidantvanadium: Ex vivo assessment of individual susceptibility", Pharmacol. 39(1):93-101.
Wilkins et al. (2017), "Platelet cytochrome oxidase and citrate synthase activities in APOE ε4 carrier and non-carrier Alzheimer's disease patients", Redox Biol. 12:828-832.
Zhang et al. (2007), "HIF-1 Inhibits Mitochondrial Biogenesis and Cellular Respiration in VHL-Deficient Renal Cell Carcinoma by Repression of C-MYC Activity", Cancer Cell 11, 407-420.
Zhang et al. (2010), "Interleukin-6 is an important mediator for mitochondrial DNA repair after alcoholic liver injury in mice", Hepatology 52(6):2137-2147.
Zhou et al. (2011), "Novel role of KCNQ2/3 channels in regulating neuronal cell viability", Cell Death Differ. 18(3):493-505.
Zhu et al. (2006), "PTEN: A crucial mediator of mitochondria-dependent Apoptosis", Apoptosis 11(2):197-207.

\* cited by examiner

Figure 1A
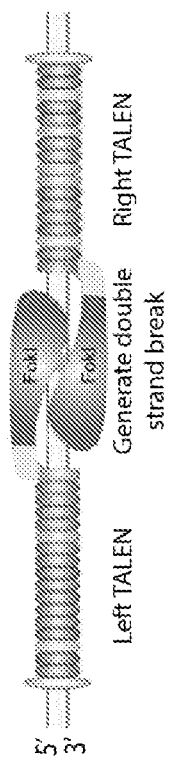
Figure 1B
WT: GCGTTATGGATGTGACATTTATGGACCGC (SEQ ID NO:9)
F1: GCGTTATGGATGTGACAT--ATıGAC ؟GC (-2, +2) (SEQ ID NO:10)
F2: GCGTTATGGA ؟G--A--TT---GAC-GC (-8, +1) (SEQ ID NO:11)
Figure 1C
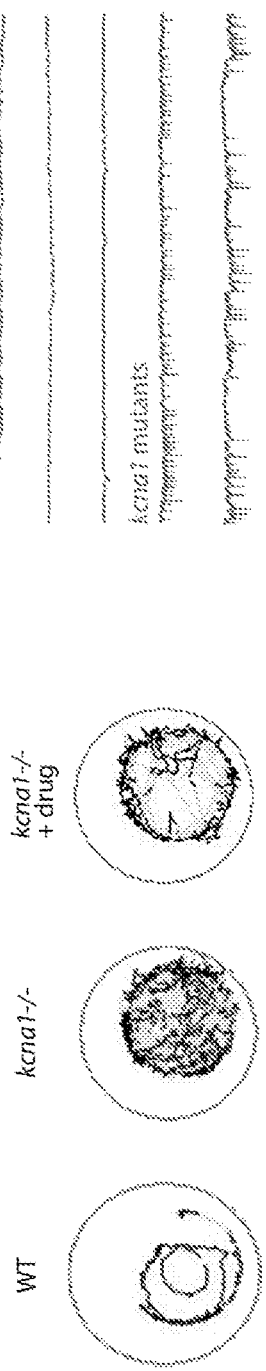
Figure 1D
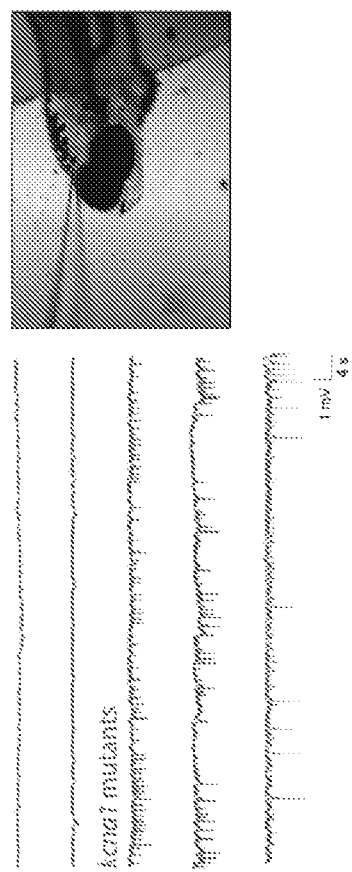

Gene Target: scn1a

Gene Target: park2

Gene Target: h3f3a

Gene Target: cdkn2b

METABOLISM-BASED DRUG SCREENING PLATFORM IN BIOENGINEERED ZEBRAFISH

CROSS-REFERENCE TO RELATED APPLICATIONS

This application is a national stage entry, filed under 35 U.S. C. § 371, of International Application No. PCT/IB2015/000644, filed on Jan. 16, 2015, which claims the benefit of and priority to U.S. Provisional Patent Application No. 61/928,988, filed Jan. 17, 2014, the entire contents of which are incorporated herein by reference in their entireties and for all purposes.

FIELD OF INVENTION

Provided herein is a novel drug screening platform designed to identify drugs that favorably modulate mitochondrial function and bioenergetics in the human brain via the use of one or more genetically altered teleost gene(s) corresponding to a human gene associated with a human disease.

BACKGROUND

Epilepsy is a common neurological condition that affects about 1-2% of the general population. For example, of the nearly 700,000 Canadian with epilepsy, about 250,000 people will not respond to drugs and will continue to have unremitting recurrent seizures and attendant life-long cognitive, behavioral, and mental health problems. Drugs remain the mainstay of treatment for epilepsy, yet despite nearly eight decades of research and advent of many newer medications, the efficacy rates have not significantly changed. Most of the drug screening process to date have been conducted in normal (i.e., non-epileptic) human brain, and in vitro functional read-out assays have almost exclusively focused on plasma membrane-bound ion channels and transporters as targets, and have largely reflected enzymes and substrates critical for cellular homeostasis.

Zebrafish are simple vertebrates that are highly amenable to teleost genetic manipulation and share >80% teleost genetic similarity with humans. Many biological pathways are shared between zebrafish and humans. In addition, like humans, zebrafish have a chambered heart, rhythmic pumping of oxygenated blood, exquisitely organized structures of the human brain, eyes, and other neural regions, and peripheral organs including the liver, pancreas, kidneys, and intestines. These features make zebrafish an attractive model for human disease.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY OF THE INVENTION

The present application in one aspect provides methods of identifying compounds that modulate mitochondrial function in human brain using a modified teleost (such as zebrafish). In some embodiments, there is provided a method of identifying a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound, b) assaying for mitochondrial function in the modified teleost, wherein a modulated mitochondrial function in the modified teleost compared to a control teleost not contacted with the compound is indicative of a compound that modulates mitochondrial function in the human brain. In some embodiments, there is provided a method of high throughput screening for a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of an plurality of modified teleosts with a different compound, b) assaying for mitochondrial function in each modified teleost, wherein a modulated mitochondrial function in the modified teleost compared to a control teleost not contacted with a compound is indicative of a compound that modulates mitochondria function in the human brain. In some embodiments, the method further comprises providing a modified teleost comprising a teleost gene that corresponds to a human gene associated with a brain dysfunction disorder, wherein said teleost gene is modified as compared to that of a wildtype teleost. In some embodiments, the teleost is zebrafish. In some embodiments, the teleost is an embryo. In some embodiments, the teleost is a larva. In some embodiments, the teleost is an adult. In some embodiments, the modified teleost comprises two or more teleost genes each corresponding to a human gene associated with a brain dysfunction disorder.

In another aspect, there are provided methods of determining whether a mutation in a human gene associated with a brain dysfunction disorder is associated with a human individual responsive to the treatment of a compound using a plurality of teleost (such as zebrafish). In some embodiments, there is provided a method of determining whether a mutation in a human gene associated with a brain dysfunction disorder is associated with a human individual responsive to the treatment of a compound, comprising: a) providing a modified teleost comprising a teleost gene that corresponds to the human gene, wherein the teleost gene is modified to mimic the modification resulting from the human gene mutation; b) contacting the modified teleost with the compound; and c) assaying for mitochondria function in the teleost, wherein a modulated mitochondrial function in the modified teleost compared to a control teleost not being contacted with the compound is indicative that a human individual having the human gene mutation would be responsive to the treatment of the compound. In some embodiments, there is provided a method of screening a plurality of human gene mutations associated with a brain dysfunction disorder to determine a human gene mutation that is associated with a human individual responsive to the treatment of a compound, comprising: a) providing a plurality of modified teleosts each comprising a teleost gene that corresponds to a human gene, wherein the teleost gene is modified to mimic the modification resulting from one of the plurality of human gene mutations; b) contacting the plurality of modified teleosts with the compound; and c) assaying for mitochondrial function in the teleosts, wherein a modulated mitochondrial function in the modified teleost compared to a control teleost not being contacted with the compound is indicative that that a human individual having the human gene mutation that corresponds to the modified teleost gene would be responsive to the treatment of the compound. In some embodiments, the teleost is zebrafish. In some embodiments, the teleost is an embryo. In some embodiments, the teleost is a larva. In some embodiments, the teleost is an adult. In some embodiments, the modified teleost comprises two or more teleost genes each corresponding to a human gene associated with a brain dysfunction disorder.

In some embodiments according to any one of the embodiments described above, the teleost is contained in a microtiter well.

In some embodiments according to any one of the embodiments described above, the contacting comprises homogeneously distributing the compound in media containing the teleost. In some embodiments, the contacting comprises injecting said compound into the teleost.

In some embodiments according to any one of the embodiments described above, the compound is selected from the group consisting of: small molecule, nucleic acid, peptide, protein, carbohydrate, and lipid. In some embodiments, the compound is a small molecule. In some embodiments, the compound is a nucleic acid. In some embodiments, the compound is a protein.

In some embodiments according to any one of the embodiments described above, the mitochondrial function is assayed by measuring one of more mitochondria outputs selected from the group consisting of: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change, transcriptional changes in mitochondrial teleost genes, and mitochondrial membrane potential. In some embodiments, the mitochondrial function is assayed by measuring at least two or more mitochondrial outputs, such as two or more of the mitochondrial outputs described herein.

In some embodiments according to any one of the embodiments above, the brain dysfunction disorder is selected from the group consisting of: episodic paroxysmal disorder, neurodegenerative disease, brain tumor, neurodevelopmental disease, and psychiatric disorder. In some embodiments, the brain dysfunction disorder is associated with neuronal hyperactivity, including, for example, episodic paroxysmal disorder (such as epilepsy, movement disorder, and migraine). In some embodiments, the brain dysfunction disorder is associated with loss of neuronal activity, including, for example, neurodegenerative disease, such as Alzheimer's disease, Parkinson's disease, or Huntington's disease.

In some embodiments according to any one of the embodiments described above, the teleost exhibits a behavioral phenotype that is indicative of human brain dysfunction.

In some embodiments according to any one of the embodiments described above, the method further comprises analyzing a behavioral phenotype of the teleost prior to analyzing for mitochondrial function in the modified teleost. In some embodiments, the behavioral phenotype is neuronal hyperactivity. In some embodiments, the behavioral phenotype is loss of neuronal function.

In some embodiments according to any one of the embodiments described above, the teleost gene in the teleost is mutated. In some embodiments, the expression product of the teleost gene of the teleost gene in the teleost is modified.

In some embodiments according to any one of the embodiments described above, wherein the method further comprises creating the modified teleost, for example by: zinc finger nuclease, TALEN, CRISPR silencing, morpholinos, or RNAi.

In some embodiments according to any one of the embodiments described above, wherein the method further comprises testing the compound in a rodent model of the disease involving a brain dysfunction disorder.

Also provided are compounds identified according to any one of the compound identification and/or screening methods described above.

In another aspect, there are provided modified teleost useful for carrying out any one of the methods described herein. In some embodiments, there is provided a modified teleost comprising a teleost gene that corresponds to a human gene associated with a brain dysfunction disorder, wherein said teleost gene is modified as compared to that of a wildtype teleost. In some embodiments, the teleost exhibits a behavioral phenotype that is indicative of human brain dysfunction.

In some embodiments, the brain dysfunction disorder is associated with neuronal hyperactivity, including, for example, epilepsy, movement disorder, and migraine. In some embodiments, the brain dysfunction disorder is epilepsy. In some embodiments, the teleost comprises a mutation in the kcna1 teleost gene. In some embodiments, the teleost comprises a mutation in the sent a teleost gene.

In some embodiments, the brain dysfunction disorder is human brain tumor.

In some embodiments, the brain dysfunction disorder is a neurodegenerative disease, including, for example, Alzheimer's disease, Parkinson's disease, and Huntington's disease.

Further provided are systems for carrying out any one or more of the methods described herein.

Each of the aspects and embodiments described herein are capable of being used together, unless excluded either explicitly or clearly from the context of the embodiment or aspect.

BRIEF DESCRIPTION OF THE FIGURES

FIG. 1 shows the creation and validation of "epileptic" zebrafish models. FIG. 1A. Fok1 nuclease linked to TALEN domains can cleave double stranded DNA and allow for genetic changes. FIG. 1B. Sequence for a TALEN-injected zebrafish embryo vs wildtype. Sequence for F3 founder line relative to WT; arrow highlights base pair change (top); sequence for F1 and F2 founder lines are shown relative to WT (bottom). FIG. 1C. Sample locomotion tracking plots are shown for WT and mutant zebrafish+/−drug. The light trace represents the zebrafish larvae and dark scribe traces indicate movement. WT zebrafish display little locomotion under normal conditions, whereas kcna1−/−zebrafish display rapid locomotion phenotype. The addition of an anticonvulsant drug decreases this hyperactive locomotion in mutant zebrafish. FIG. 1D. Picture showing extracellular field recordings from zebrafish and sample extracellular field recordings from WT (top three lines) and mutant (bottom three lines) zebrafish.

FIG. 3 provides workflow and results of behavioral analyses of hyperactive zebrafish.

FIG. 4 provides workflow and results of bioenergetic analyses in a hyperactive zebrafish.

FIG. 6 shows representative data from pilot drug screening.

FIG. 7 shows representative data from the pilot drug screen using both kcna1 and scn1a morpholino-treated zebrafish.

FIG. 8 provides data validating vorinostat, a drug uncovered during the screen.

FIG. 9 depicts data demonstrating that the results of drug screening in morpholino-treated zebrafish is similar to what is observed in mutant zebrafish.

FIG. 11 depicts the results of experiments showing that morpholino-treated zebrafish can be used to model a variety of human diseases displaying dysregulation of mitochondrial bioenergetics.

DETAILED DESCRIPTION

Figure 2:
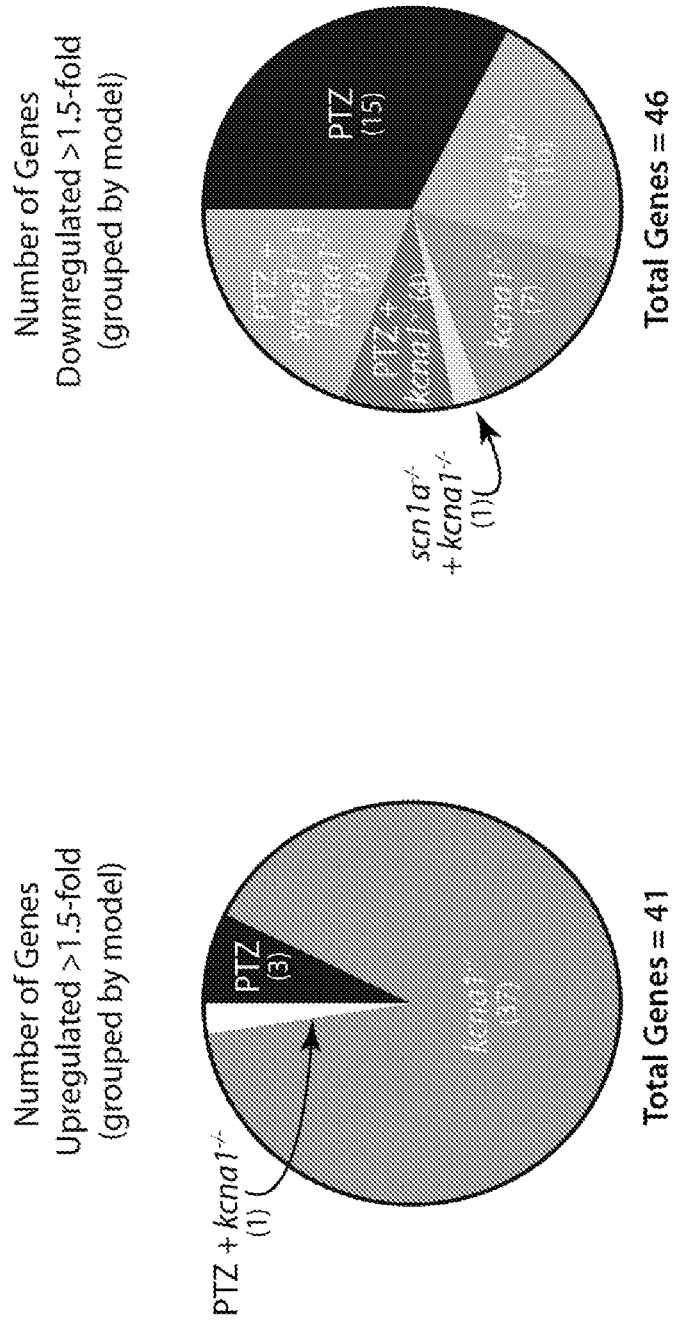
FIG. 2 depicts the number of mitochondrial genes that are differentially regulated across three models of epilepsy.

The present application provides a novel and effective drug screening platform designed to identify drugs for treating brain dysfunction disorders by using a teleost (specifically, zebrafish) model which has been modified by altering a gene contained within that corresponds to a human gene associated with a brain dysfunction disorder (such as epilepsy). The method takes advantage of the fact that dysregulations of cellular bioenergetics and mitochondrial function underlie many brain dysfunction disorders. We made modified teleost by altering a teleost gene that corresponds to a human gene associated with a brain dysfunction disorder, either through teleost gene mutation or by modifying the expression product of the teleost gene. The modified zebrafish is then used to screen and identify compounds that modulate the mitochondrial function in the human brain by analyzing the effects of the compounds on the mitochondrial function of the teleost.

Furthermore, modified teleost models can be made based on one or more human gene mutations that are known to be associated with brain dysfunction disorder, for example by modifying the teleost gene that corresponds to the one or more human gene affected by the human mutations. These modified teleost models can then be tested for their response to a compound by analyzing the effect of the compound on their mitochondrial function, and the result of such test can be used to identify which human gene mutation is associated with a human individual who would likely be responsive to the treatment with a compound.

The present application thus in one aspect provides a method of identifying a compound that modulates mitochondrial function in the brain by using a modified teleost model.

In another aspect, there is provided a method of determining whether a mutation in a human gene associated with a brain dysfunction disorder is associated with a human individual responsive to the treatment of a compound by using a modified teleost model.

In another aspect, there are provided modified teleost comprising a teleost gene that corresponds to a human gene associated with a brain dysfunction disorder, wherein the teleost gene is modified as compared to that of a wildtype teleost.

Also provided are compounds identified by following the methods described herein, as well as systems for carrying out the methods provided herein.

It is understood that aspects and embodiments of the invention described herein include "consisting of" and "consisting essentially of" aspects and embodiments.

Reference to "about" a value or parameter herein includes (and describes) variations that are directed to that value or parameter per se. For example, description referring to "about X" includes description of "X."

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The practice of the present invention will employ, unless otherwise indicated, conventional techniques of molecular biology, microbiology, cell biology, biochemistry, nucleic acid chemistry, and immunology, and zebrafish breeding and genetics which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014).

Methods of Present Invention

The present application in some embodiments provides methods of identifying compounds that modulate mitochondrial function in the human brain and/or compounds that are useful for treating brain dysfunction disorder. The modified teleost comprises a teleost gene that corresponds to a human gene associated with a brain dysfunction disorder, and the teleost gene is modified (e.g., via gene mutation and/or modification of the gene expression products) as compared to that of a wildtype teleost.

The methods for identifying compounds that modulate mitochondrial function in the human brain provided herein are highly accurate in that they have very low false positive and false negative rates. The term "false positive" as used herein, means that results (positive results) indicate that a candidate compound modulates mitochondrial function although no modulation actually occurs following exposure of the compound to the brain. Such a false positive is not preferred because compounds which do not modulate mitochondrial function are ideally excluded from potential candidates for pharmaceutical drugs. The term "false negative" as used herein means that results (negative results) indicate that a candidate compound does not modulate mitochondrial function although modulation actually occurs following exposure of the compound to the brain. Such a false negative is not preferred because such compounds which successfully modulate mitochondrial function are ideally included as potential candidates for pharmaceutical drugs. As shown in Example 6, in a double blinded study, use of the drug screening methods disclosed herein successfully identified 20 out of 21 drugs currently approved for the treatment of epilepsy by the United States Food and Drug Administration (FDA). Additionally, in a further double blinded study described in Example 6, the screening methods disclosed herein did not identify drugs that failed phase III human drug trials due to failure to reach clinical endpoints.

In some embodiments, the methods disclosed herein have a false positive and/or false negative rate of at least about any of 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0%. In other embodiments, the methods disclosed herein have a false positive and/or false negative rate of between about any of 0-1%, 0-2%, 0-3%, 0-4%, 0-5%, 0-6%, 0-7%, 0-8%, 0-9%, 0-10%, 1-3%, 1-5%, 1-7%, 1-9%, 1-11%, 2-4%, 2-6%, 2-8%, 2-10%, 3-5%, 3-7%, 3-9%, 3-11%, 4-6%, 4-8%, 4-10%, 5-7%, 5-9%, 5-11%, 6-8%, 6-10%, 7-9%, 7-11%, or 8-10%.

Brain dysfunction disorder described include, but are not limited to, episodic paroxysmal disorders, neurodegenerative diseases, brain tumors, neurodevelopmental disorders, and psychiatric disorders. These diseases and human genes associated with these diseases are described in sections below in more detail.

In some embodiments, there is provided a method of identifying a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound, b) assaying for mitochondrial function in the modified teleost, wherein a modulated mitochondrial function in the modified teleost compared to a control teleost not contacted with the compound is indicative of a compound that modulates mitochondrial function in the human brain. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial outputs: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity.

In some embodiments, there is provided a method of identifying a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound, b) assaying for mitochondrial function in the modified teleost, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

In some embodiments, there is provided a method of identifying a compound that modulates mitochondrial function in the human brain using a modified teleost, comprising: a) providing a modified teleost comprising a teleost gene that corresponds to a human gene associated with a brain dysfunction disorder, wherein said teleost gene is modified as compared to that of a wildtype teleost; b) contacting the modified teleost with a compound, and c) assaying for mitochondrial function in the modified teleost, wherein a modulated mitochondrial function in the modified teleost compared to a control teleost not contacted with the compound is indicative of a compound that modulates mitochondrial function in the human brain. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity).

In some embodiments, there is provided a method of identifying a compound that is effective in treating (or preventing, or reducing risk of, or delaying the onset of) a brain dysfunction disorder using a modified teleost, comprising: a) providing a modified teleost comprising a teleost gene that corresponds to a human gene associated with a brain dysfunction disorder, wherein said teleost gene is modified as compared to that of a wildtype teleost; b) contacting the modified teleost with a compound, and c) assaying for mitochondrial function in the modified teleost, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

"Contacting" used herein includes physically contacting the teleost with a compound or introducing (for example by injecting or via ingestion) the compound into the teleost. In some embodiments, the teleost is contained in an aqueous medium in a microtiter well, such as in a multi-well plate, e.g., a 96-well plate. In some embodiments, the compounds are administered to teleosts by electroporation, lipofection, or ingestion or by using bolistic cell loading technology in which particles coated with the biological molecule are introduced into the cell or tissue of interest as a bolus using a high-pressure gun. The teleosts may be pretreated prior to exposure to the compound, for example to facilitate the penetration and/or contacting of the compound.

In some embodiments, the compound is administered to the teleost by dissolving the compound in media containing the teleost. Alternatively, the compound may first be dissolved in the medium and the live teleost submerged in the media subsequently. In some embodiments, the compound is administered to the teleost by microinjecting the compound into the live teleost. The compounds may be brought into contact with the teleost alone, in conjunction with a variety of solvents (e.g., dimethylsulfoxide (DMSO) or the like) or carriers (including, e.g., peptide, lipid or solvent carriers), or in conjunction with other compounds.

In some embodiments, contacting comprises homogeneously distributing the compound in media containing the teleost. In some embodiments, contacting comprises injecting said compound into the teleost. Suitable vehicle for injection include, but is not limited to, E3 buffer and DMSO. In some embodiments, the teleosts are incubated at a temperature that is slightly lower than room temperature, e.g., about 24° C.). In some embodiments, the teleosts are incubated at a temperature that is lower than room temperature, optionally followed by a slightly higher temperature (e.g., about 32-34° C.). In some embodiments, the teleosts are incubated in dark/dark cycles, light/dark cycles, or light/light cycles.

Human genes associated with brain dysfunction disorder are known in the art and are described further below. For example, suitable human genes for inventions described herein can be identified, for example, by literature search. System biology approaches can be taken to cluster the teleost gene list into networks or pathways. Each teleost genetic node can then be analyzed to identify the most upstream teleost genetic component, and modified zebrafish models can be created that best represent each node.

A teleost gene that "corresponds" to a human gene associated with a brain dysfunction disorder used herein refers to a teleost gene that carries out the same or essentially the same function as the human gene associated with a brain dysfunction disorder. The determination of whether the teleost gene and the human gene may carry out the same or essentially the same function can be made, for example, based on the gene sequence, mRNA or protein expression profile, protein function, know-out phenotype, protein binding characteristics, phosphorylation characteristics, signaling pathway, or a combination thereof. Teleost genes that correspond to a human gene associated with a brain dysfunction disorder can be identified by using one or a combination of various methods known in the art, which include, but are not limited to, NCBI, UCSC genome browser, ZFIN, MGH, and Ensembl. These online tools are databases that allow sequence analysis (DNA, RNA, peptide) to uncover a wide-range of features, including comparison of sequences to determine similarity, identification of intrinsic features of the sequence, such as post translational modification sites and intron-exon boundaries, identification of differences in the sequences, such as mutation, and genetic diversity of sequences. Methods to determine functional equivalence include comparison of spatiotemporal gene expression profiles, loss-of-function and gain-of-function phenotypes, conservation of protein-protein interaction domains, and in silico analyses (e.g., reviewing literature, protein network database searches, protein prediction software tools).

In some embodiments, the teleost gene that corresponds to a human gene associated with a brain dysfunction disorder is the teleost ortholog of the human gene. Orthologs are genes that are related by vertical descent from a common ancestor and encode proteins with the equivalent function in different species. In some cases following duplication events or in large protein families, one or more paralogs (i.e., genes related by duplication within a genome) can share sequence similarity to the ancestral gene even though the paralogs may not share functional equivalence. In this case, the paralog that shares functional equivalence with the human gene is the "corresponding" human gene. Phylogenetic analysis can be used to assist on the determination on orthology relationships. In some embodiments, two or more of the methods are used to identify the ortholog of the human genes. A composite scoring system may then be used to rank the relevance of each parameters based on mitochondrial function.

In some embodiments, the modified teleost is subject to a behavioral screen prior to being assayed for mitochondrial functions, and the method may comprise analyzing a behavioral phenotype of the teleost prior to analyzing mitochondrial function in the modified teleost. Thus, for example, in some embodiments, there is provided a method of identifying a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; and c) assaying for mitochondrial function in the modified teleost, wherein a modulated mitochondrial function in the modified teleost compared to a control teleost not contacted with the compound is indicative of a compound that modulates mitochondrial function in the human brain. In some embodiments, there is provided a method of identifying a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; and c) selecting the modified teleost for mitochondrial function assay based on the modified teleost having a modulated behavioral phenotype compared to a control teleost not contacted with the compound. In some embodiments, there is provided a method of identifying a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; c) selecting the modified teleost for mitochondrial function assay based on the modified teleost having a modulated behavioral phenotype compared to a control teleost not contacted with the compound, and d) analyzing mitochondrial function in the modified teleost, wherein a modulated mitochondrial function in the modified teleost compared to a control teleost not contacted with the compound is indicative of a compound that modulates mitochondrial function in the human brain. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial outputs: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity.

In some embodiments, there is provided a method of identifying a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; and c) assaying for mitochondrial function in the modified teleost, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, there is provided a method of identifying a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; and c) selecting the modified teleost for mitochondrial function assay based on the modified teleost having a modulated behavioral phenotype compared to a control teleost not contacted with the compound. In some embodiments, there is provided a method of identifying a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting the modified teleost with a compound; b) analyzing the behavioral phenotype of the modified teleost; c) selecting the modified teleost for mitochondrial function assay based on the modified teleost having a modulated behavioral phenotype compared to a control teleost not contacted with the compound, and d) analyzing mitochondrial function in the modified teleost, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, the modified teleost comprises two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

The mitochondrial function and/or behavioral phenotypes can be assayed manually or by automatic means using devices known in the art. The behavioral phenotypes analyzed by the methods described herein depend on the nature of the brain dysfunction disorder. For example, in some embodiments when the brain dysfunction disorder involves neuronal hyperactivity (for example epilepsy), the behavioral phenotype to be analyzed can be neuronal hyperactivity. In some embodiments when the brain dysfunction disorder involves loss of neuronal function (for example a neurodegenerative disease such as Alzheimer's disease or Parkinson's disease), the behavioral phenotype to be analyzed can be loss of neuronal function. In some embodiments, the behavior assay is an assay based on electrophysiology. In some embodiments, the behavior assay is an assay based on the behavior (for example movement activity or response to stimuli) of the teleost.

In some embodiments, the behavioral phenotype can be quantified, allowing for degree of correlation or alteration of an activity be assessed. In some embodiments, the behavioral phenotype of the modified teleost has changed by at least about any of 10%, 20%, 30%, 40%, 50%, 60%, or more upon contacting the compound.

The compounds identified by the methods described herein can be further verified by conducting a dose-response analysis. Compounds that result in a dose-dependent response can be chosen and further characterized.

The compounds identified by the methods described herein can be further validated by testing the compound in a rodent model of the brain dysfunction disorder. The various methods described herein therefore in some embodiments may further comprise a step of testing the compound in a rodent model of the brain dysfunction disorder.

The compounds described herein can be any compounds, which include, but are not limited to: small molecule, nucleic acid, peptide, protein, polypeptide (for example, a non-antibody binding polypeptide), carbohydrate, and lipid. In some embodiments, the compound is a small molecule. In some embodiments, the compound is a nucleic acid, for example an inhibitory nucleic acid such as, but not limited to, a ribozyme, an antisense nucleic acid, a morpholino, a small inhibitory (si)RNA or a double stranded (ds)RNA). In some embodiments, the compound is a protein (such as an antibody).

In some aspects, the compound is a non-antibody binding polypeptide. Binding polypeptides may be synthesized using known polypeptide methods or may be prepared and isolated using recombinant molecular biological and biochemical techniques that are well known in the art. Binding polypeptides are usually at least about 5 amino acids in length, alternatively at least about 10, 15, 20, 25, 30, 35, 40, 45, 50, 60, 70, 80, 90, or 100 amino acids in length, inclusive (i.e. including all values in between these numbers) or more.

Binding polypeptides can be isolated using techniques that are well known in the art. Methods for screening polypeptide libraries for binding polypeptides that are capable of binding to a target are also well known in the art (see, e.g., U.S. Pat. Nos. 5,556,762, 5,750,373, 5,223,409, 5,403,484, 5,663,143; PCT Application Publication Nos. WO 84/03506 and WO84/03564; Clackson, T. et al., (1991) *Nature*, 352: 624; Kang, A. S. et al., (1991) *Proc. Natl. Acad. Sci. USA*, 88:8363, and Smith, G. P. (1991) *Current Opin. Biotechnol*, 2:668, the disclosures of each of which are incorporated by reference herein. Exemplary methods for generating peptide libraries as well as screening these libraries are disclosed in U.S. Pat. Nos. 5,723,286, 5,432,018, 5,580,717, and 5,723,323, the disclosures of each of which are also incorporated by reference herein.

In addition, binding polypeptides can be modified to enhance their effect (including, but not limited to, enhanced affinity, improved pharmacokinetic properties such as half-life, stability, and clearance rate, reduced toxicity, etc.). For example, such modifications can include, without limitation, glycosylation, pegylation, substitution with non-naturally occurring but functionally equivalent amino acid(s), linking groups, etc.

In another aspect, the compound is one or more inhibitory nucleic acid(s). The inhibitory nucleic acid can be, without limitation, any of an antisense oligonucleotide, a siRNA, a dsRNA, or a ribozyme.

While preferred, absolute complementarity of an inhibitory nucleic acid to a target is not required. As used herein, an inhibitory nucleic acid sequence is "complementary" to a target nucleic acid when the inhibitory nucleic acid has a sequence sufficiently complementary to be able to hybridize with the target, thereby forming a stable duplex. The ability to hybridize will depend on both the degree of complementarity and the length of the oligonucleotide. Generally, the longer the hybridizing inhibitory nucleic acid, the more base mismatches with a given target it may contain and still form a stable duplex. A person having ordinary skill in the art can ascertain a tolerable degree of mismatch by use of standard procedures to determine the melting point of the hybridized complex.

Inhibitory nucleic acids can include one or more alternate internucleoside linkages, such as, but not limited to, phosphorothioate (Mag at al., *Nucleic Acids Res.* 19:1437-1441, 1991; and U.S. Pat. No. 5,644,048), peptide nucleic acid or PNA (Egholm, *Nature*, 3685:566-568, 1993; and U.S. Pat. No. 6,656,687), phosphoramide (Beaucage, *Methods Mol. Biol.* 20:33-61, 1993), phosphorodithioate (Capaldi et al., *Nucleic Acids Res.*, 28:E40, 2000). Other oligonucleotide analogs include, but are not limited to, morpholino (Summerton, *Biochim. Biophys. Acta*, 1489:141-158, 1999), locked oligonucleotides (Wahlestedt wt al., *Proc. Natl. Acad. Sci. USA*, 97:5633-5638, 2000), peptidic nucleic adds or PNA (Nielsen et al., 1993; Hyrup and Nielsen, 1996) or 2-o-(2-methoxy)ethyl modified 5' and 3' end oligonucleotides (McKay et al., *J. Biol. Chem.*, 274:1715-1722, 1999). All of the preceding publications are hereby expressly incorporated by reference. Further, any of the inhibitory nucleic acids disclosed herein may additionally contain any combination of deoxyribo- and/or ribo-nucleotides, as well as any combination of natural and/or synthetic bases, including uracil, adenine, thymine, cytosine, guanine, inosine, xathanine hypoxathanine, isocytosine, isoguanine, etc.

The inhibitory nucleic acids discussed herein can include one or more modified base moiety such as, but not limited to, 5-fluorouracil, 5-bromouracil, 5-chlorouracil, 5-Iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, $(acp3)_w$, and/or 2,6-diaminopurine.

Inhibitory nucleic acids contemplated within the scope of the present invention can also have one or more modified sugar moiety such as, but not limited to, arabinose, 2-fluoroarabinose, xylulose, and hexose. The inhibitory nucleic acids of the present invention should be at least ten nucleotides in length, and may range from 10 to about 50 nucleotides in length, such as 15, 20, 30, 35, 40, 45, or 50 nucleotides in length, inclusive, including any values falling in between these numbers.

In some aspects, the methods disclosed herein can use a morpholino to modify the expression of a teleost gene as compared to that of a wildtype teleost. A "morpholino" or "morpholino oligonucleotide," as used herein, is an oligonucleotide composed of a 6-member morpholine ring that replaces ribose or deoxyribose rings, where (i) the structures are linked together by phosphorus-containing linkages, one to three atoms long, joining the morpholino nitrogen of one subunit to the 5' exocyclic carbon of an adjacent subunit, and (ii) purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

In other aspects, the compound is an antibody or antibody variant. The antibody may be a polyclonal antibody or a monoclonal antibody. Methods for generating and screening antibodies are routine and well known in the art. Variants of antibodies can also be made based on information known in the art, without substantially affecting the activity of an antibody. For example, antibody variants can have at least one amino acid residue in the antibody molecule replaced by a different residue. In general, sites for substitutional mutagenesis in antibodies are in the hypervariable regions. However, framework region (FR) alterations are also contemplated within the scope of the present invention.

For antibodies, one type of variant involves substituting one or more hypervariable region residues of a parent antibody (e.g. a humanized or human antibody). The resulting antibody variant(s) will have improved biological properties relative to the parent antibody from which they are generated. A convenient method for generating these types of substitutional variants is affinity maturation via the use of phage display, which is a technique that is well known to the skilled artisan. Nucleic acid molecules encoding the amino acid sequences of antibodies and/or antibody variants can be prepared by any one of several methods known in the art. These methods include, but are not limited to, isolation from a natural source (in the case of naturally occurring antibodies or antibody variants) or preparation by oligonucleotide-mediated (or site-directed) mutagenesis, PCR mutagenesis, and cassette mutagenesis of an earlier prepared variant or non-variant version of the antibody.

In some embodiments, it may be desirable to introduce one or more amino acid modifications in an Fc region of the antibodies of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine. See, also, Duncan & Winter *Nature* 322:738-40 (1988); U.S. Pat. Nos. 5,648,260; 5,624,821; and International Patent Application Publication No. WO94/29351 concerning Fc region variants, the disclosures of each of which are incorporated by reference herein.

In yet other aspects, the compound is a small molecule. Small molecules are typically organic molecules other than binding polypeptides or antibodies as described above. Small molecules can be identified and chemically synthesized using any one of several well-known methodologies (see, e.g., PCT Application Publication Nos. WO 00/00823 and WO 00/39585). Small molecules are usually less than about 2000 Daltons in size, such as less than about 1500, 750, 500, 250 or 200 Daltons in size. Small molecules that are capable of binding to a target can be identified using well known techniques (see, e.g., PCT Application Publication Nos. WO 00/00823 and WO 00/39585).

Small molecules contemplated within the scope of the instant invention include, without limitation, aldehydes, ketones, oximes, hydrazones, semicatbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule(s) contemplated for use with the present invention are components of a combinatorial chemical library. Combinatorial chemical libraries are a collection of multiple species of chemical compounds comprised of smaller subunits or monomers. Combinatorial libraries come in a variety of sizes and can include oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding a target molecule or mediating a biological activity of interest.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions.

With respect to the present invention, small molecules can be derived from any type of chemical reaction capable of being carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of dials, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclol[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

Exemplary references disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and PCT Application Publication No. WO 97/15390, the disclosures of which are incorporated by reference herein.

The methods described herein can be useful for screening compounds that modulates mitochondrial function, for example in a high throughput screening context. Thus, for example, in some embodiments, there is provided a method of high throughput screening for a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of an plurality of modified teleosts with a different compound, b) assaying for mitochondria' function in each modified teleost, wherein a modulated mitochondrial function in the modified teleost compared to a control teleost not contacted with a compound is indicative of a compound that modulates mitochondria function in the human brain. In some embodiments, the plurality of compounds comprise at least about 50 compounds, including for example at least about any of 100, 150, 200, 250, 300, 350, 400, 450, 500, 600, 700, 800, 900, 1000, 2000, 3000, 4000, 5000, or more different compounds. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity).

In some embodiments, there is provided a method of high throughput screening for a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of an plurality of modified teleosts with a different compound, b) assaying for mitochondrial function in the modified teleosts, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, the plurality of compounds comprises at least about 50 compounds, including for example at least about any of 100, 150, 200, 250, 300, 350, 400, 450, 500, 600, 700, 800, 900, 1000, 2000, 3000, 4000, 5000, or more compounds. In some embodiments, the modified teleosts comprise two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

In some embodiments, there is provided a method of high throughput screening for a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of a plurality of modified teleosts with a different compound, b) analyzing the behavioral phenotype of the modified teleosts; and c) selecting the modified teleost for mitochondrial function assay based on the modified teleost having a modulated behavioral phenotype compared to a control teleost not contacted with the compound. In some embodiments, the plurality of compounds comprises at least about 50 compounds, including for example at least about any of 100, 150, 200, 250, 300, 350, 400, 450, 500, 600, 700, 800, 900, 1000, 2000, 3000, 4000, 5000, or more compounds. In some embodiments, the modified teleosts comprise two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity).

In some embodiments, there is provided a method of high throughput screening for a compound that is effective in treating (or preventing, or reducing risk of, or delaying the onset of) a brain dysfunction disorder using a modified teleost, wherein said teleost gene is modified as compared to that of a wildtype teleost, the method comprising: a) contacting each of an plurality of modified teleosts with a different compound, b) analyzing the behavioral phenotype of the plurality of modified teleosts; and c) selecting the modified teleost for mitochondrial function assay based on the modified teleost having a modulated behavioral phenotype compared to a control teleost not contacted with the compound. In some embodiments, the plurality of compounds comprises at least about 50 compounds, including for example at least about any of 100, 150, 200, 250, 300, 350, 400, 450, 500, 600, 700, 800, 900, 1000, 2000, 3000, 4000, 5000, or more different compounds. In some embodiments, the modified teleosts comprise two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

In some embodiments, there is provided a method of high throughput screening for a compound that modulates mitochondrial function in the human brain using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of an plurality of modified teleosts with a different compound, b) analyzing the behavioral phenotype of the plurality of modified teleosts; c) selecting the modified teleost for mitochondrial function assay based on the modified teleost having a modulated behavioral phenotype compared to a control teleost not contacted with the compound, and d) assaying for mitochondrial function in the modified teleost, wherein a modulated mitochondrial function in the modified teleost compared to a control teleost not contacted with the compound is indicative of a compound that modulates mitochondrial function in the human brain. In some embodiments, the plurality of compounds comprises at least about 50 compounds, including for example at least about any of 100, 150, 200, 250, 300, 350, 400, 450, 500, 600, 700, 800, 900, 1000, 2000, 3000, 4000, 5000, or more compounds. In some embodiments, the modified teleosts comprise two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity.

In some embodiments, there is provided a method of high throughput screening for a compound that is effective in treating (or preventing, or reducing risk of, or delaying the onset of) a brain dysfunction disorder using a modified teleost, wherein the modified teleost comprises a teleost gene that corresponds to a human gene associated with a brain dysfunction disorder, wherein said teleost gene is modified as compared to that of a wildtype teleost, the method comprising: a) contacting each of an plurality of modified teleosts with a different compound, b) analyzing the behavioral phenotype of the plurality of modified teleosts; c) selecting the modified teleost for mitochondrial function assay based on the modified teleost having a modulated behavioral phenotype compared to a control teleost not contacted with the compound, and d) assaying for mitochondrial function in the modified teleost, wherein a modulated mitochondrial function in the modified teleost compared to a control teleost not contacted with the compound is indicative of a compound that is effective in treating (or preventing, or reducing risk of, or delaying the onset of) the brain dysfunction disorder. In some embodiments, the plurality of compounds comprises at least about 50 compounds, including for example at least about any of 100, 150, 200, 250, 300, 350, 400, 450, 500, 600, 700, 800, 900, 1000, 2000, 3000, 4000, 5000, or more compounds. In some embodiments, the modified teleosts comprise two or more teleost genes that are modified (e.g., via gene mutation and/or modification of the gene expression products) as compared to those of a wildtype teleost. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the compound increases (for example increases by at least about any of 10%, 20%, 30%, 40%, 50%, 60%, or more) the mitochondrial output (for example in the context when the brain dysfunction disorder involves loss of neuronal activity). In some embodiments, the compound decreases (for example decreases by at least about any of 10%, 20%, 30%, 40%, 50%, 60%, or more) the mitochondrial output (for example in the context when the brain dysfunction disorder involves neuronal hyperactivity).

In another aspect, there are provided methods of determining a mutation in a human gene associated with a brain dysfunction disorder that is associated with a human individual responsive to the treatment of a compound, or, in other words, whether a human individual having a gene mutation associated with a brain dysfunction disorder would be responsive to the treatment of a compound. The method involves testing the effect of the compound on a modified teleost comprising a teleost gene that corresponds to a human gene associated with a brain dysfunction disorder, wherein said teleost gene is modified (e.g., via gene mutation and/or modification of the gene expression products) as compared to that of a wildtype teleost. The compound would be effective in treating a human individual having the teleost gene mutation if the modified teleost contacted with the compound has a modulated mitochondrial function compared to a control teleost not contacted with the compound.

Thus, for example, in some embodiments, there is provided a method of determining whether a mutation in a human gene associated with a brain dysfunction disorder is associated with a human individual responsive to the treatment of a compound, comprising: a) providing a modified teleost comprising a teleost gene that corresponds to the human gene, wherein the teleost gene is modified to mimic the modification resulting from the human gene mutation; b) contacting the modified teleost with the compound; and c) assaying for mitochondria function in the teleost, wherein a modulated mitochondrial function in the modified teleost compared to a control teleost not being contacted with the compound is indicative that a human individual having the human gene mutation would be responsive to the treatment of the compound. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity).

In some embodiments, the method comprises screening a plurality of teleost gene mutations to determine which teleost gene mutation identifies a patient population who would be responsive to the treatment of a compound. For example, in some embodiments, there is provided a method of screening a plurality of human gene mutations associated with a brain dysfunction disorder to determine a human gene mutation that is associated with a human individual responsive to the treatment of a compound, comprising: a) providing a plurality of modified teleosts each comprising a teleost gene that corresponds to a human gene, wherein the teleost gene is modified to mimic the modification resulting from one of the plurality of human gene mutations; b) contacting the plurality of modified teleosts with the compound; and c) assaying for mitochondria function in the teleosts, wherein a modulated mitochondrial function in the modified teleost compared to a control teleost not being contacted with the compound is indicative that that a human individual having the human gene mutation that corresponds to the modified teleost gene would be responsive to the treatment of the compound. In some embodiments, the mitochondrial function is assayed by measuring any one or more of the following mitochondrial output: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, the mitochondrial function is assayed by measuring at least two or more mitochondrial outputs (such as at least two or more mitochondrial outputs described herein). In some embodiments, the modulation involves an increase (for example an increase by at least about any of 10%, 20%, 30%, 40%, 50%, 60%, or more) in the mitochondrial output (for example in the context when the brain dysfunction disorder involves loss of neuronal activity). In some embodiments, the modulation involves a decrease (for example a decrease by at least about any of 10%, 20%, 30%, 40%, 50%, 60%, or more) in the mitochondrial output (for example in the context when the brain dysfunction disorder involves neuronal hyperactivity).

The methods described herein, particularly the high throughput screening methods, can be carried out automatically. Automated methods may be performed, for example, by using commercially available automated instrumentation and software, as well as known automated observation and detection procedures. Multi-well formats can be used for high through-put and automated compound screening. Screening methods may be performed, for example, using a standard microplate well format, with at least one teleost in each well of the microplate. This format permits screening assays to be automated using standard microplate procedures and microplate readers to detect changes in mitochondrial function and/or alteration of behavioral phenotype in the teleost in the wells.

Modified Teleost

The methods described herein use modified teleost. The present application in another aspect provides modified teleost useful for any of the methods described herein. Any one of the modified teleost described in this section can be useful for the methods described herein.

As used herein, the term "teleost" means a vertebrate of or belonging to the Teleostei or Teleostomi, a group consisting of numerous fishes having bony skeletons and rayed fins. Teleosts include, for example, zebrafish (*Danio rerio*), Medaka, Giant rerio, and puffer fish. The teleost may be in any stage of its life-cycle, including embryo, larva or adult. In some embodiments, the teleost is a zebrafish embryo or larva.

In some embodiments, the teleost is zebrafish. In some embodiments, the teleost is an embryo, larva, or adult. In some embodiments, the teleost is a larva. In some embodiments, the larva has the age of about 2 to about 20 days, such as about 4 to about 14 days, for example about 8 days. In some embodiments, the larva is the zebra larve *Danio rerio*.

In some embodiments, there is provided a modified teleost comprising a teleost gene that corresponds to a human gene associated with a brain dysfunction disorder, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with a brain dysfunction disorder, wherein said teleost genes are modified (e.g., via gene mutation and/or modification of the gene expression products) as compared to a wildtype teleost. In some embodiments, the teleost gene in the teleost is modified. In some embodiments, the expression product of the teleost gene of the teleost gene in the teleost is modified.

In some embodiments, there is provided a modified teleost comprising a teleost gene that corresponds to a human gene associated with a brain dysfunction disorder involving neuronal hyperactivity, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with a brain dysfunction disorder involving neuronal hyperactivity, wherein said teleost genes are modified (e.g., via gene mutation and/or modification of the gene expression products) as compared to a wildtype teleost. In some embodiments, the teleost gene in the teleost is mutated. In some embodiments, the expression product of the teleost gene of the teleost gene in the teleost is modified.

In some embodiments, modified teleosts that model an episodic paroxysmal disorder are provided. The association of mitochondrial dysfunction with episodic paroxysmal disorder is known in the art. See, for example, Folbergrová, J., & Kunz, W. S. (2012). Mitochondrial dysfunction in epilepsy. Mitochondrion, 12(1), 35-40; Kudin, A. P., Zsurka, G., Eiger, C. E., & Kunz, W. S. (2009). Mitochondrial involvement in temporal lobe epilepsy. Experimental neurology, 218(2), 326-332; and Patel, M. (2004). Mitochondrial dysfunction and oxidative stress: cause and consequence of epileptic seizures. Free Radical Biology and Medicine, 37(12), 1951-1962. In some embodiments, there is provided a modified teleost comprising a teleost gene that corresponds to a human gene associated with an episodic paroxysmal disorder, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with episodic paroxysmal disorder, wherein said teleost genes are modified (e.g., via gene mutation and/or modification of the gene expression products) as compared to a wildtype teleost. In some embodiments, the episodic paroxysmal disorder is selected from the group consisting of epilepsy, movement disorders, and migraines.

In some embodiments, there is provided a modified teleost comprising a teleost gene that corresponds to a human gene associated with epilepsy, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with epilepsy, wherein said teleost genes are modified (e.g., via gene mutation and/or modification of the gene expression products) as compared to a wildtype teleost. In some embodiments, the teleost gene in the teleost is mutated. In some embodiments, the expression product of the teleost gene of the teleost gene in the teleost is modified.

Human genes associated with various episodic paroxysmal disorder are known in the art, and can serve as a starting point for making modified teleost models. Table 1 provides a list of human genes associated with paroxysmal disorder.

TABLE 1

Human genes associated with episodic paroxysmal disorder.

| Disease | Gene | Reference |
|---|---|---|
| Epilepsy | SCN1A | Claes, L., Ceulemans, B., Audenaert, D., Smets, K., Lofgren, A., Del-Favero, J., Ala-Mello, S., Basel-Vanagaite, L., Plecko, B., Raskin, S., Thiry, P., Wolf, N. I., Van Broeckhoven, C., De Jonghe, P. De novo SCN1A mutations are a major cause of severe myoclonic epilepsy of infancy. Hum. Mutat. 21: 615-621, 2003. |
| | KCNA1 | Browne D L, Gancher S T, Nutt J G, et al. Episodic ataxia/myokymia syndrome is associated with point mutations in the human potassium channel gene KCNA1. Nat Genet 1994; 8: 136-140. |
| | ARX | Kato, M., Saitoh, S., Kamei, A., Shiraishi, H., Ueda, Y., Akasaka, M., Tohyama, J., Akasaka, N., Hayasaka, K. A longer polyalanine expansion mutation in the ARX gene |

TABLE 1-continued

Human genes associated with episodic paroxysmal disorder.

| Disease | Gene | Reference |
|---|---|---|
| | | causes early infantile epileptic encephalopathy with suppression-burst pattern (Ohtahara syndrome). Am. J. Hum. Genet. 81: 361-366, 2007. |
| | KCNQ2 | Singh, N. A., Charlier, C., Stauffer, D., DuPont, B. R., Leach, R. J., Melis, R., Ronen, G. M., Bjerre, I., Quattlebaum, T., Murphy, J. V., McHarg, M. L., Gagnon, D., Rosales, T. O., Peiffer, A., Anderson, V. E., Leppert, M. A novel potassium channel gene, KCNQ2, is mutated in an inherited epilepsy of newborns. Nature Genet. 18: 25-29, 1998. |
| | KCNQ3 | Charlier, C., Singh, N. A., Ryan, S. G., Lewis, T. B., Reus, B. E., Leach, R. J., Leppert, M. A pore mutation in a novel KQT-like potassium channel gene in an idiopathic epilepsy family. Nature Genet. 18: 53-55, 1998. |
| | CACNA1H | Chen, Y., Lu, J., Pan, H., Zhang, Y., Wu, H., Xu, K., Liu, X., Jiang, Y., Bao, X., Yao, Z., Ding, K., Lo, W. H. Y., Qiang, B., Chan, P., Shen, Y., Wu, X. Association between genetic variation of CACNA1H and childhood absence epilepsy. Ann. Neurol. 54: 239-243, 2003. |
| | GABRB3 | Urak, L., Feucht, M., Fathi, N., Hornik, K., Fuchs, K. A GABRB3 promoter haplotype associated with childhood absence epilepsy impairs transcriptional activity. Hum. Molec. Genet. 15: 2533-2541, 2006. Note: Erratum: Hum. Molec. Genet. 15: 3272 only, 2006. |
| | DCX | Poolos, N. P., Das, S., Clark, G. D., Lardizabal, D., Noebels, J. L., Wyllie, E., Dobyns, W. B. Males with epilepsy, complete subcortical band heterotopia, and somatic mosaicism for DCX. Neurology 58: 1559-1562, 2002. |
| | SCN1B | Audenaert, D., Claes, L., Ceulemans, B., Lofgren, A., Van Broeckhoven, C., De Jonghe, P. A deletion in SCN1B is associated with febrile seizures and early-onset absence epilepsy. |
| | SCN2A | Kamiya, K., Kaneda, M., Sugawara, T., Mazaki, E., Okamura, N., Montal, M., Makita, N., Tanaka, M., Fukushima, K., Fujiwara, T., Inoue, Y., Yamakawa, K. A nonsense mutation of the sodium channel gene SCN2A in a patient with intractable epilepsy and mental decline. J. Neurosci. 24: 2690-2698, 2004. |
| | CHRNA2 | Aridon, P., Marini, C., Di Resta, C., Brilli, E., De Fusco, M., Politi, F., Parrini, E., Manfredi, I., Pisano, T., Pruna, D., Curia, G., Cianchetti, C., Pasqualetti, M., Becchetti, A., Guerrini, R., Casari, G. Increased sensitivity of the neuronal nicotinic receptor alpha-2 subunit causes familial epilepsy with nocturnal wandering and ictal fear. Am. J. Hum. Genet. 79: 342-350, 2006. |
| Movement Disorders | ATP13A2 | Di Fonzo, A., Chien, H. F., Socal, M., Giraudo, S., Tassorelli, C., Iliceto, G., Fabbrini, F., Marconi, R., Fincati, E., Abbruzzese, F., Marini, P., Squitieri, F., and 14 others. ATP13A2 missense mutations in juvenile parkinsonism and young onset Parkinson disease. Neurology 68: 1557-1562, 2007. |
| | DCTN1 | Puls, I., Jonnakuty, C., LaMonte, B. H., Holzbaur, E. L. F., Tokito, M., Mann, E., Floeter, M. K., Bidus, K., Drayna, D., Oh, S. J., Brown, R. H., Jr., Ludlow, C. L., Fischbeck, K. H. Mutant dynactin in motor neuron disease. Nature Genet. 33: 455-456, 2003. |
| | FLT | Aguilar-Martinez, P., Biron, C., Masmejean, C., Jeanjean, P., Schved, J.-F. A novel mutation in the iron responsive element of ferritin L-subunit gene as a cause for hereditary hyperferritinemia-cataract syndrome. (Letter) Blood 88: 1895-1903, 1996. |
| | PLA2G6 | Paisan-Ruiz, C., Bhatia, K. P., Li, A., Hernandez, D., Davis, M., Wood, N. W., Hardy, J., Houlden, H., Singleton, A., Schneider, S. A. Characterization of PLA2G6 as a locus for dystonia-parkinsonism. Ann. Neurol. 65: 19-23, 2009. |
| | PLANK2 | Hartig, M. B., Hortnagel, K., Garavaglia, B., Zorzi, G., Kmiec, T., Klopstock, T., Rostasy, K., Svetel, M., Kostic, V. S., Schuelke, M., Botz, E., Weindl, A., Novakovic, I., Nardocci, N., Prokisch, H., Meitinger, T. Genotypic and phenotypic spectrum of PANK2 mutations in patients with neurodegeneration with brain iron accumulation. Ann. Neurol. 59: 248-256, 2006. |
| | WDR45 | Saitsu, H., Nishimura, T., Muramatsu, K., Kodera, H., Kumada, S., Sugai, K., Kasai-Yoshida, E., Sawaura, N., Nishida, H., Hoshino, A., Ryujin, F., Yoshioka, S., and 9 |

TABLE 1-continued

Human genes associated with episodic paroxysmal disorder.

| Disease | Gene | Reference |
|---|---|---|
| | | others. De novo mutations in the autophagy gene WDR45 cause static encephalopathy of childhood with neurodegeneration in adulthood. Nature Genet. 45: 445-449, 2013. |
| Migraines | MTHFR | Lea R A, Ovcaric M, Sundholm J, MacMillan J, GriYths L R (2004). The methylenetetrahydrofolate reductase gene variant C677T in Xuences susceptibility to migraine with aura. BMC Med 2: 3 |
| | DBH | Todt U, Netzer C, Toliat M, Heinze A, Goebel I, Nürnberg P, Gobel H, Freudenberg J, Kubisch C (2009) New genetic evidence for involvement of the dopamine system in migraine with aura. Hum Genet 125: 265-279 |
| | SLC6A3 | McCallum L K, Fernandez F, Quinlan S, Macartney D P, Lea R A, GriYths L R (2007) Association study of a functional variant in intron 8 of the dopamine transporter gene and migraine susceptibility. Eur J Neurol 14: 706-707 |
| | GABRA5 | Oswell G, Kaunisto M A, Kallela M, Hämäläinen E, Anttila V, Kaprio J, Färkkilä M, Wessman M, Palotie A (2008) No association of migraine to the GABA-A receptor complex on chromosome 15. Am J Med Genet B Neuropsychiatr Genet 147B: 33-36 |
| | HTR2C | Johnson M P, Lea R A, Curtain R P, MacMillan J C, GriYths L R (2003). An investigation of the 5-HT2C receptor gene as a migraine candidate gene. Am J Med Genet B Neuropsychiatr Genet 117B: 86-89 |
| | ESR1 | Colson N J, Lea R A, Quinlan S, MacMillan J, GriYths L R (2004) The estrogen receptor 1 G594A polymorphism is associated with migraine susceptibility in two independent case/control groups. Neurogenetics 5: 129-133 |
| | TNFA | Rainero I, Grimaldi L M, Salani G, Valfrè W, Rivoiro C, Savi L, Pinessi L (2004) Association between the tumor necrosis factor-alpha-308 G/A gene polymorphism and migraine. Neurology 62: 141-143 |
| | INSR | McCarthy L C, Hosford D A, Riley J H, Bird M I, White N J, Hewett D R, Peroutka S J, GriYths L R, Boyd P R, Lea R A, Bhatti S M, Hosking L K, Hood C M, Jones K W, Handley A R, Rallan R, Lewis K F, Yeo Al, Williams P M, Priest R C, Khan P, Donnelly C, Lumsden SM, O'Sullivan J, See CG, Smart DH, Shaw-Hawkins S, Patel J, Langrish T C, Feniuk W, Knowles R G, Thomas M, Libri V, Montgomery D S, Manasco P K, Xu C F, Dykes C, Humphrey P P, Roses A D, Purvis I J (2001) Single-nucleotide polymorphism alleles in the insulin receptor gene are associated with typical migraine. Genomics 78: 135-149 |
| | ACE | Tronvik E, Stovner U, Bovim G, White L R, Gladwin A I, Owen K, Schrader H (2008) Angiotensin-converting enzyme gene insertion/deletion polymorphism in migraine patients. BMC Neurol 8: 4 |

In some embodiments, there is provided a modified teleost comprising a teleost gene that corresponds to a human gene associated with a brain dysfunction disorder involving loss of neuronal function, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with a brain dysfunction disorder involving loss of neuronal function, wherein said teleost genes are modified (e.g., via gene mutation and/or modification of the gene expression products) as compared to a wildtype teleost. In some embodiments, the brain dysfunction disorder involving loss of neuronal function is a neurodegenerative disease. In some embodiments, the neurodegenerative disease is selected from the group consisting of: Alzheimer's disease, Parkinson's disease, and Huntington's disease.

In some embodiments, modified teleosts that model a neurodegenerative disorder, such as Alzheimer's disease, Parkinson's disease, and Huntington's disease, are provided. The association of mitochondrial dysfunction with Alzheimer's disease is known in the art. See, for example, Cassarino, D. S. & Bennett, J. P. (1999): An evaluation of the role of mitochondria in neurodegenerative diseases: mitochondrial mutations and oxidative pathology, protective nuclear responses, and cell death in neurodeteleost generation. Human brain Research Reviews 29, 1-25; Hirai, K. et al. (2001): Mitochondrial abnormalities in Alzheimer's disease. The Journal of Neuroscience, 21(9), 3017-3023; and Yan, M. et al. (2013): Mitochondrial defects and oxidative stress in Alzheimer's disease and Parkinson disease. Free Radical Biology and Medicine 62, 90-101. The association of mitochondrial dysfunction with Parkinson's disease is known in the art. See, for example, Onyango, I. G. (2008): Mitochondrial dysfunction and oxidative stress in Parkinson's disease. Neurochemical research, 33(3), 589-597; Yan, M. et al. (2013): Mitochondrial defects and oxidative stress in Alzheimer's disease and Parkinson disease. Free Radical Biology and Medicine 62, 90-101. The association of mitochondrial dysfunction with Huntington's disease is known in the art. See, for example, Browne, S. E., & Beal, M. F. (2004): The energetics of Huntington's disease. Neurochemical research, 29(3), 531-546; Costa, V., & Scorrano, L.

(2012). Shaping the role of mitochondria in the pathoteleost genesis of Huntington's disease. The EMBO journal, 31(8), 1853-1864; Federico, A. et al. (2012). Mitochondria, oxidative stress and neurodeteleost generation. Journal of the neurological sciences, 322(1), 254-262.

Human genes associated with various neurodegenerative diseases are known in the art, and can serve as a starting point for making modified teleost models. Table 2 provides a list of human genes associated with neurodegenerative diseases.

TABLE 2

Human genes associated with neurodegenerative disease

| Disease | Gene | Reference |
|---|---|---|
| Alzheimer's Disease | APP | Goate A, Chartier-Harlin M C, Mullan M, et al. Segregation of a missense mutation in the amyloid precursor protein gene with familial Alzheimer's disease. Nature 1991; 349: 704e706. |
| | PSEN1 | Cruts M, Hendriks L, Van Broeckhoven C. The presenilin genes: a new gene family involved in Alzheimer disease pathology. Hum Mol Genet 1996; 5: 1449e1455. |
| | PSEN2 | Levy-Lahad E, Wijsman E M, Nemens E, et al. A familial Alzheimer's disease locus on chromosome 1. Science 1995; 269: 970e973. |
| | APOE | Kim, J., Basak, J. M., and Holtzman, D. M. (2009a). The role of apolipoprotein E in Alzheimer's disease. Neuron 63, 287-303. |
| Parkinson's Disease | LKK2 | Zimprich, A. et al. Mutations in LRRK2 cause autosomal-dominant parkinsonism with pleomorphic pathology. Neuron 44, 601-607 (2004). |
| | SNCA | Lotharius, J. & Brundin, P. Pathogenesis of Parkinson's disease: dopamine, vesicles and α-synuclein. Nature Rev. Neurosci. 3, 932-942 (2002). |
| | PARK2 | Kitada, T. et al. Mutations in the parkin gene cause autosomal recessive juvenile parkinsonism. Nature 392, 605-608 (1998). |
| | PINK1 | Valente, E. M. et al. Hereditary early-onset Parkinson's disease caused by mutations in PINK1. Science 304, 1158-1160 (2004). |
| | DJ1 | Lockhart, P. J. et al. DJ-1 mutations are a rare cause of recessively inherited early onset parkinsonism mediated by loss of protein function. J. Med. Genet. 41, e22 (2004). |
| Huntington's Disease | HTT | The Huntington's Disease Collaborative Research Group (1993) A novel gene containing a trinucleotide repeat that is expanded and unstable on Huntington's disease chromosomes. Cell 72, 971-983 |

In some embodiments, modified teleosts that model a human brain tumor are provided. The association of mitochondrial dysfunction with human brain tumor is known in the art. See, for example, Arismendi-Morillo, G. J., & Castellano-Ramirez, A. V. (2008): Ultrastructural mitochondrial pathology in human astrocytic tumors: potentials implications pro-therapeutics strategies. Journal of electron microscopy, 57(1), 33-39; Kiebish, M. A., Han, X., Cheng, H., & Seyfried, T. N. (2009). In vitro growth environment produces lipidomic and electron transport chain abnormalities in mitochondria from non-tumorigenic astrocytes and human brain tumours. Asn Neuro, 1(3), 125-138; Liang, B. C., & Grootveld, M. (2011): The importance of mitochondria in the tumourigenic phenotype: Gliomas as the paradigm (Review). International journal of molecular medicine, 27(2), 159; Oliva, C. R. et al. (2011): Acquisition of chemoresistance in gliomas is associated with increased mitochondrial coupling and decreased ROS production. PloS one, 6(9), e24665; Ordys, B. B. et al. (2010): The role of mitochondria in glioma pathophysiology. Molecular neurobiology, 42(1), 64-75.

In some embodiments, there is provided a modified teleost comprising a teleost gene that corresponds to a human gene associated with human brain tumor, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with human brain tumor, wherein said teleost genes are modified (e.g., via gene mutation and/or modification of the gene expression products) as compared to a wildtype teleost. In some embodiments, the human brain tumor is selected from the group consisting of Gliomas (Astrocytoma, Oligodendroglioma, Ependymoma, Unspecified gliomas, Mengiomas, Haemangioblastomas, Acoustic Neuromas, Craiopharyngiomas, Lymphomas, and Germ Cell Tumors.

Human genes associated with various brain tumors are known in the art, and can serve as a starting point for making modified teleost models. Table 3 provides a list of human genes associated with brain tumors.

TABLE 3

Human genes associated with brain tumors

| Disease | Gene | Reference |
|---|---|---|
| Astrocytoma | NF1 | Kluwe, L. et al. Loss of NF1 alleles distinguish sporadic from NF1-associated pilocytic astrocytomas. J. Neuropathol. Exp. Neurol. 60, 917-920 (2001). |
| | TP53 | Reifenberger, G. & Collins, V. P. Pathology and molecular genetics of astrocytic gliomas. J. Mol. Med. (Berl.) 82, 656-670 (2004). |
| | ATRX | Jiao, Y. et al. Frequent ATRX, CIC, and FUBP1 mutations refine the classification of malignant gliomas. Oncotarget 3, 709-722 (2012). |
| | IDH1 | Sturm, D. et al. Hotspot mutations in H3F3A and IDH1 define distinct epigenetic and biological subgroups of glioblastoma. Cancer Cell 22, 425-437 (2012). |
| Oligodendroglioma | IDH | Yan H, Parsons D W, Jin G, et al. IDH1 and IDH2 mutations in gliomas. N Engl J Med 2009; 360: 765-773. |
| | CIC | Bettegowda C, Agrawal N, Jiao Y, et al. Mutations in CIC and FUBP1 contribute to human oligodendroglioma. Science 2011; 333: 1453-1455. |
| | FUBP1 | Sahm F, Koelsche C, Meyer J, et al. CIC and FUBP1 mutations in oligodendrogliomas, oligoastrocytomas and astrocytomas. Acta Neuropathol 2012; 123: 853-860. |
| | CDKN2B | (Feng J, Kim S T, Liu W, Kim J W, Zhang Z, Zhu Y, Berens M, Sun J, Xu J. An integrated analysis of germline and somatic, genetic, and spigenetic alterations at 9p21.3 in glioblastoma. Cancer, 2012, Jan 1: 118(1): 232-40.) |
| | H3F3A | (Sturm D, et al. Hotspot mutations in H3F3A and IDH1 define distinct epigenetic and biological subgrounds of glioblastoma. Cancer Cell, 2012 Oct 16: 22(4): 425-37.) |
| Ependymoma | HOXB5, PLA265, ITIH2 | Korshunov, A et al. Gene expression patterns in ependymomas correlate with tumor location, grade, and patient age. Am. J. Pathol. 163, 1721-1727 (2003). |
| | NF2 | Singh, P. K., Gutmann, D. H., Fuller, C. E., Newsham, I. F. & Perry, A. Differential involvement of protein 4.1 family members DAL 1 and NF2 in intracranial and intraspinal ependymomas. Mod. Pathol. 15, 526-531 (2002). |
| | CDKN2A | Korshunov, A et al. Molecular staging of intracranial ependymoma in children and adults. J. Clin. Oncol. 28, 3182-3190 (2010). |
| Mengiomas | DAL1 | Gutmann D H, Donahoe J, Perry A, Lemke N, Gorse K, Kittiniyom K, Rempel S A, Gutierrez J A, Newsham IF: Loss of DAL-1, a protein 4.1-related tumor suppressor, is an important early event in the pathogenesis of meningiomas. Hum Mol Genet 9: 1495-1500, 2000. |
| | NF2 | Hartmann C, Sieberns J, Gehlhaar C, Simon M, Paulus W, von Deimling A: NF2 mutations in secretory and other rare variants of meningiomas. Brain Pathol 16: 15-19, 2006. |
| | PATCHED | Xie J, Johnson R L, Zhang X, Bare J W, Waldman F M, Cogen P H, Menon A G, Warren R S, Chen L C, Scott M P, Epstein E H Jr: Mutations of the PATCHED gene in several types of sporadic extracutaneous tumors. Cancer Res 57: 2369-2372, 1997. |
| | PTEN | Peters N, Wellenreuther R, Rollbrocker B, Hayashi Y, Meyer-Puttlitz B, Duerr E M, Lenartz D, Marsh D J, Schramm J, Wiestler O D, Parsons R, Eng C, von Deimling A: Analysis of the PTEN gene in human meningiomas. Neuropathol Appl Neurobiol 24: 3-8, 1998. |
| | INK4A, CDK4 | Tse J Y, Ng H K, Lo K W, Chong E Y, Lam P Y, Ng E K, Poon W S, Huang D P: Analysis of cell cycle regulators: p16 INK4A, pRb, and CDK4 in low- and high-grade meningiomas. Hum Pathol 29: 1200-1207, 1998. |
| | MADH2, MADH4, APM-1, DCC | Büschges R, Boström J, Wolter M, Blaschke B, Weber R G, Lichter P, Collins V P, Reifenberger G: Analysis of human meningiomas for aberrations of the MADH2, MADH4, APM-1 and DCC tumor suppressor genes on the long arm of chromosome 18. Int J Cancer 92: 551-554, 2001. |
| Haemangioblastomas | VHL | Glasker, S et al. The impact of molecular genetic analysis of the VHL gene in patients with |

TABLE 3-continued

Human genes associated with brain tumors

| Disease | Gene | Reference |
|---|---|---|
| | | haemangioblastomas of the central nervous system. J. Neurol. Neurosurg. Psychiatry. 67, 758-762 (1999). |
| Acoustic Neuromas/ Vestibular Schwannoma | NF2 | Irving, R. M., Moffat, D. A., Hardy, D. G., Barton, D. E., Xuereb, J. H., & Maher, E. R. (1994). Somatic NF2 gene mutations in familial and non-familial vestibular schwannoma. Human molecular genetics, 3(2), 347-350. |
| Craiopharyngiomas | CTNNB1 | Campanini, M. L., Colli, L. M., Paixao, B. M. C., Cabral, T. P. F., Amaral, F. C., Machado, H. R., . . . & de Castro, M. (2010). CTNNB1 gene mutations, pituitary transcription factors, and MicroRNA expression involvement in the pathogenesis of adamantinomatous craniopharyngiomas. Hormones and Cancer, 1(4), 187-196. |
| Lymphomas | TNF | Rothman N, Skibola C F, Wang S S, Morgan G, Lan Q, Smith MT, et al. Genetic variation in TNF and IL10 and risk of non-Hodgkin lymphoma: a report from the Inter-Lymph Consortium. Lancet Oncol 2006; 7: 27-38. |
| | 1L6 | Cordano P, Lake A, Shield L, Taylor G M, Alexander F E, Taylor PR, et al. Effect of IL-6 promoter polymorphism on incidence and outcome in Hodgkin's lymphoma. Br J Haematol 2005; 128: 493-5. |
| | 1L10 | Breen E C, Boscardin W J, Detels R, Jacobson L P, Smith M W, O'Brien S J, et al. Non-Hodgkin's B cell lymphoma in persons with acquired immunodeficiency syndrome is associated with increased serum levels of IL10, or the IL10 promoter −592 C/C genotype. Clin Immunol 2003; 109: 119-29. |
| | MSH2 | Hishida A, Matsuo K, Hamajima N, Ito H, Ogura M, Kagami Y, et al. Polymorphism in the hMSH2 gene (gIVS 12-6T-->C) and risk of non-Hodgkin lymphoma in a Japanese population. Cancer Genet Cytogenet 2003; 147: 71-4. |
| Germ Cell Tumors | CCND2 | Houldsworth, J., Reuter, V., Bosl, G. J., and Chaganti, R. S. K. Aberrant expression of cyclin D2 is an early event in human male germ cell tumorigenesis. Cell Growth Differ., 8: 293-299, 1997 |
| | RASK2, WKS, and JAW1 | Mostert, M. C., Verkerk, A. J., van de Pol, M., Heighway, J., Marynen, P., Rosenberg, C., van Kessel, A. G., van Echten, J., de Jong, B., Oosterhuis, J. W., and Looijenga, L. H. Identification of the critical region of 12p over-representation in testicular germ cell tumors of adolescents and adults. Oncogene, 16: 2617-2627, 1998. |
| Atypical Teratoid/Rhabdoid tumors | SNF5 | Biegel J A, Tan L, Zhang F, Wainwright L, Russo P, and Rorke LB. Alterations of the hSNF5/INI1 Gene in Central Nervous System Atypical Teratoid/Rhabdoid Tumors and Renal and Extrarenal Rhabdoid Tumors. Clinical Cancer Research, 2002: 8, 3461-3464) |

In some embodiments, modified teleosts that model a neurodevelopmental disorder, such as ADHD, Autism Spectrum Disorder, Learning Disorder, and Developmental Coordination Disorder are provided. The association of mitochondrial dysfunction with ADHD is known in the art. See, for example, Marazziti, D. et al (2012): Psychiatric disorder and mitochondrial dysfunctions. Eur Rev Med Pharmacol Sci, 16(2), 270-275. The association of mitochondrial dysfunction with autism is known in the art. See, for example, Ghanizadeh, A et al. (2013). Targeting the mitochondrial electron transport chain in autism, a systematic review and synthesis of a novel therapeutic approach. Mitochondrian, 13(5), 515-519; Giulivi, C et al. (2010): Mitochondrial dysfunction in Autism. Journal of American Medical Association, 304(21), 2389-2396. doi:10.1001/jama.2010.1706; Lombard, J. (1998). Autism: A mitochondrial disorder? Medical Hypothesis, 50, 497-500; Oliveira, G et al. (2005). Mitochondrial dysfunction in autism spectrum disorders: a population-based study. Developmental Medicine & Child Neurology, 47, 185-189; Smith, M. et al. (2012). Mitochondrial and ion channel teleost gene alterations in autism. Biochimica et Biophysica Acta-Bioenergetics, 1817(10), 1796-1802.

In some embodiments, there is provided a modified teleost comprising a teleost gene that corresponds to a human gene associated with a neurodevelopmental disorder, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with a neurodevelopmental disorder, wherein said teleost genes are modified (e.g., via gene mutation and/or modification of the gene expression products) as compared to a wildtype teleost. In some embodiments, the neurodevelopmental disorder is selected from the group consisting of autism, ADHD, learning disorder, and developmental coordination disorder.

Human genes associated with various neurodevelopmental disorders are known in the art, and can serve as a starting point for making modified teleost models. Table 4 provides a list of human genes associated with neurodevelopmental disorders.

TABLE 4

Human genes associated with neurodevelopmental disorder

| Disease | Gene | Reference |
|---|---|---|
| ADHD | CNTNAP2 | Elia J, Gai X, Xie H M, Perin J C, Geiger E, Glessner JT, D'Arcy M, R, Frackelton E, Kim C et al.: Rare structural variants found in attention-deficit hyperactivity disorder are preferentially associated with neurodevelopmental genes. Mol Psychiatry 2009. |
| Autism Spectrum Disorder | APBA2 | Kevin J Mitchell, The genetics of neurodevelopmental disease, Current Opinion in Neurobiology, Volume 21, Issue 1, February 2011, Pages 197-203. |
| | ASTN2 | Glessner J T, et al.: Autism genomewide copy number variation reveals ubiquitin and neuronal genes. Nature 2009, 459: 569-573. |
| | CNTN3 | Morrow E M, Yoo S Y, Flavell S W, Kim T K, Lin Y, Hill R S, Mukaddes N M, Balkhy S, Gascon G, Hashmi A et al.: Identifying autism loci and genes by tracing recent shared ancestry. Science 2008, 321: 218-223. |
| | CNTN4 | Glessner J T, Wang K, Cai G, Korvatska 0, Kim C E, Wood S, Zhang H, Estes A, Brune C W, Bradfield J P et al.: Autism genomewide copy number variation reveals ubiquitin and neuronal genes. Nature 2009, 459: 569-573. |
| | CNTNAP2 | Bakkaloglu B, O'Roak BJ, Louvi A, Gupta A R, Abelson J F, Morgan T M, Chawarska K, Klin A, Ercan-Sencicek AG, Stillman AA et al.: Molecular cytogenetic analysis and resequencing of contactin associated protein-like 2 in autism spectrum disorders. Am J Hum Genet 2008, 82: 165-173. |
| | CNTNAP5 | Pagnamenta A T, Bacchelli E, de Jonge M V, Mirza G, Scerri T S, Minopoli F, Chiocchetti A, Ludwig K U, Hoffmann P, Paracchini S et al.: Characterization of a family with rare deletions in CNTNAP5 and DOCK4 suggests novel risk loci for autism and dyslexia. Biol Psychiatry 2010, 68: 320-328. |
| | NLGN3, NLGN4 | Jamain S, Quach H, Betancur C, Rastam M, Colineaux C, Gillberg IC, Soderstrom H, Giros B, Leboyer M, Gillberg C et al.: Mutations of the X-linked genes encoding neuroligins NLGN3 and NLGN4 are associated with autism. Nat Genet 2003, 34: 27-29. |
| | UBE3A | Bucan M, Abrahams B S, Wang K, Glessner J T, Herman El, Sonnenblick L I, Alvarez Retuerto A I, Imielinski M, Hadley D, Bradfield JP et al.: Genome-wide analyses of exonic copy number variants in a family-based study point to novel autism susceptibility genes. PLoS Genet 2009, 5: e1000536. |
| | SHANK3 | Moessner R, Marshall CR, Sutcliffe J S, Skaug J, Pinto D, Vincent J, Zwaigenbaum L, Fernandez B, Roberts W, Szatmari P, Scherer S W. Contribution of SHANK3 mutations to austism spectrum disorder. American Journal of Human Genetics, 2007 Dec. 8, 81: 1289-97 |

In some embodiments, modified teleosts that model a psychiatric disorder, such as bipolar disorder, depression, schizophrenia, and anxiety disorder are provided. The association of mitochondrial dysfunction with bipolar disorder is known in the art. See, for example, Berk, M. et al. (2011). Pathways underlying neuroprogression in bipolar disorder: focus on inflammation, oxidative stress and neurotrophic factors. Neuroscience & biobehavioral reviews, 35(3), 804-817; Kato, T. (2007). Mitochondrial Dysfunction as the Molecular Basis of Bipolar Disorder. CNS drugs, 21(1), 1-11; Konradi, C et al. (2004). Molecular evidence for mitochondrial dysfunction in bipolar disorder. Archives of teleost general psychiatry, 61(3), 300; Stork, C., & Renshaw, P. F. (2005). Mitochondrial dysfunction in bipolar disorder: evidence from magnetic resonance spectroscopy research. Molecular psychiatry, 10(10), 900-919. The association of mitochondrial dysfunction with depression is known in the art. See, for example, Gardner, A., & Boles, R. G. (2011). Beyond the serotonin hypothesis: mitochondria, inflammation and neurodeteleost generation in major depression and affective spectrum disorders. Progress in Neuro-Psychopharmacology and Biological Psychiatry, 35(3), 730-743; Gardner, A et al. (2003): Alterations of mitochondrial function and correlations with personality traits in selected major depressive disorder patients. Journal of affective disorders, 76(1), 55-68; Rezin, G. T. et al. (2008) Inhibition of mitochondrial respiratory chain in human brain of rats subjected to an experimental model of depression. Neurochemistry international, 53(6), 395-400; Manji, H. et al. (2012). Impaired mitochondrial function in psychiatric disorders. Nature Reviews Neuroscience, 13(5), 293-307. The association of mitochondrial dysfunction with schizophrenia is known in the art. See, for example, Ben-Shachar, D. (2002). Mitochondrial dysfunction in schizophrenia: a possible linkage to dopamine. Journal of neurochemistry, 83(6), 1241-

1251; Park, C., & Park, S. K. (2012). Molecular links between mitochondrial dysfunctions and schizophrenia. Molecules and cells, 33(2), 105-110; Prabakaran, S et al. (2004). Mitochondrial dysfunction in schizophrenia: evidence for compromised human brain metabolism and oxidative stress. Molecular psychiatry, 9(7), 684-697. The association of mitochondrial dysfunction with psychiatric disorders is known in the art. See, for example, Shao, L. et al. (2008). Mitochondrial involvement in psychiatric disorders. Annals of medicine, 40(4), 281-295; Rezin, G. T et al. (2009). Mitochondrial dysfunction and psychiatric disorders. Neurochemical research, 34(6), 1021-1029.

In some embodiments, there is provided a modified teleost comprising a teleost gene that corresponds to a human gene associated with a psychiatric disorder, wherein said teleost gene is modified (e.g., via gene mutation and/or modification of the gene expression product) as compared to a wildtype teleost. In some embodiments, there is provided a modified teleost comprising two or more (such as three, four, five, six, seven, eight, nine, ten, or more) teleost genes that correspond to human genes associated with a psychiatric disorder, wherein said teleost genes are modified (e.g., via gene mutation and/or modification of the gene expression products) as compared to a wildtype teleost. In some embodiments, the psychiatric disorder is selected from the group consisting of bipolar disorder, depression, schizophrenia, and anxiety disorder.

Human genes associated with various psychiatric disorders are known in the art, and can serve as a starting point for making modified teleost models. Table 5 provides a list of human genes associated with psychiatric disorders.

TABLE 5

Human genes associated with psychiatric disorder

| Disease | Gene | Reference |
|---|---|---|
| Major Depression | SLC6A4 | Murphy Jr, G. M., Hollander, S. B., Rodrigues, H. E., Kremer, C., & Schatzberg, A. F. (2004). Effects of the serotonin transporter gene promoter polymorphism on mirtazapine and paroxetine efficacy and adverse events in geriatric major depression. Archives of general psychiatry, 61(11), 1163. |
| | BDNF | Vaidya, V. A., & Duman, R. S. (2001). Depression - emerging insights from neurobiology. British Medical Bulletin, 57(1), 61-79. |
| | HP | Meltzer, H. Y., Suy, E., & Bosmans, E. (1994). Haptoglobin phenotypes and gene frequencies in unipolar major depression. Am J Psychiatry, 151(1), 113. |
| | SERT | Ogilvie, A. D., Battersby, S., Fink, G., Harmar, A. J., Goodwin, G. M., Bubb, V. J., & Dale Smith, C. A. (1996). Polymorphism in serotonin transporter gene associated with susceptibility to major depression. The Lancet, 347(9003), 731-733. |
| | DRD4 | Manki, H., Kanba, S., Muramatsu, T., Higuchi, S., Suzuki, E., Matsushita, S., . . . & Asai, M. (1996). Dopamine D2, D3 and D4 receptor and transporter gene polymorphisms and mood disorders. Journal of affective disorders, 40(1), 7-13. |
| | SLC1 | McCullumsmith, R. E., & Meador-Woodruff, J. H. (2002). Striatal excitatory amino add transporter transcript expression in schizophrenia, bipolar disorder, and major depressive disorder. Neuropsychopharmacology, 26(3), 368-375. |
| | MAOA | Ogilvie, A. D., Battersby, S., Fink, G., Harmar, A. J., Goodwin, G. M., Bubb, V. J., & Dale Smith, C. A. (1996). Polymorphism in serotonin transporter gene associated with susceptibility to major depression. The Lancet, 347(9003), 731-733. |
| | TPH1 | Cusin, C., Serretti, A., Lattuada, E., Lilli, R., Lorenzi, C., Mandelli, L., . . . & Smeraldi, E. (2001). Influence of 5-HTTLPR and TPH variants on illness time course in mood disorders. Journal of psychiatric research, 35(4), 217-223. |
| Bioplar Disorder | DISC1 | Hodgkinson CA, Goldman D, Jaeger J, et al. Disrupted in schizophrenia 1 (DISC1); association with schizophrenia, schizoaffective disorder, and bipolar disorder. Am J Hum Genet, 2004; 75(5): 862-872 |
| | BDNF | Sklar P, Gabriel S B, McInnis M G, et al. Family-based association study of 76 candidate genes in bipolar disorder: BDNF is a potential risk locus. Brain-derived neutrophic factor. Mol Psychiatry. 2002; 7(6): 579-593. |
| | DAOA | Prata D, Breen G, Osborne 5, Munro J, St Clair D, Collier D. Association of DAO and G72(DAOA)/G30 genes with bipolar affective disorder. Am J Med Genet B Neuropsychiatr Genet. 2008; 147B(6): 914-917. |
| | DTNBP1 | Raybould R, Green EK, MacGregor 5, et al. Bipolar disorder and polymorphisms in the dysbindin gene (DTNBP1). Biol Psychiatry. 2005; 57(7): 696-701. |

TABLE 5-continued

Human genes associated with psychiatric disorder

| Disease | Gene | Reference |
|---|---|---|
| | COMT | Mynett-Johnson LA, Murphy VE, Claffey E, Shields D C, McKeon P. Preliminary evidence of an association between bipolar disorder in females and the catechol-O-methyltransferase gene. Psychiatr Genet. 1998; 8(4): 221-225. |
| | NRG1 | Thomson P A, Christoforou A, Morris S W, et al. Association of Neuregulin 1 with schizophrenia and bipolar disorder in a second cohort from the Scottish population. Mol Psychiatry. 2007; 12(1): 94-104. |
| Anxiety Disorders | SERT | Murphy, D. L., Lerner, A., Rudnick, G., & Lesch, K. P. (2004). Serotonin transporter: gene, genetic disorders, and pharmacogenetics. Molecular interventions, 4(2), 109. |
| Schizophrenia | APBA2 | Need, A. C., Ge, D., Weale, M. E., Maia, J., Feng, S., Heinzen, E. L., . . . & Goldstein, D. B. (2009). A genome-wide investigation of SNPs and CNVs in schizophrenia. PLoS genetics, 5(2), e1000373. |
| | CNTN5 | Glessner, J. T., Reilly, M. P., Kim, C. E., Takahashi, N., Albano, A., Hou, C., . . . & Hakonarson, H. (2010). Strong synaptic transmission impact by copy number variations in schizophrenia. Proceedings of the National Academy of Sciences, 107(23), 10584-10589. |
| | CNTNAP2 | Friedman, J. I., Vrijenhoek, T., Markx, S., Janssen, I. M., Van der Vliet, W. A., Faas, B. H. W., . . . & Veltman, J. A. (2007). CNTNAP2 gene dosage variation is associated with schizophrenia and epilepsy. Molecular psychiatry, 13(3), 261-266. |
| | CYFIP1 | Song, W., Li, W., Feng, J., Heston, L. L., Scaringe, W. A., & Sommer, S. S. (2008). Identification of high risk DISC1 structural variants with a 2% attributable risk for schizophrenia. Biochemical and biophysical research communications, 367(3), 700-706. |
| | DISC1 | Song, W., Li, W., Feng, J., Heston, L. L., Scaringe, W. A., & Sommer, S. S. (2008). Identification of high risk DISC1 structural variants with a 2% attributable risk for schizophrenia. Biochemical and biophysical research communications, 367(3), 700-706. |
| | DLG1 | Consortium ISR: Rare chromosomal deletions and duplications increase risk of schizophrenia. Nature 2008, 455: 237-241. |
| | DLG2 | Xu B, Roos J L, Levy S, van Rensburg E J, Gogos J A, Karayiorgou M: Strong association of de novo copy number mutations with sporadic schizophrenia. Nat Genet 2008, 40: 880-885. |
| | DLGAP2 | Guilmatre A, Dubourg C, Mosca A L, Legallic S, Goldenberg A, Drouin-Garraud V, Layet V, Rosier A, Briault S, Bonnet-Brilhault F et al.: Recurrent rearrangements in synaptic and neurodevelopmental genes and shared biologic pathways in schizophrenia, autism, and mental retardation. Arch Gen Psychiatry 2009, 66: 947-956. |
| | ERBB4 | Walsh T, McClellan J M, McCarthy S E, Addington A M, Pierce S B, Cooper G M, Nord A S, Kusenda M, Malhotra D, Bhandari A et al.: Rare structural variants disrupt multiple genes in neurodevelopmental pathways in schizophrenia. Science 2008, 320: 539-543. |
| | NRXN1 | Stone, J. L., O'Donovan, M. C., Gurling, H., Kirov, G. K., Blackwood, D. H., Corvin, A., . . . & Kwan, S. L. (2008). Rare chromosomal deletions and duplications increase risk of schizophrenia. Nature, 455(7210), 237-241. |
| | SLITRK2 | Piton, A., Gauthier, J., Hamdan, F. F., Lafreniere, R. G., Yang, Y., Henrion, E., . . . & Rouleau, G. A. (2010). Systematic resequencing of X-chromosome synaptic genes in autism spectrum disorder and schizophrenia. Molecular psychiatry, 16(8), 867-880. |
| | SHANK3 | Gauthier J, Champagne N, Lafreniere R G, Xiong L, Spiegelman D, Brustein E, Lapointe M, Peng H, Cote M, Noreau A et al.: De novo mutations in the gene encoding the synaptic scaffolding protein SHANK3 in patients ascertained for schizophrenia. Proc Natl Acad Sci USA 2010, 107: 7863-7868. |

In some embodiments, the modification of the teleost gene is transient. In some embodiments, the modification of the teleost gene is permanent.

In some embodiments, the teleost gene in the teleost is mutated. In some embodiments, the mutation is a loss of function mutation. In some embodiments, the mutation is a gain of function mutation.

In some embodiments, the teleost gene in the teleost is silenced. In some embodiments, the expression product (such as mRNA and/or protein) of the teleost gene are modified. In some embodiments, there is provided a modified teleost comprising a mutation in the ortholog of the human potassium channel Kv1.1 teleost gene.

In some embodiments, there is provided a modified teleost comprising a mutation in the kcna1 teleost gene. Kcna 1 is a potassium voltage-gated channel protein of the shaker-related subfamily. It is the zebrafish ortholog to the Drosophila shaker mutants and human KCNA1. Mutation in KCNA1 has been associated with human epileptic patients. In some embodiments, the mutation in the kcna1 teleost gene is a loss of function mutation (for example a mutation located at Exon 2 of the kcna1 teleost gene).

In some embodiments, there is provided a modified teleost comprises a mutation in the scn1a teleost gene. Scn1a is a type I voltage-gated sodium channel protein. It is the zebrafish ortholog to human mutations that cause Dravet syndrome. In some embodiments, the mutation in the scn1a teleost gene is a loss of function mutation (for example a mutation located at Exon 2 of the scn1a teleost gene).

The modified teleosts described herein may exhibit a behavioral phenotype that is indicative of human brain dysfunction, and the teleosts can be selected for use on such basis. For example, in some embodiments, the teleost exhibits neuronal hyperactivity. In some embodiments, the teleost exhibits loss of neuronal function.

In some embodiments, the teleost phenocopies a brain dysfunction disorder such as epilepsy, ADHD, autism, AD, PD, and human brain tumor. This can be determined, for example, by analyzing the behavior, neuronal activity, symptoms or characteristics associated with the brain dysfunction disorder, gene expression profiles, signaling pathways, etc.

Also provided herein are methods of making teleosts described herein. In some embodiments, the teleost gene in the teleost is mutated. In some embodiments, the mutation is a loss of function mutation. In some embodiments, the mutation is a gain of function mutation. Methods of mutating a teleost gene in a teleost (for example by introducing a mutation) are known in the art, and include, for example, zinc finger nuclease cleavage, TALEN, and random mutation Zinc finger nuclease cleavage has been described, for example, at W02010076939. The mutated teleost gene, when produced in vitro, can be introduced into the teleost by methods such as microinjection.

Zinc finger nucleases (ZFNs) involves modular assembly of DNA-binding domains that typically contain three individual zinc finger repeats that can each recognize a 3 base pair DNA sequence, which are then linked to the restriction endonuclease FoId. Since FoId must dimerize in order to cleave DNA, a pair of ZFNs can be used to target non-palindromic DNA sites.

In some embodiments, mutations are introduced into the teleost randomly, for example by following methods known in the art. The teleost comprising a desired mutation is subsequently identified by using a screening method, for example based on behavioral screening and/or DNA analysis. Methods of analyzing DNA mutations in a teleost teleost gene is known in the art, and can include, for example, PCR-based amplification and pyrosequencing (see W02007002204).

In some embodiments, the TALEN system is used for introducing a teleost gene mutation into the teleost. TALEN has been described, for example, at U.S. Pat. No. 8,450,471. Briefly, Transcription activator-like (TAL) effectors (TALEs) are proteins secreted by Xanthomonas bacteria that contain a highly conserved 33-34 amino acid sequence except at the 12th and 13th amino acid position. These two amino acid positions are variable and show a strong correlate with specific nucleotide recognition. Thus, DNA binding domains can be engineered by modular assembly of specific TALEs that possess the appropriate amino acid at positions 12 and 13 to bind target DNA sites in the genome. As with ZFNs, these DNA binding domains are then linked to a Fok1 nuclease that then cleaves double stranded DNA to allow engineering across the target locus. In some embodiments, the TALEN system can employ non-homologous end-joining (NHEJ), whereby endogenous cellular repair mechanisms attempt to fix the double strand break created by the TALEN construct and occasionally either erroneously insert a base pair or accidentally delete a base pair. These insertion/deletion mistakes are referred to as "indels" and often times these indels cause a frameshift mutation and thus, a null protein. In other embodiments, the TALEN system can employ homology-directed repair (HDR), which relies on co-injection of short, single-stranded oligonucleotides inserted into the locus where the double strand break occurs thereby creating subtle changes to the DNA sequence (such as, without limitation, a single nucleotide polymorphism (SNP)). In yet another embodiment, the TALEN system can employ homologous recombination (HR) wherein long, double-stranded DNA donors are used to direct large changes in a given DNA sequence and which can be used, for example, for insertion of reporter proteins (such as, without limitation, fluorescent report proteins for use in high throughput robotics).

In some embodiments, the expression products (such as mRNA and/or protein) of the teleost gene are modified. For example, the expression product of the teleost gene can be modulated through activation or inhibition of transcription of the teleost gene by means of regulatory proteins, such as transcription factors or repressors. In some embodiments, the expression product of the teleost gene can be modulated through stabilization or destabilization of the mRNA derived from the teleost gene by means of regulatory proteins and/or ribozymes.

In some embodiments, the expression product of the teleost gene is modulated through activation or inhibition of translation of the mRNA derived from the target teleost gene by means of regulatory proteins, antisense molecules, morpholinos, or/and RNAi molecules. Antisense molecules include, for example, short DNA, RNA or nucleic acid analog fragments (such as, for example, PNAs, LNAs, phosphorothioate oligonucleotides, morpholino oligonucleotides, 2-fluoro-RNAs or mixed compounds thereof) with a nucleic acid sequence of about 10 nucleotides or more which are complementary to a partial area of the mRNA derived from the target teleost gene. Suitable RNAi molecules include, for example, double-string RNA molecules with a length of about 10 base pairs or more, such as about 18 base pairs or more, or about 20 base pairs or more. The RNAi molecules can either be manufactured synthetically or in a vector-based manner in the target cells (Elbashir et al., Nature 411: 494-498, 2001; Sui et al., Proc. Natl. Acad. Sci. USA 99: 5515-5520,2002). The sequence of the RNAi molecules is selected in such a manner that it corresponds to specific sequence areas of the mRNA derived from the teleost gene. In some embodiments, the teleost gene in the teleost is silenced, for example through CRISPR silencing, mopholino, or RNAi.

CRISPR silencing has been described, for example, at EP2336362 and WO2012164565. Clustered Regularly Interspaced Short Palindromic Repeats (CRISPRs) are short, multiple repeats of base pair sequences across a single DNA loci. For example, each CRISPR sequence contains a series of base pairs followed by the same or similar base pairs in reverse order and then a space region of approximately 30 base pairs. CRISPRs rely on crRNA and tracrRNA for sequence-specific silencing such that Cas9 (for example) can serve as an RNA guided DNA endonuclease that cleaves DNA upon crRNA-tracrRNA target recognition. In some embodiments, the expression product of the teleost gene is modulated through activation or inhibition of splicing of the mRNA derived from the target teleost gene.

In some embodiments, the expression product of the teleost gene is modulated through an activator or inhibitor of the protein expressed by the teleost gene. Activators can include, for example, proteins, peptides, small molecules, agonist antibodies, etc. The activators may lead to stabilization of the protein product of the teleost gene and/or increase the activity of the protein encoded by the teleost gene Inhibitors can include, for example, protein, peptides, small molecules, antagonist antibodies, etc. The inhibitor may lead to destabilization of the protein product of the teleost gene and/or inhibit the activity of the protein product of the teleost gene.

The above regulatory enzymes, repressors, ribozymes, antisense or RNAi molecules, activators, inhibitors and/or antibodies described above can be transferred through transformation into the cells. The transformation can be carried out directly or by using expression vectors in accordance with prior-art procedures, e. g. through calcium phosphate coprecipitation, lipofektion, electroporation, particle bombardment, or viral infection. Suitable expression vectors comprise both viral systems, such as retroviral (Lin et al., Science 265: 666-669,1994) or adenoviral systems, as well as different bacterial plasmids. Such vectors are sufficiently known to those in the art (Maniatis et al., 1989, Molecular Cloning, A Laboratory Manual, Cold Spring Harbor Press). In addition, larvae can be transferred through microinjection during the early (preferably 1-8 cell stage) embryonic stage. This also applies to the transfer of transgenes, for example to the expression of RNAi-mediating short RNAs or for the expression of other RNAs (coding or non-coding) (Stuart et al., Development 103: 403-412,1998; Westerfield, M., The zebrafish book. A guide for the laboratory use of zebrafish (*Danio rerio*), 4th ed., Univ. of Oregon Press, Eugene, 2000; Thermes et al., Mech. Dev.: 91,2002; Medaka homepage http://bioll.bio. nagoya-u.ac.jp:8000/; Sui et al., 2002, supra).

Mitochondrial Function Assays

The methods of the present invention uses mitochondrial function assays to identify compounds (or human gene mutations) of interest. Various methods of assaying mitochondrial functions are known in the art. For example, mitochondrial function can be assayed by measuring one of more mitochondrial output selected from the group consisting of: ATP level and/or the level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change (such as mitochondrial swelling, mitochondrial fission/fusion, and mitochondrial aggregation), transcriptional changes in mitochondrial teleost genes, and mitochondrial membrane potential. In some embodiments, two or more (for example 3, 4, 5, 6, 7, 8, 9, 10, or more) of the mitochondrial outputs are assayed.

In some embodiments, the mitochondria output is ATP level and/or the level of ATP metabolite. Levels of phosphorylated adenosine nucleotides—ATP and its metabolites ADP and AMP—define the energy status of the living cell, and ultimately confer information about mitochondrial function. There are various ways of determining ATP levels, which include, but are not limited to, ATP content, changes in ATP production, and ATP synthesis. In some embodiments, the method involves chemiluminescence measures to determining ATP levels. In some embodiments, the method involves HPLC-based protocols for determining ATP levels.

For example, ATP synthesis can be measured in cells isolated from whole zebrafish embryos. Zebrafish can be maintained in E3 buffer until desired stage. For fish younger than 5 days post fertilization (dpf), whole embryos can be collected. For fish older than 5 dpf, the head is dissected from the tail, just prior to the swim bladder. Embryos are homogenized and the cells resuspended in ATP buffer. Cells are incubated with digitonin, washed, and pelleted. The cells are then resuspended using ATP buffer supplemented with adenosine pentaphosphate, malate+pyruvate mixture, ADP, and luciferase. Baseline luminescence is generated using the ATPase inhibitor oligomycin in control samples. ATP synthesis is measured by capturing light emission in a counting luminometer every 15 sec for 5 minutes (adapted from Manfredi et al (2002) Methods, 26:317).

In some embodiments, the mitochondrial output is mitochondrial respiration rate. Measurement of cell respiratory control reports the rate of ATP production, the proton leak rate, the coupling efficiency, the maximum respirator rate, the respiratory control ratio, and the spare respiratory capacity—making this readout the all-around best assay to assess mitochondrial dysfunction. In some embodiments, the assay is conducted in multiwell format using oxygen-dependent fluorescence quenching to monitor oxygen concentration in the medium. In some embodiments, the mitochondrial output is measured by using the Seahorse extracellular flux analyzer. Seahorse extracellular flux analyzers have been developed that monitor oxygen uptake in distinct sessions to enable modulation of the cells throughout the experiment. Thus, mitochondrial function can be manipulated to shed insight into the following: non-mitochondrial respiration, basal respiration, ATP turnover, proton leak, coupling efficiency, maximum respiration, cell respiration control ratio, and spare respiratory capacity.

One exemplary protocol for measuring oxygen consumption rates (OCR) using Extracellular Flux Analyzer (Seahorse Bioscience, Billerica Mass.) is described below. First, sensor cartridges are hydrated in XF Calibrant Solution in 24-well cell culture microplates overnight at 28.5 C. Prior to experiment, injection ports are filled with appropriate treatments and loaded into XH24 instrument. Staged zebrafish embryos (3 days post fertilization used here) are individually placed in 20 of the 24 wells (4 wells serve as controls) on the islet microplate filled with E3 buffer and islet plate capture screens are placed on top to keep living zebrafish from moving during experiment. Plates are loaded into the instrument and six measurement cycles were taken to establish basal rates, which were then followed by treatment injections and 18 additional measurement cycles. OCRs were calculated at cycles five and six and then averaged to create the basal respiration. FCCP treatment was used to measure maximum OCR and oligomycin was used to measure minimum OCR.

In some embodiments, the mitochondrial output is reactive oxygenated species. Understanding Reactive Oxygenated Species (ROS) signaling relies on the ability to visualize and quantify ROS dynamics on a local, compartmental and global cellular level. Thus, sensitivity and spatiotemporal resolution are key for proper measurement of ROS levels and synthetic and genetically encoded fluorescent protein-based ROS indicators have been developed. In short, ROS are oxygen metabolites that are primarily generated from electron leakage from the mitochondrial electron transfer chain. Superoxide radical (02-) is the predominate ROS species produced and it is subsequently converted into hydrogen peroxide (H2O2). ROS can be measure by a variety of fluorescent methods (reviewed, Wang et al (2013), J Mol Med, 91:914), including small-molecule fluorescent probes (e.g., DCFH, mitoSOX, DCFH-DA) fluorescent protein-based indicators (e.g., cpYFP, HyPer), and FRET-based ROS indicators (e.g., CFP/YFP linked polypeptides). In addition, Electron Spin Resonance (Han et al, (2010) Archives of Pharmacal Research. 33(9): 1293), cytochrome C reduction, chemiluminescence, and hydroxylation of salicylate can also detect ROS levels (reviewed, Murrant et al (2001), Microsc Res Tech, 55(4):236.

An exemplary protocol for measuring DCFH-DA in whole zebrafish embryo is provided herein. Briefly, the protocol involves seeding newly fertilized zebrafish embryos into 96 well plate and incubate with E3 media (28 C). After 24 hours, treat with 1 mM H2O2 for either 24 hr, 48 hr, 72 hr, depending on experimental design. At the desired end point, add DCFH-DA (11.1 M-101.1 M) for 20 minutes. Wash 3×, 5 min with E3 to remove excess DCFH-DA. The amount of ROS can be quantified by detecting the levels of fluorescence under 488 nm excitation. Plate readers, high throughput confocal microscopy, or compound microscopes can be used to measure fluorescent levels in whole embryo or in a select human brain region (if using microscopy). Similar reference: Kishi et al (2008) PLoS Genetics 4(8): e1000152.

In some embodiments, the mitochondrial output is reactive nitrogen species. Reactive nitrogen species (RNS) act in concert with ROS and thus these two species are collectively referred to as ROS/RNS. RNS is produced by nitric oxide (NO) interacting with superoxide (02-) to form peroxynitrite (ONOO—). Peroxynitrite is a highly reactive species that can cause cellular damage. RNS is measured similar to ROS above, using fluorescent and chemiluminescent probes that allow assay for NO and nitric oxide synthase (NOS) as a readout for RNS dynamics.

A similar protocol as described above for measuring reactive oxygen species can be employed with Greiss reagent (Life Technologies) for measuring nitrites. The colorimetric reagent can be quantified, for example, by using a chemiluminescent plate reader.

In some embodiments, the mitochondrial output is mitochondrial calcium homeostasis. Mitochondrial calcium homeostasis is precisely maintained, thus any modulation in mitochondrial $Ca^{2+}$ levels indicates mitochondrial dysfunction. Mitochondria are able to transport $Ca^{2+}$ through the outer mitochondrial membrane via voltage-dependent anion channel (VDAC) activity and through the inner mitochondrial member by the calcium uniporter to store $Ca^{2+}$ in their matrix. Traditionally $Ca^{2+}$ can be measured using fluorescent indicators, particularly Rhod-2, to illustrate any changes in $Ca^{2+}$ concentrations across the mitochondrial membranes (e.g., Nishiyama et al (2013) Acta Neurochir Suppl, 118:65). Here, we outline a procedure in zebrafish embyros that allows the study of mitochondrial capacity to uptake Ca $Cal^{2+}$ ions (Prudent et al (2013) Protocol Exchange at Nature.com).

In one exemplary protocol, zebrafish embryos are grown in E3 media until developmental stage required. Embryos are then collected, homogenized, and cells pelleted by centrifugation. Cells are disrupted by syringe resuspension and subcellular fractionation by centrifugation is used to isolate mitochondria. Calcium uptake is assayed by resuspension of the mitochondria in KCL buffer and addition of OregonGreen 5N (Life Technologies), which binds cytosolic calcium. Cells are plated into a 96-well plate and Oregon Green 5N intensity is measured using a microplate reader. Fluorescent intensity is measured every 2 seconds 30 seconds to achieve baseline, then mitochondrial calcium uptake is measured by injection of 200 uM CaC12 (final concentration 20 uM) and the decrease is fluorescence intensity following the peak induced by CaC12 injection is captured every 2 sec for the remaining 4.5 min.

In some embodiments, the mitochondrial output is mitochondrial appearance change, which includes, but is not limited to, mitochondrial swelling, mitochondrial fission/fusion, and mitochondrial aggregation. Ultrastructural changes in mitochondria can serve as a readout for mitochondrial dysfunction. For example, mitochondrial swelling is an indicator for opening of the mitochondrial permeability transition pore. Moreover, changes in fission, fusion, and aggregation of mitochondria indicate loss of mitochondria dynamic behaviors. Optical approaches are becoming favored over electron microscopy to measure changes in mitochondrial appearances because they allow measurement of temporal dynamics in living specimens.

In one exemplary protocol, cell cultures are grown to a confluence of a single layer. Mitochondria dynamics are imaged using an inverted microscope and time-lapse confocal microscopy, captured 25 sec intervals across a 20 minute period. The stage is maintained at 37 C for the entire experiment. For mitochondrial swelling, the thinness ration (TR) can be calculated to illustrate changes in mitochondria diameter (Gerencser et al (2008) Biophys J, 95(5):22583). Fission, fusion, aggregation events can be quantified by manual review of captured images. Newer techniques allow quantification in living cells by using a photo-conversion of matrix targeted photoactivatable GFP (Lovy et al (2012) JoVE 65:e3991). The rate by which the photoconverted molecules equilibrate across the mitochondrial population serves as a measure of fusion activity. Current experiments seek to optimize this technology for whole animal imaging using zebrafish embryos.

In some embodiments, the mitochondrial output is transcriptional changes in mitochondrial teleost genes. Mitochondrial dysfunction can elicit broad effects on gene transcription in either the nucleus or mitochondria itself. Indeed, roughly 100 genes are involved in mitochondrial biogenesis and function, and thus, monitoring expression profiles of their transcripts (mRNA, real-time quantitative PCR below) or proteins (western blot) can serve as readout of overall mitochondrial function.

mRNA determination using real-time quantitative PCR can be carried out according to the following exemplary protocol. Briefly, zebrafish embryos are grown to the desired stage. For fish younger than 5 days post fertilization (dpf), whole embryos are collected. For fish older than 5 dpf, the head is dissected from the tail, just prior to the swim bladder. Embryos are homogenized and total RNA is isolated using TriZol (Life Technologies)) and cDNA is transcribed using Superscript (Life Technologies). Primer sets are designed to span an exon-exon boundary whenever possible and validated to ensure amplification of a single product with appropriate efficiency and Tm. The relative gene expression was determined by loading cDNA+primer set onto a 96-well plate and amplification and fluorescence detection is conducted with the ABI PRISM 7700 (Applied Biosystems). For quantitative comparison of gene expression, data are extracted from each RT-qPCR run and analyzed using the comparative Ct method.

Protein level measurement using Western Blot can be carried out according to the following exemplary protocol. Briefly, zebrafish embryos are grown to desired stage and collected as per above. Triton X-100 lysis buffer is used to extract total cellular protein from homogenized embryos. Protein (20-50 μg) is loaded and separated on a SDS-PAGE gel, then transferred to a nitrocellulose membrane. Membranes are incubated in blocking solution, followed by overnight exposure to primary antibody. After a series of washes, the membrane is exposed to secondary antibodies Immunoreaction is visualized with luminescence from CL Western Blotting reagent (GE Healthcare) and measured using a ChemiDoc Imagining system. The intensity of the illuminant signal is indicative of protein levels.

In some embodiments, the mitochondrial function is assayed by using a reporter construct. For example, control elements of mitochondrial teleost genes whose level changes as a result of modulated mitochondrial function can be linked to a reporter teleost gene (such as GFP), and the existence or intensity of the reporter teleost gene product (such as fluorescence) can be used as an indicator of mitochondrial function. In some embodiments, the mitochondrial output is mitochondrial membrane potential. Changes in membrane potential ($\Delta_\Psi$) or differences in pH across the mitochondrial inner membrane ($\Delta pH_m$) can be measured using fluorescent probes. Although these experiments are more commonly conducted using isolated mitochondria, with careful controls and absolute calibration, accurate relative values of potential and pH can be obtained (reviewed, Davidson et al (2007) Methods Mol Bio. 372: 421).

Briefly, TMRM, TMRE, and R123 can be used as fluorescent probes. Low nanomolar concentrations of TMRM are equilibrated with intact cells for 60 min No washing is required for this assay. Either a compound (wide field) or confocal (single cell resolution) fluorescent microscope is used to quantify the concentration gradient of the cation between the cytoplasm and matrix. For example, $\Delta_\Psi$) of 150 mV indicates a 300-fold concentration gradient between the matrix and cytoplasm. Ongoing experiments are aimed at determine optimal conditions to measure $\Delta_\Psi$ in whole zebrafish embryos using the LightSpeed (Zeiss) confocal microscope designed specifically for speed in small samples such as zebrafish embryos.

Drug Screening Systems

Also provided herein are drug screening systems comprising two or more components (including for example devices and reagents) for carrying out the methods described herein. For example, in some embodiments, there is provided a drug screening system comprising a device (for example a device comprising an array of wells) for culturing the teleost and a device for analyzing mitochondrial output of the teleost. In some embodiments, the system further comprises a device for a behavioral assay. In some embodiments, the system further comprises a device for applying a compound or a library of compounds to the teleost. In some embodiments, the system comprises teleosts, such as the modified teleosts described herein.

The invention can be further understood by reference to the following examples, which are provided by way of illustration and are not in any way meant to be limiting.

EXAMPLES

Example 1

Construction of Human Disease Models (Such as Epilepsy) in Zebrafish

In general, published literature is used to identify genes that are associated with disease states in humans. Candidate genes are ranked based on the strength of the data indicating causality. For example, genes were loss of function is strongly linked to the etiology of disease are ranked higher than genes that were uncovered in genome wide association studies (GWAS) but of unknown significance. Bioinformatic tools are then employed to identify zebrafish orthologs of top candidate human genes. Due to genome duplication that occurred in teleosts, many human genes have two zebrafish orthologs. Sequence similarity is then examined between the paralogs, with paralogs that are highly conserved ranked lower than paralogs with significant variation in the genome. In some cases, variation in tissue expression overrides genetic data (e.g., highly similar paralogs that are differentially expressed in the brain and peripheral tissue, for example, will be kept as a candidate gene). This process is continued until target genes are identified for each disease state of interest.

To identify teleost genes that are associated with epilepsy, we conduct literature search to identify disease-causing mutations. We then rely on systems biology approaches to cluster the teleost gene list into networks or pathways using online tool, such as BiNGO. CLASSIFI, eGOn, and others. Each teleost genetic node is then analyzed to identify the most upstream teleost genetic component. Mutant zebrafish models are created that best represent each node.

After the target teleost gene was identified, online tools (e.g., TAL Effector-Nucleotide Targeter (https://tale-nt.cac-.comelLedu/node/addisingle-tale) were used identify sets of TALEN recognition sites that meet specific requirements. We relied on recognition sites that were between 15 and 30 basepairs in length and separated by a spacer region that is 18-30 basepairs in length. The software then listed the repeat-variable di-residue (RVD) sequences that are needed to construct the corresponding custom TALEN. Assembly of this custom TALEN was carried out over 5 days. First the left and right recognition constructs were assembled and then joined into one vector to create a single final construct. Exact details were listed in Cermak et al, Nucleic Acids Research, 39:e82 (2011). All constructs are verified using the mismatch detection assay (T7/E1 assay) in embryonic zebrafish.

Constructs with >70% efficiency were microinjected into embryonic zebrafish at the one-cell stage. To knock-in a single disease-causing mutation, a short oligo designed to match the spacer region with the exception of a single disease-causing mutation was co-injected with the TALEN construct. Alternatively, errors made by cells' endogenous DNA repair mechanism in correcting the change induced by the TALEN construct were relied on (e.g., non-homologous end joining) Embryonic zebrafish are allowed to grow until adults (3 months) and then sequenced using PyroMark Q24 pyrosequencing technique (Qiagen). Insertions and deletions ("indels") are analyzed in individual zebrafish. Mutant lines are outcrossed to wild type strain (TL strain) and then maintained in the colony. FIG. 1 shows the creation and validation of "epileptic" zebrafish models. FIG. 1A shows that Fok1 nuclease linked to TALEN domains can cleave double stranded DNA and allow for genetic changes. FIG. 1B shows sequence for a TALEN-injected zebrafish embryo versus wildtype for the F3 founder line (top) and a sequence for the F1 and F2 founder lines are also shown relative to WT (bottom). FIG. 1C provides a picture showing extracellular field recordings from zebrafish and sample extracellular field recordings from WT (top three lines) and mutant (bottom three lines) zebrafish. The presence of high frequency, large-amplitude spikes in mutant are indicative of hyper-excitability, consistent with epileptic rodent models. FIG. 1D shows sample locomotion tracking plots for WT and mutant zebrafish+/−drug. The light scribe represents the zebrafish larvae and dark scribe traces indicate movement. WT zebrafish display little locomotion under normal conditions, whereas kcna1−/−zebrafish display rapid locomotion phenotype, shown by others to be indicative of convulsive seizure-like activity (see, e.g., Baraban et al, 2005). As shown, the addition of an anticonvulsant drug decreases this hyperactive locomotion in mutant zebrafish.

Example 2

Mitochondrial Genes are Differentially Regulated Across Three Models of Epilepsy This Example shows that mitochondrial function is a valid target for the identification of drugs to treat epilepsy because mitochondrially-linked genes are dysregulated in three zebrafish models of epilepsy.

A custom $RT^2$ Profiler PCR Array (Qiagen) was created for zebrafish that profiles 84 genes involved in biogenesis and function of the mitochondria. The genes included in the array are regulators and mediators of mitochondrial molecular transport (for example, electron transport chain, oxidative phosphorylation, maintenance of membrane polarization and potential for ATP synthesis), the intrinsic apoptosis pathway that is activated by intracellular damage signaling, and genes responsible for translation and folding of proteins across the outer and/or inner mitochondrial membrane and matrix.

All morpholinos were designed and engineered by Gene Tools, LLC (Philomath, Oreg.). Slice-targeting morpholinos, which are designed to target an intron-exon boundary were used in the morpholino experiments disclosed herein. Thus, exons that display high homology to the human ortholog and low homology to a potential zebrafish paralog were denoted and the sequence uploaded to Gene Tools website for analysis and suggested morhpolino design.

To transiently knockdown a target gene in zebrafish, developing embryos at the one cell stage were injected with 2.6-4.6 nL (1 nM-50 nM) of morpholino. The most efficacious dose was determined by RT-PCR assays demonstrating alterative splice (smaller bands of different sizes), targeted degradation (no cDNA detected), or incorporation of the morpholino at the target locus (larger band detected. Sequences for kcna1 and scn1a morpholinos can be found in Table 1, infra.

Adult zebrafish were set up the night prior to the experiment and dividers were pulled at lights on the next morning (8 am). Freshly laid embryos were collected at t=0 and kcna1 and scn1a morpholinos were injected at the one cell stage. kcna1 and scn1a-morphants were incubated in the dark for 72 hours at 28° C. Embryos for PTZ-induction were raised in L:D conditions (14 hr light: 10 hr dark). PTZ treatment (10 mM) starts 8 hr prior to collection of larvae. Forty embryos per treatment group were collected and stored in RNAlater solution (Ambion) until use. RNA was extracted by grinding n=40 embryos collectively (n=3 groups per treatment) using a mortar and pestle. All RNA was exposed to DNase treatment and run over a column (Qiagen) to avoid genomic DNA contamination. RNA concentration was measured using nandrop. cDNA was synthesized from 500 ng total RNA using Qiagen QuantiTect Reverse Transcription kit. cDNA was added to RT2 SYBR Green master mix and aliquoted into $RT^2$ profiler 96-well PCR array (custom synthesized for zebrafish primers). The plate was loaded into an iCycler (Biorad). Data was analyzed using iCycler software using the ΔΔCt method.

As shown in FIG. 2, mitochondrial genes are differentially regulated across three models of epilepsy. As shown in Example 3 (below), a PTZ-induced model of epilepsy was likely not mediating neuronal hyperexcitability via a mitochondrially-mediated pathway. In contrast, here it is demonstrated that mitochondrial genes are both upregulated and downregulated in the PTZ-induction model, suggesting that the PTZ-induction model is more complicated in its underlying biology than previously considered. Second, the vast majority of genes are upregulated specifically in kcna1 morphants (n=37 genes), whereas only 3 genes are upregulated in the PTZ-induced model and no genes are upregulated in scna1 morphants. In contrast, many genes are downregulated in all three models. For example, PTZ-induced and scn1a morphants display 15 and 10 genes downregulated, respectively, whereas 9 shared genes are downregulated across all three models, implying that transcription of mitochondrial genes is especially dampened in models of epilepsy. Notably, gene transcript levels are largely unique to a particular model (i.e., there is little overlap of gene regulation across models). Combined, this suggests differing underlying etiologies to the epileptic phenotype observed across these three models.

Example 3

Drug Screening Using Epileptic Zebrafish

This Example utilizes the drug screening assay disclosed herein using morpholino-injected embryos to transiently knockdown genes of interest. Here, we compare three "epileptic" models for phenotypes in the behavioral assay: pharmacological-induction model (PTZ) and two genetic knockdown models (kcna1 and scn1a morphants).

Larvae were treated with morpholinos to kcna1 and scn1a as described above.

Zebrafish larvae (5 days post fertilization) were seeded into 96 well microliter plates containing vehicle solution and monitored for 20 minutes for hyperactivity. Morphants and WT zebrafish were exposed to drug for 10 minutes preincubation and then assayed for changes in hyperactivity for 20 minutes (Zebralab box). Drugs that decreased hyperactivity behavior by 40% in morphants were identified as "positive hits."

These positive hits were then verified by conducting a dose-response relationship using hyperactivity as readout. Drugs that resulted in a dose-dependent block of hyperactivity in mutant zebrafish larvae were carried forward into bioenergetics screening step.

Next, all positive hits were assayed for improve bioenergetics using Seahorse bioanalyzer (Seahorse, Inc). Briefly, morphant zebrafish were seeded into 24-well Islet Flux plates (Seahorse) and incubated with compound or vehicle for 10 minutes prior to analysis. Complete mitochondrial profile was assessed for each individual larvae. Drugs that improved bioenergetics by 40% were considered candidate drugs.

Figure 3A:
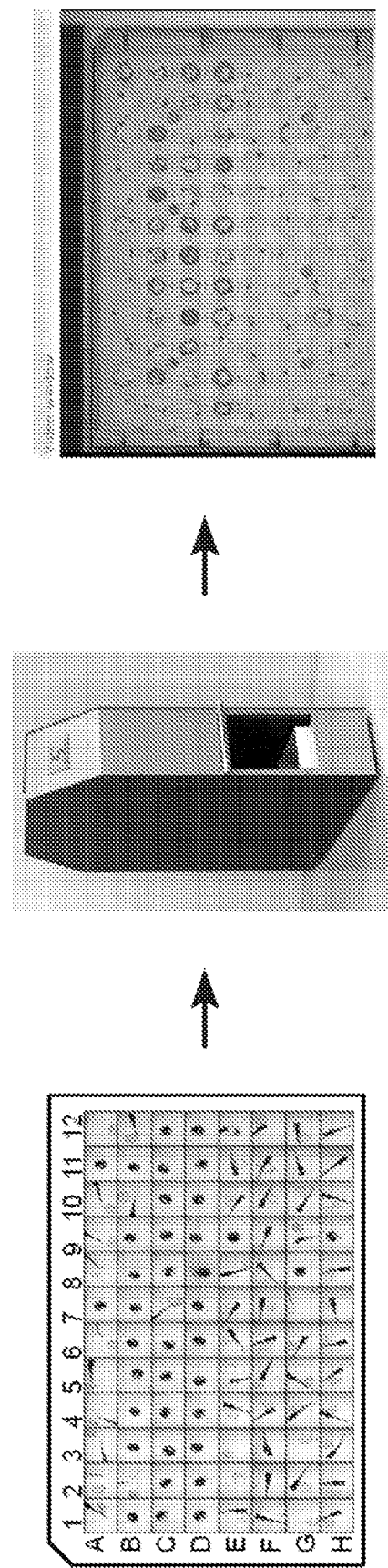
FIG. 3A. Workflow of behavioral assay. Zebrafish larvae (morphants and vehicle injected) were seeded into a 96-well plate and exposed to compounds. The 96-well plate was loaded into a zebrafish behavior box, and overall activity levels were captured (dark scripe=movement of a zebrafish).
Figure 3B:
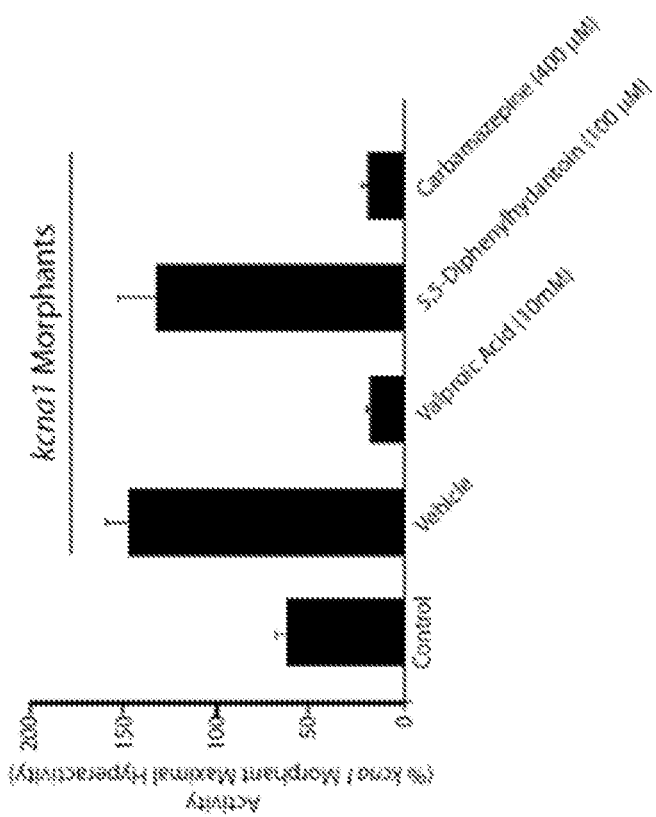
FIGS. 3B and 3C. Distinct effects of various compounds on PTZ-induced convulsion models (3B) and kcna1 zebrafish morphants (3C).
Figure 3C:
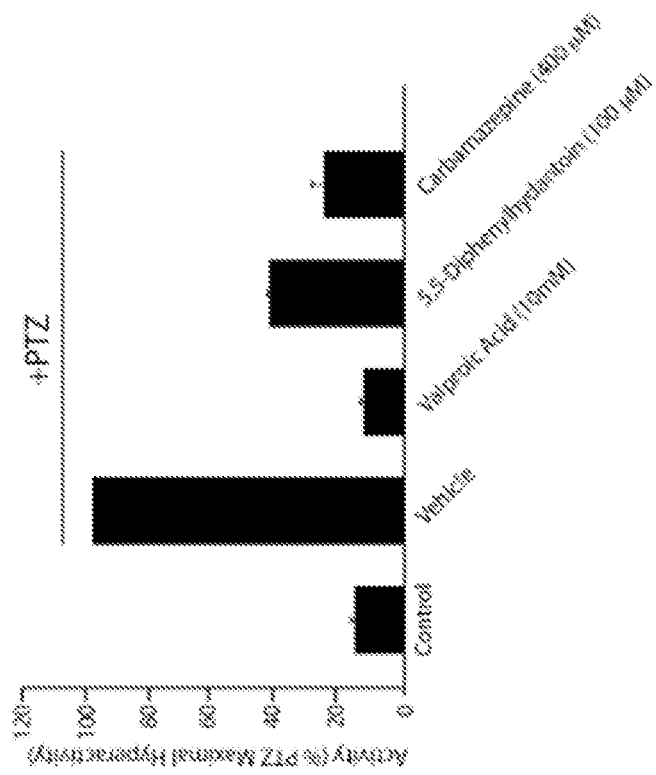
Figure 3D:
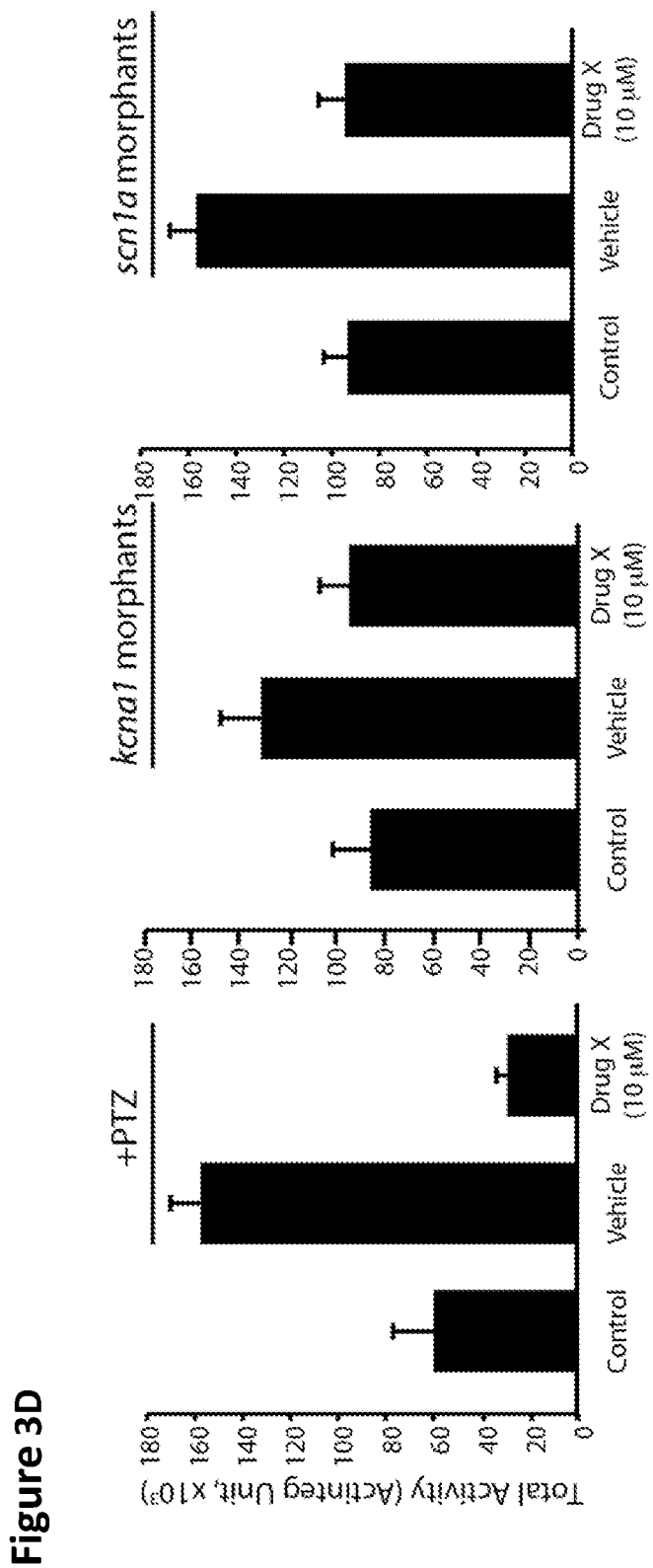
FIG. 3D. Drug X (10 mM) blocks hyperactivity in all three epilepsy models.

FIG. 3A provides workflow and results of behavioral analyses of hyperactive zebrafish using PTZ-induced convulsion model and kcna1 zebrafish morphants. As shown in FIGS. 2B and 2C, distinct effects of various compounds on PTZ-induced convulsion models (3B) and kcna1 zebrafish morphants (3C) were observed. First line anticonvulsant drugs all block PTZ-induced hyperactivity with no effect on kcna1 morphants. Valproic acid, which was shown to have no efficacy in refractory patients, also had no effect on the kcna1 morphants FIG. 3D illustrates that Drug X (10 µM) blocked hyperactivity in all three epilepsy models, illustrating that seizure-like hyperexcitability is responsive to therapeutic agents.

Figure 4A:
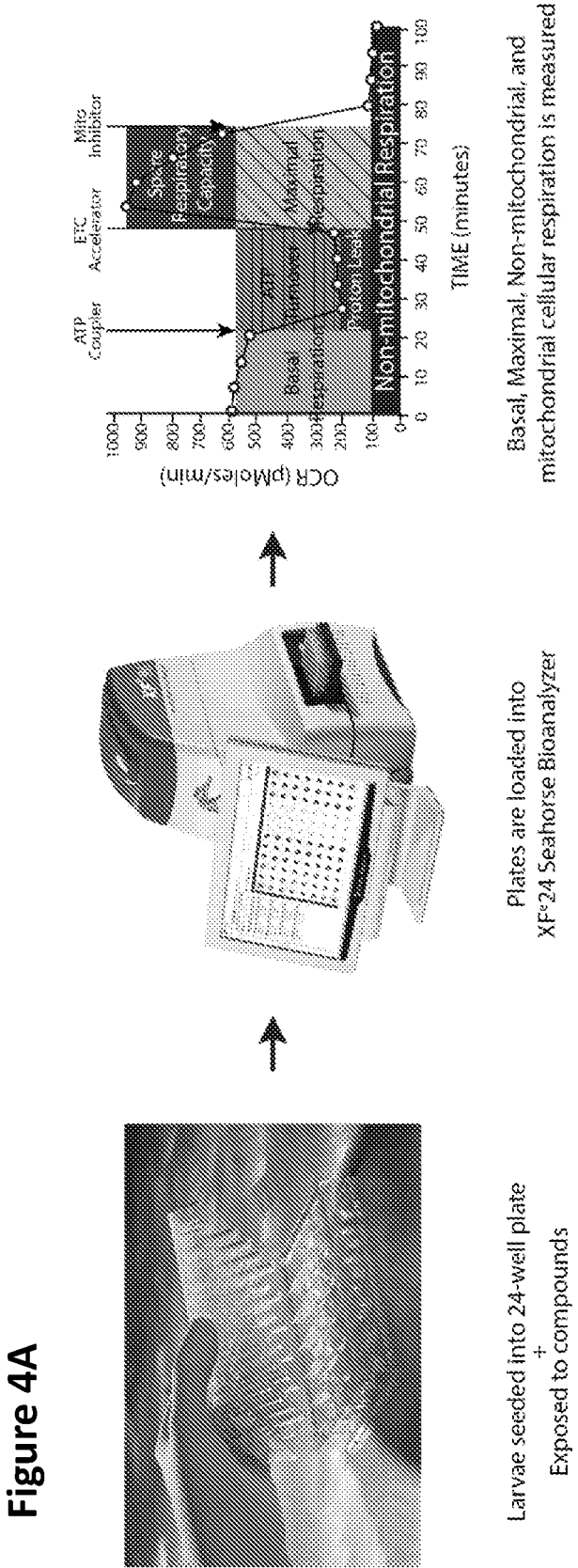
FIG. 4A. Workflow of cellular metabolism assay. Zebrafish larvae were seeded into 24-well plate and exposed to compounds. The plates were loaded into Xr24 Seahorse Bioanalyzer. Basal, maximal, non-mitochondrial, and mitochondrial cellular respiration were measured.
Figures 4B, 4C:
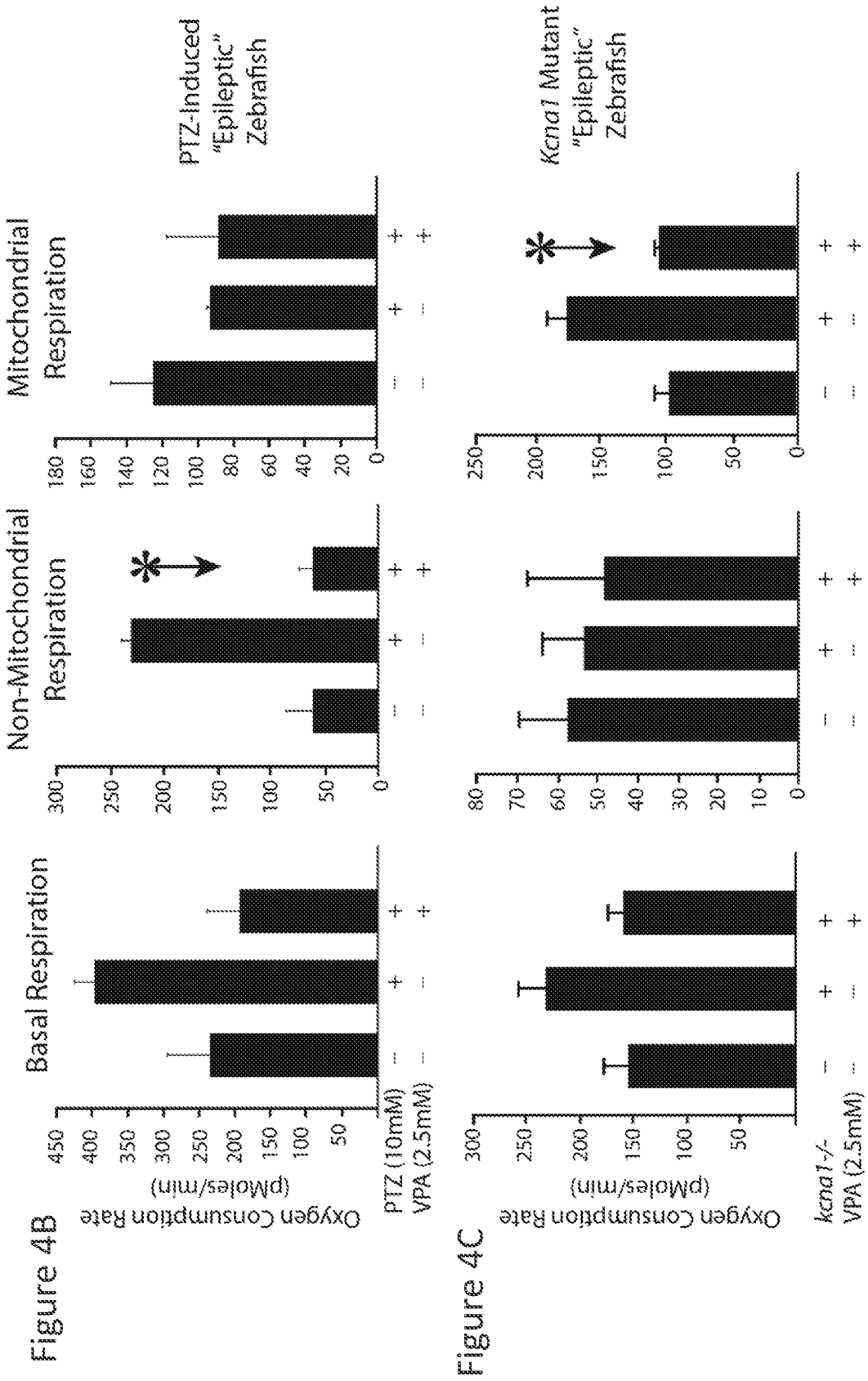
FIG. 4B. Measurements of individual components of metabolism in PTZ-induced hyperactive zebrafish. Basal respiration was elevated in PTZ treated larvae and blocked by Valproic Acid (VPA) via non-mitochondrial-mediated events.
FIG. 4C. Measurement of basal respiration in kcna1 morphants. Basal respiration was elevated in kcna1 morphant-treated larvae and was blocked by VPA via mitochondrial-mediated events (noted by asterisk-arrow).

FIG. 4 provides workflow and results of bioenergetic analyses in a hyperactive zebrafish. As shown in FIG. 4A, Zebrafish larvae were seeded into 24-well plate and exposed to compounds. The plates were loaded into XFe24 Seahorse Bioanalyzer. Basal, maximal, non-mitochondrial, and mitochondrial cellular respiration were measured. FIG. 4B shows measurements of individual components of metabolism in PTZ-induced hyperactive zebrafish (top). as well as measurement of basal respiration in kcna1 morphants (bottom). Basal respiration was elevated in PTZ treated larvae and blocked by Valproic Acid (VPA) via non-mitochondrial-mediated events. Basal respiration was elevated in kcna1 morphant larvae and was blocked by VPA via mitochondrial-mediated events (noted by asterisk-arrow).

Figure 5:
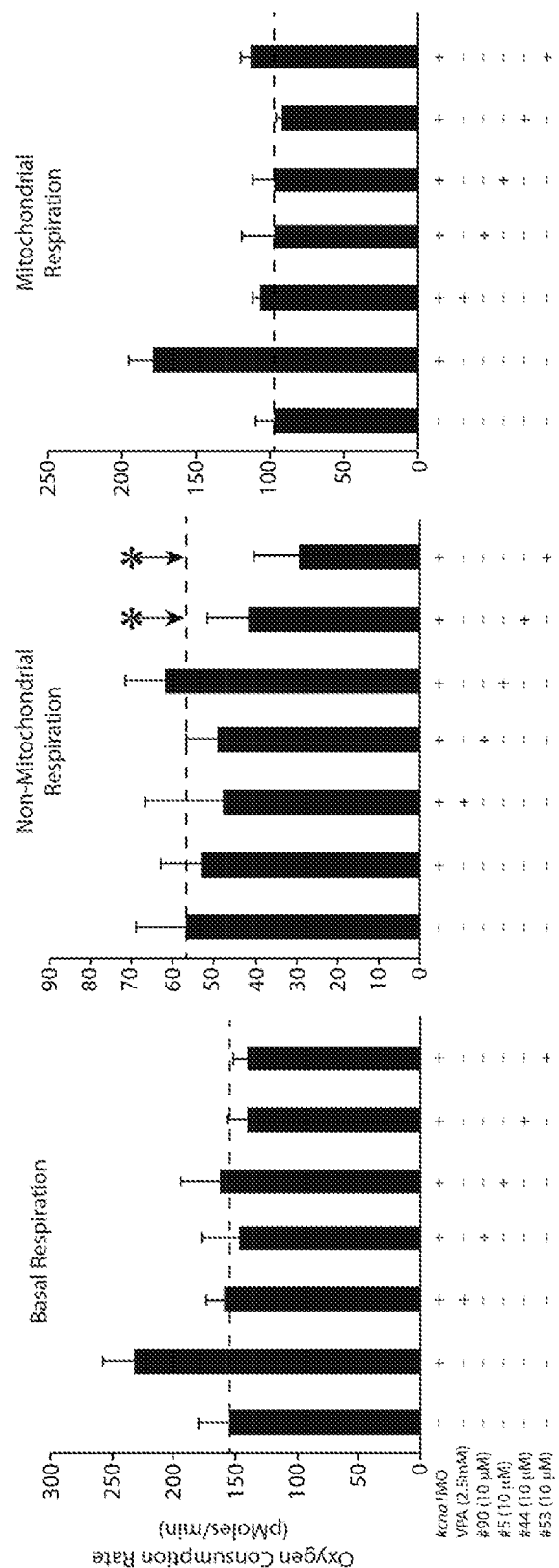
FIG. 5 shows the bioenergetics profiles of compounds uncovered during the drug screening in kcna1 morphant zebrafish.
Figures 6A, 6B, 6C:
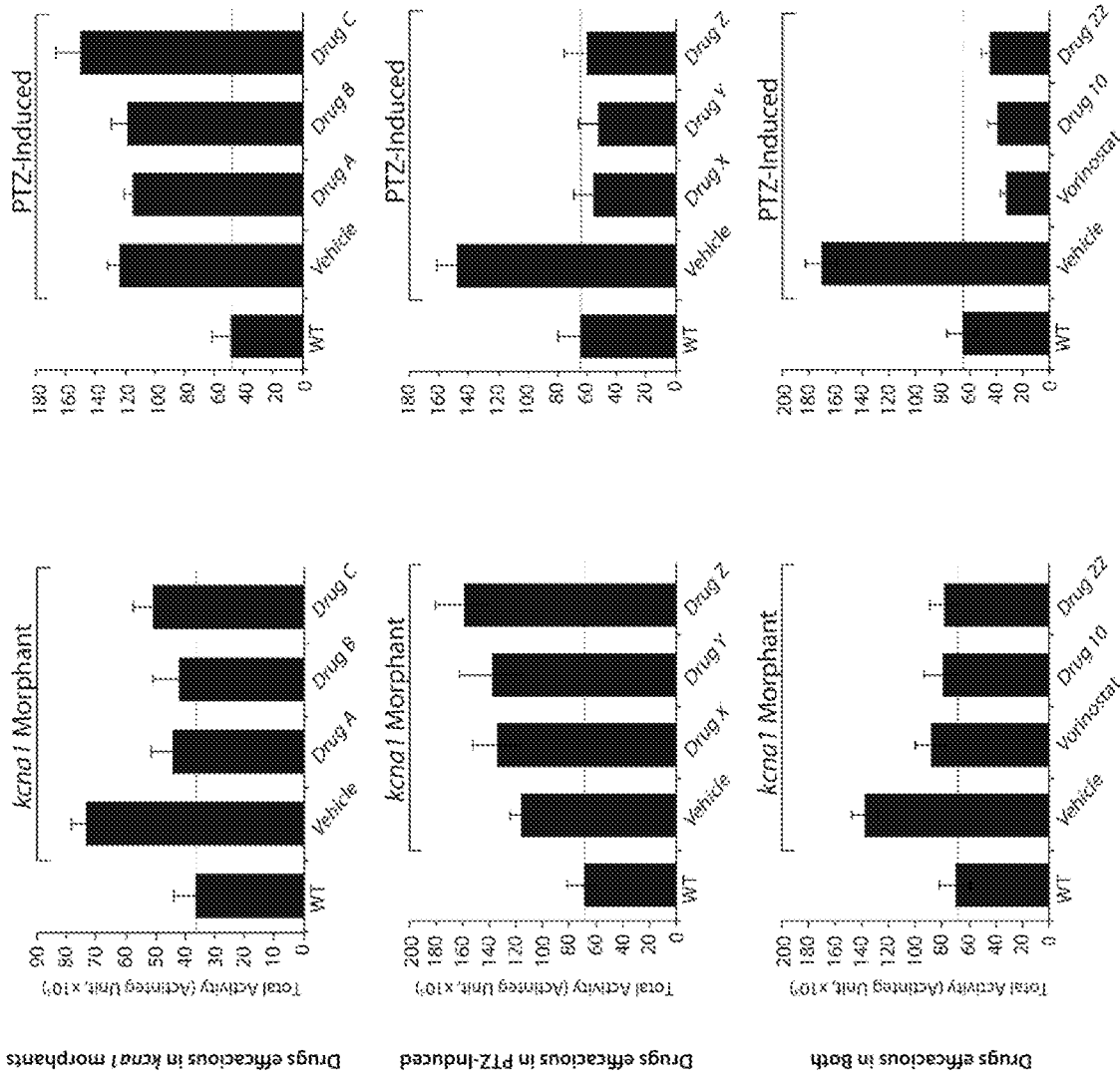
FIG. 6A. Compounds that block hyperactive phenotype in kcna1 morpholino-treated zebrafish (left) but not PTZ-induced hyperactivity model (right).
FIG. 6B. Compounds that selective block hyperactivity in PTZ-treated larvae (right) but not kcna1 morphants (left).
FIG. 6C. Compounds block hyperactivity in both kcna1 morphants (left) and PTZ-induced zebrafish (right).

FIG. 5 shows the bioenergetics profiles of compounds uncovered during the drug screening in kcna1 morphant zebrafish. As shown in FIG. 5, basal respiration was elevated in kcna1 morphants (second bar, left graph) due to increased mitochondrial respiration (second bar, right graph) and without contribution for non-mitochondrial respiration (second bar, middle graph). Increased respiration was blocked by Valproic Acid (VPA) and four representative candidate compounds (#90, #5, #44, #53) via mitochondrial-mediated events. In addition, compounds #44 and #53 blocked increased respiration in both kcna1 morphants (left graph) and PTZ-treated larvae (data not shown) and here were the only compounds to decrease both non-mitochondrial—(the primary bioenergetics pathway of PTZ-treated embryos; noted by asterisk-arrow) and mitochondrial-mediated respiration. FIG. 6 shows representative data from pilot drug screening. FIG. 6A. Compounds that block hyperactive phenotype in kcna1 morphant-treated zebrafish (left) but not PTZ-induced hyperactivity model (right). FIG. 6B. Compounds that selective block hyperactivity in PTZ-treated larvae (right) but not kcna1 morphants (left). FIG. 6C. Some compounds are efficacious in both kcna1 morphants (left) and PTZ-treated larvae (right).

Figure 7A:
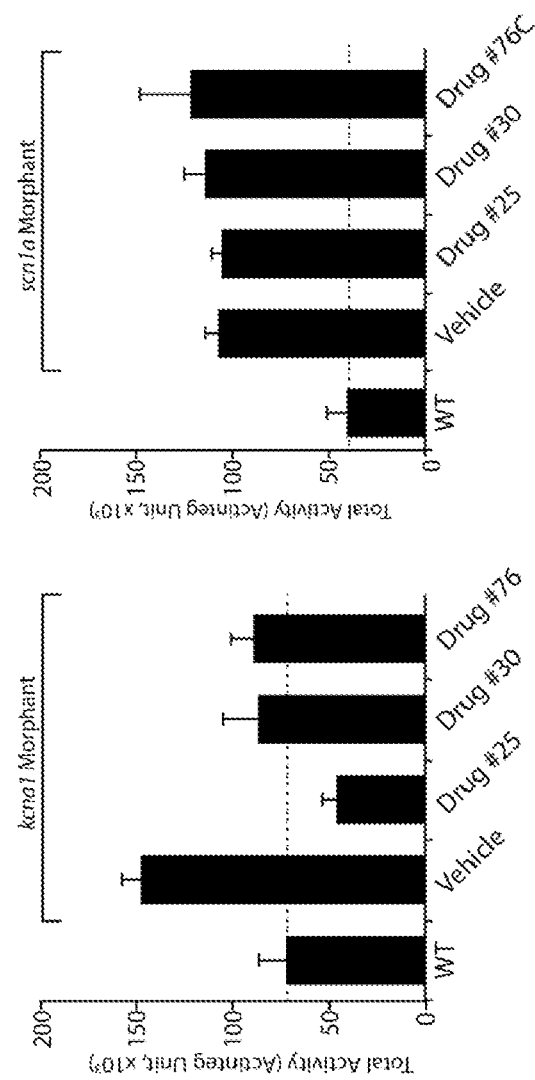
FIG. 7A. Some drugs are efficacious in kcna1 morphants but not scn1a morphants.
Figure 7B:
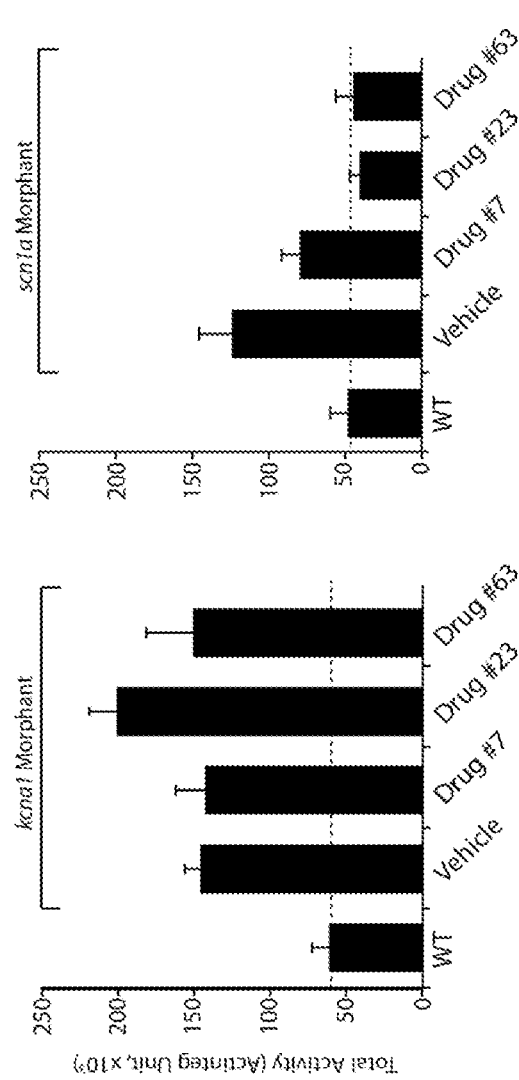
FIG. 7B. Some drugs are efficacious in scn1a morphants and not kcna1 morphants.

FIG. 7 shows that some drugs are efficacious in (A) kcna1 morphants but not scn1a morphants or (B) scn1a morphants and not kcna1 morphants.

In conclusion, this Example demonstrates that the zebrafish-based drug screening assays disclosed herein can rapidly and effectively identify candidate drug compounds capable of altering mitochondrial energetics in zebrafish engineered to model human disease.

Example 4

Validation of Candidate Drugs

Positive hits identified in Example 3 were further verified.

First, EEG recordings on live zebrafish were conducted. Briefly, acute seizure-like activity is measured in WT and mutant zebrafish larvae (5 dpf). Extracellular field recordings were obtained from the optic tectum of zebrafish larvae exposed first to vehicle, then washed out and then exposed to candidate drugs. Recordings are collected over 20 minutes and any decrease in small-amplitude "interictal"-like activity and/or large-amplitude "ictal"-like activity is quantified.

Second, candidate drugs that decrease interictal-and/or ictal-like activity in mutant zebrafish lines are then validated in rodent models. Two rodent lines that contain coding deletions in the mammalian orthologs to the zebrafish mutants were used. Candidate drugs were injected intracranially and a decrease in seizure behaviors are monitored using video and hippocampal slice EEG.

Figures 8A, 8B:
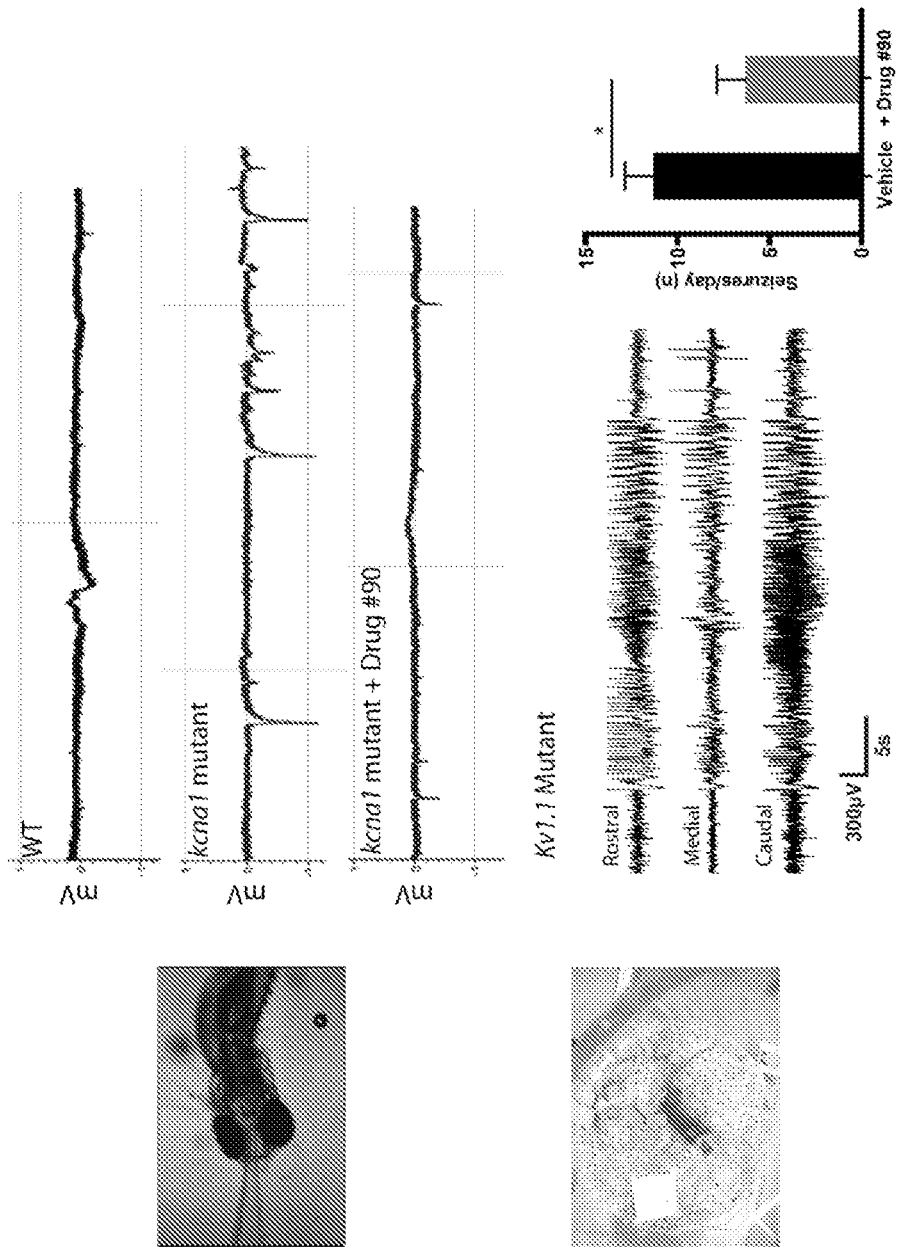
FIG. 8A. left: representative image showing electrode insertion. Right: representative EEG traces of wildtype (WT), kcna1 mutants, and kcna1 mutants plus vorinostat (10 µM).
FIG. 8B Vorinostat (Drug #90) treatment reduces seizure occurrence in Kv1.1 null mice. Three sets of epidural electroencephalogram (EEG) electrodes simultaneously recorded the signals across the rostral (top trace), medial (middle), and caudal (bottom trace) dorsal aspect of the neocortex. Bar graph (right) of the mean number of seizures per day recorded from Kv1.1−/−mice+/−vorinostat.

Briefly, mice were anesthetized with 3% isofluorane for 2 minutes. Eye glue was applied to the mouse, and anesthesia increased to 2% isofluorane. A "toe pinch" was administered to check anesthetic effect. The surgical area was then shaved while still connected to anesthesia. The anesthesia was increased to 2.5% isofluorane and the anesthetic cone placed over the nose. Using a scalpel, a 1.5 cm rostral-caudal incision was made to expose skull surface. Using the tip of fresh 23 mm gauge needle, 3 holes were drilled on each side of the mouse skull while avoiding suture lines. A 0.1 inch mouse screw with wire leads was inserted midway using an EEG screwdriver. Dental acrylic was to secure the wires on the 6-pin surface mount connector and allowed to harden for 20 minutes. A small pocket in the neck muscles of mouse was made by blunt dissection and 2 EMG (electromyogram) electrodes were affixed. Wrap wires together, and clip the extra length off the ends. Cover All exposed wires were covered with a final layer of dental acrylic avoiding the sockets. The anesthesia was then turned off, the stereotaxic bar removed, and the mouse returned to its cage. The acrylic was allowed to harden for 12-24 hours before attaching the pin connector to the video EEG monitor. Recordings were made for 3 consecutive days to establish baseline number of seizures per day. On day 3, drug was administered (either IP or oral gavage) either once/day or twice/day, depending on dosing regimen that is known for the drug. Repeat for the next 3 days. At the end of the dosing period, recordings for another 3 days were made without drug treatment to see if absence of drug causes seizures to return. FIG. 8 demonstrates validation of vorinostat, a drug that was uncovered from the screen. As shown in FIG. 8A, vorinostat blocks seizure-like activity in kcna1 mutant zebrafish.

FIG. 8B shows data for Kv1.1 rodent model (which is the ortholog to kcna1). Vorinostat (Drug #90) treatment reduces seizure occurrence in Kv1.1 null mice. Shown is a representative example of an electrographic seizure recorded from a Kv1.1−/−mouse. Three sets of epidural electroencephalogram (EEG) electrodes simultaneously recorded the signals across the rostral (top trace), medial (middle), and caudal (bottom trace) dorsal aspect of the neocortex. Bar graph of the mean number of seizures per day recorded from three Kv1.1−/−mice. Mice were recorded 24 hours per day for 3 consecutive days (No treatment, PND 43-45) and then received vorinostat injections (20 mg/kg, twice a day) for the next three consecutive days (PND 46-48). Vorinostat treatment significantly reduced the number of seizures (Two-way ANOVA, F=27.7, p<0.01).

Since rodent video EEG is highly persuasive evidence with respect to demonstrating anticonvulsant activity of novel drugs, from these data we conclude that vorinostat is a potential candidate to decrease seizure activity in humans.

Example 5

Figure 9B:
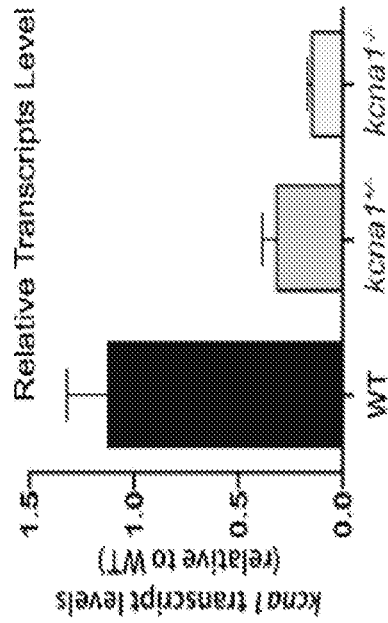
FIG. 9B. Relative kcna1 transcript levels in WT, heterozygous, and mutant zebrafish.
Figure 9A:
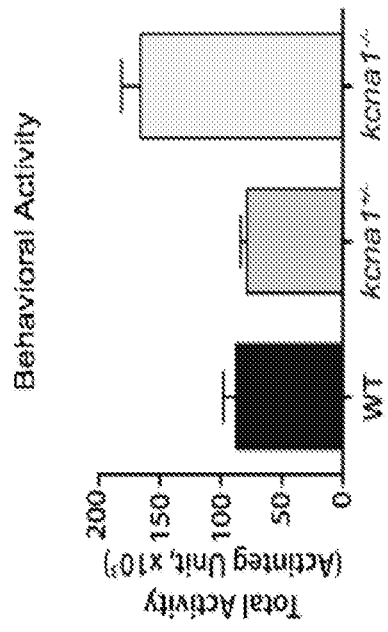
FIG. 9A. Total behavioral activity in WT, heterozygous, and mutant zebrafish.

Validation of Drugs Identified in Zebrafish Morphants in Corresponding Mutant Fish This example confirms that the results of drug screens using zebrafish morphants are the same in zebrafish bearing corresponding germline mutations. kcna1$^{+/-}$ zebrafish were generated as described in Example 1. Heterozygous kcna1$^{+/-}$ F1s were incrossed and the offspring examined in a behavioral monitoring chamber (Zebralab). We assume ¾ of the progeny are WT or heterozygotes and ¼ are mutants. FIG. 9A shows behavioral activity of WT, presumed heterozygotes, and presumed mutant larvae at 5 dpf. To confirm their genotype, we conducted qPCR. FIG. 9B shows that heterozygotic zebrafish have approximately 50% transcript levels of WT and the mutants have very low transcript levels. From these data, we can conclude that kcna1 morphants and kiwi genetic mutants display similar behavioral phenotypes.

Figure 9D:
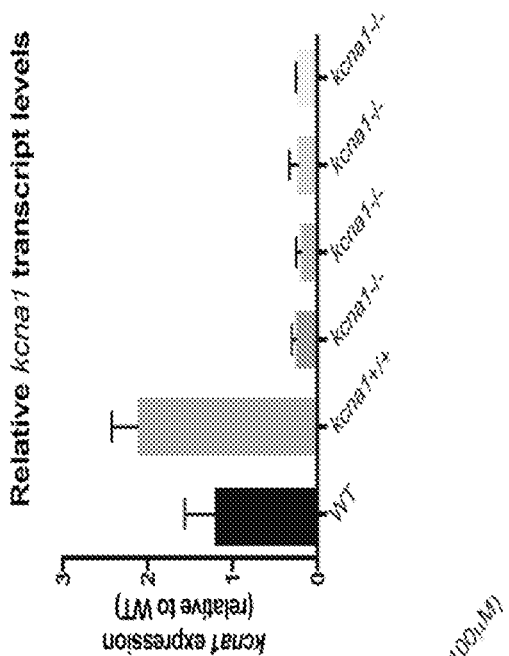
FIG. 9D. Relative kcna1 transcript levels in zebrafish used for experiment depicted in FIG. 9C.
Figure 9C:
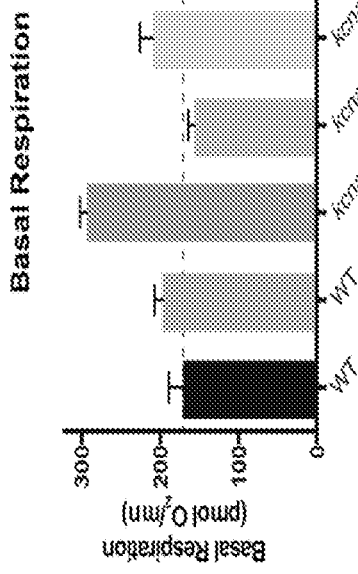
FIG. 9C. Mitochondrial function in WT, heterozygous, and mutant zebrafish as well as mutant fish exposed to VPA, vorinostat, and drug X.

Next, a similar experiment was conducted to confirm that kcna1 mutants display a similar phenotype for mitochondrial function (e.g., increased mitochondrial function). Larvae were seeded into 24-well plates and assayed in the Seahorse machine for altered bioenergetics as discussed above. FIG. 9C shows WT basal respiration levels and that a presumed WT or heterozygous larvae has similar basal respiration levels. Increased basal respiration levels in approximately 25% of the embryos were also detected, as would be expected for a homozygous recessive mutation. Larvae that displayed increased basal respiration were washed with PBS and treated with compounds shown to block basal respiration in our kcna1 morphants, specifically the anti-convulsant VPA and two drugs uncovered in our screen (vorinostat and Drug X as shown above). As shown in FIG. 9C, these drugs decreased basal respiration in mutant larvae. Genotype was subsequently confirmed by qPCR (FIG. 9D).

Combined, we conclude based on the data shown in this Example that kcna1 genetic mutants behave in the same manner as kcna1 morphants with respect to the results of the drug screening assay.

Example 6

Sensitivity of Zebrafish Drug Discovery Platform

This example demonstrates the accuracy of the zebrafish-based drug discovery platform described herein. Twenty one (21) FDA-approved anti-convulsant drugs were obtained in order to verify the strength and sensitivity of the assay (there are approximately 25 FDA drugs currently approved and on the market for epilepsy). All 21 compounds were run against three zebrafish "epilepsy" models: PTZ-induced, kcna1 morphants, and scn1a morphants (see Example 3, above).

10 mM stock solutions of drugs in DMSO were stored at −80° C. and on the day of assay were diluted in E3 medium to a final concentration of 20 μM. For behavioral assays and Seahorse bioenergetics, 20 μM final concentration was used. Adult wild-type TL zebrafish were raised at the Kurrasch Aquatic Research Laboratory at the University of Calgary under standard conditions (28° C., 14 h light/10 h dark cycle) on a recirculating water system.

Embryos were obtained by natural spawning from mating pairs, screened for viability and for kcna1 and scn1a morpholino models, embryos were injected with either the kcna1- or scn1a-targeting morpholino at the one cell stage. The embryos were sorted for uptake of the morpholino four hours post-injection and seeded to 96 well plates, wrapped in aluminum foil (i.e., raised in the dark), maintained in a non-$CO_2$ incubator at 28.5° C. until 5 dpf.

For the PTZ model, embryos were collected by natural spawning from breeding pairs, sorted for viability, seeded to 96-well plates and maintained in a non-$CO_2$ incubator at 28.5° C. until 5 dpf under standard 14 h light/10 h dark cycle.

On the day of assay, for the kcna1 and scn1a morpholino models, fish were habituated for 20 minutes under 100% light treated with 20 μm of drugs for 20 minutes, and then assayed for locomotor activity in dark for 20 minutes in the zebrabox (Viewpoint Lifesciences, Lyon, Fr). Larval locomotor activity was analyzed using Zebralab V3 software (Viewpoint Lifesciences, Lyon, Fr). For the PTZ model, at 5 dpf, fish were treated with 10 mM PTZ for 10 minutes and then with 20 μM of drugs for 20 minutes under ambient light, and then assayed for locomotor activity under 100% light for 20 minutes in the zebrabox (Viewpoint Lifesciences, Lyon, Fr). Larval locomotor activity was analyzed using Zebralab V3 software (Viewpoint Lifesciences, Lyon, France).

Figure 10:
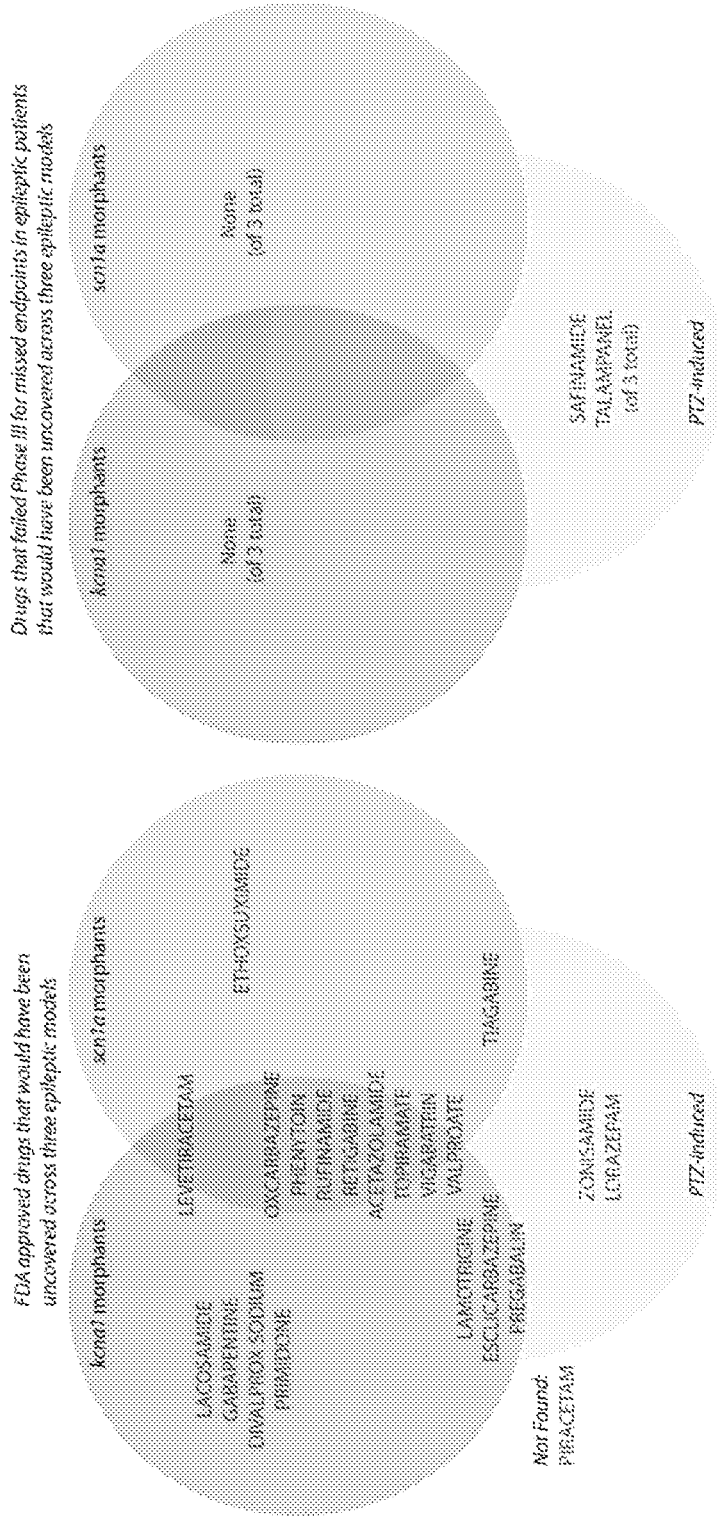
FIG. 10 is a venn diagram showing the results of a screen of 21 FDA-approved anti-convulsant drugs (left) as well as a screen of drugs that failed phase III trials for missing clinical endpoints in epileptic patients (right) using three models of epileptic zebrafish.

For the Seahorse bioenergetics measurements, microinjected kcna1 or scn1a morphants or WT zebrafish were maintained in 96 well plates as previously described. XF24 extracellular flux assay plates (Seahorse Bioscience; Massachusetts), were hydrated overnight with XF Calibrant (pH 7.4). On the day of assay, 2-day old zebrafish morphants were seeded to XF24 islet capture microplates, and treated with 20 μM of drugs and allowed to habituate for 30 minutes in a non-$CO_2$ incubator at 28.5° C. All XF assays were performed using XF-24 Extracellular Flux Analyzer (Seahorse Bioscience). For PTZ screen, 2-day old WT zebrafish were seeded to XF islet capture microplates, treated with 10 mM PTZ for 10 minutes and then treated with 20 μM drugs before habituating for 30 minutes in a non-$CO_2$ incubator at 28.5° C. Only drugs that were successful in the locomotor screen were used for the Seahorse bioenergetics screen As depicted in FIG. 10 (left), 20/21 drugs would have been uncovered as significantly affecting mitochondrial function (95% confidence rate) using the drug-discovery platform described herein. In fact, nearly 40% (8/21) would have been uncovered in all three models.

A further screen of drugs that were not successful in clinical trials in epileptic patients was also conducted. We searched the literature for reports of Phase III clinical trials for novel anti-convulsant drugs that failed for missed endpoints. We were able to purchase three compounds: Safinamide, Talampanel, and Remacemide. We conducted a blinded study whereby these three "failed drugs"+three FDA approved drugs were blinded and assayed in the screening platform. As predicted, we would have uncovered all three FDA approved drugs as we showed previously. As shown in FIG. 10 (right), we would not have uncovered any of the "failed drugs" in our genetic models and would have uncovered two of the three drugs in the PTZ-induced model. This is as expected since the PTZ-induced model is a commonly used approach in large chemical screens in pharmaceutical companies.

From this experiment, we conclude that the methods for high throughput drug screening using zebrafish models of human disease disclosed herein are not only powerful but surprisingly sensitive and accurate.

Example 7

Morpholino-Treated Zebrafish Modeling a Variety of Human Disease Display Dysregulation of Mitochondrial Bioenergetics This Example demonstrates that (a) genetic models for a variety of disease categories can be created using zebrafish for use in the disclosed drug screening methods and (b) that these zebrafish display dysregulation of bioenergetics which in some instances can be reversed by a FDA approved drug for that disease.

Morpholinos directed to scn1a (epilepsy), park2 (neurodegenerative disease), idh1 (brain tumors (astrocytoma/oligodendrogliomas), cdkn2b (oligodendroglioma), h3f3a (oligodendroglioma), snf5 (smarcb1a in zebrafish; Atypical Teratoid/Rhabdoid)), and shank3 (Autism Spectrum Disorder) were created and zebrafish larvae exposed as detailed in Example 3. Morpholino sequences and concentrations employed to induce gene expression changes are shown in Table 6.

TABLE 6

Sequences for morpholinos used in Examples

| Gene | Sequence | Concentration (nM) |
| --- | --- | --- |
| Kcna1 | GTTGTCCCCAGCCACAACTGTCATC (SEQ ID NO: 1) | 5 |
| Scn1a | CGCCATTTTCTCATCCTGAA (SEQ ID NO: 2) | 4 |
| Park2 | TGATTTGGTTCTCTTACCCCACAGC (SEQ ID NO: 3) | 5 |
| Cdkn2b | TAAAGCGCGTCTAAACCTACCTGTA (SEQ ID NO: 4) | 5 |
| Idh1 | CATGTTCATACAACCTCCAAACCGC (SEQ ID NO: 5) | 5 |
| H3f3a | ACAATATAATCTCACCTGAAGAGCG (SEQ ID NO: 6) | 5 |
| Smarcb1a | TAATTCAACACTTACCGTGAGAGGA (SEQ ID NO: 7) | 5 |
| Shank3 | TTACAAACCCTCGTCTTACCTTAGT (SEQ ID NO: 8) | 5 |

Figure 11A:
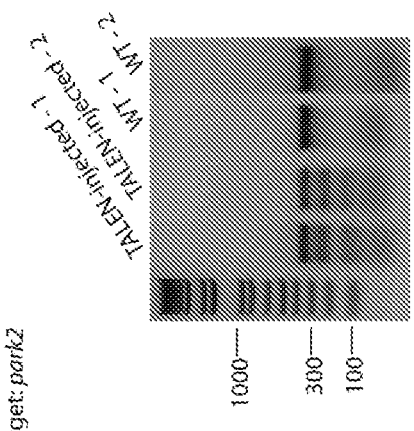
FIG. 11A depicts the results of an exemplary T7/E1 mismatch detection assay used to screen embryos injected with scn1a-targeting TALEN constructs.
Figure 11B:
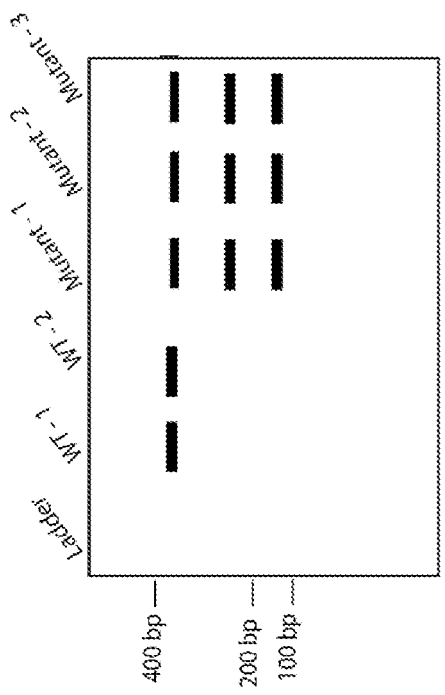
FIG. 11B. Basal respiration measured in scn1a morphants and following exposure Valproate as well as other novel drugs identified in screening assays.

FIG. 11A depicts an example of the results of a T7/E1 mismatch detection assay used to screen embryos injected with scn1a-targeting TALEN constructs. Of 200 embryos injected, 20 embryos are collected, sacrificed, and analyzed via T7/E1 mismatch assay to determine efficacy of the TALEN construct. The presence of two additional bands in the injected embryos suggests a mismatch across the targeted locus in one allele, and serves as an indicator of likely indels. We assess the percentage of 20 embryos that display a mismatch and only TALEN constructs that illustrate >70% efficiency are kept. If the T7/E1 assay predicts poor efficiency, all injected embryos are discarded and a new TALEN construct is created. FIG. 11B shows basal respiration measured in scn1a morphants which is reversed after exposure to an FDA-approved drug (Valproate) as well as novel drug identified from our screen (see above). scn1a-MO zebrafish display increased bioenergetics relative to control whereas Valproate plus two new drugs (Drug X and Drug Y) reduce basal respiration to WT levels.

Figure 11C:
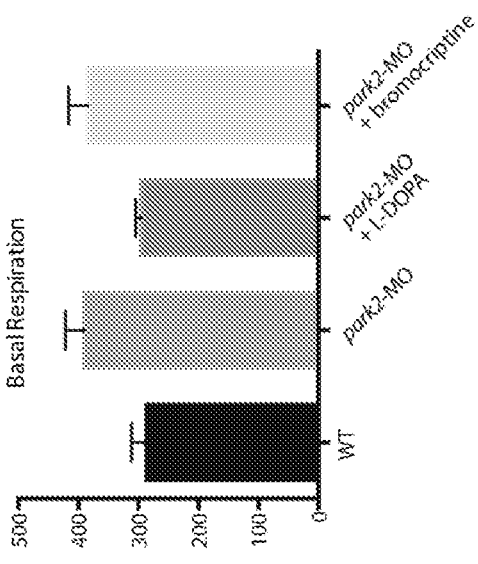
FIG. 11C. Depiction of a T7/E1 mismatch detection assay showing indels across the target locus in park2-TALEN injected embryos.
Figure 11D:
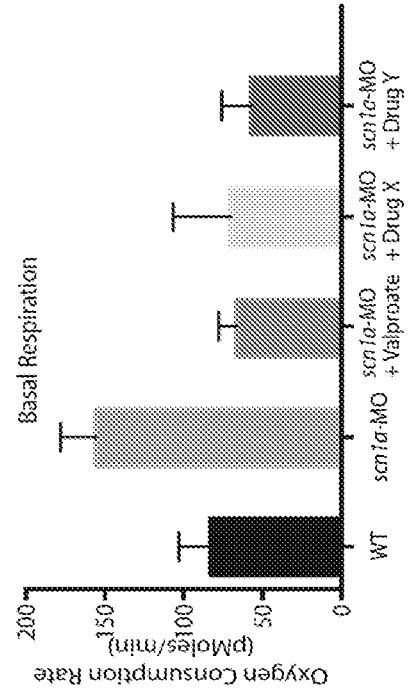
FIG. 11D. Basal respiration in park2 morphants compared to wild type as well as in park2-MO treated with L-DOPA and bromocriptine.

FIG. 11C depicts a T7/E1 mismatch detection assay showing indels across the target locus in park2-TALEN injected embryos. The WT band is 352 by and the cut bands are 225 bp+127 bp. The presence of the WT band in the injected embryos suggests a heterozygous phenotype, as would be expected. From these data, we conclude that our TALEN construct is efficacious and that we are very likely to generate a germline genetic mutant in the F1 generation. FIG. 11D shows basal respiration is increased in park2 morphants compared to WT controls. The addition of the anti-Parkinson's drug L-DOPA reverses this increased bioenergetics to WT levels, while bromocriptine had no effect. Based on this data, we conclude that bioenergetics is dysregulated in this model for Parkinson's Disease and that we can uncover efficacious therapeutics by screening for drugs that restore mitochondrial homeostasis.

Figure 11G:
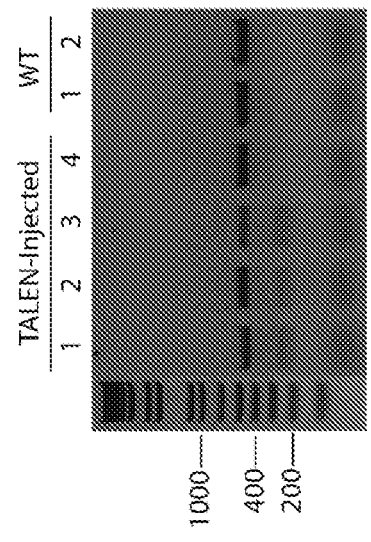
FIG. 11G. Depiction of a T7/E1 mismatch detection assay showing indels across the target locus in h3f3a-TALEN injected embryos.
Figure 11H:
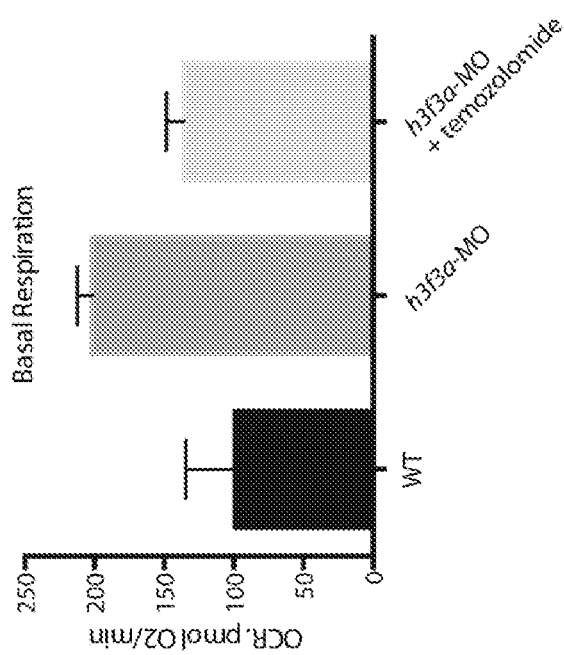
FIG. 11H. Basal respiration in h3f3a morphants compared to wild type as well as in h3f3a-MO treated with temozolomide.
Figure 11E:
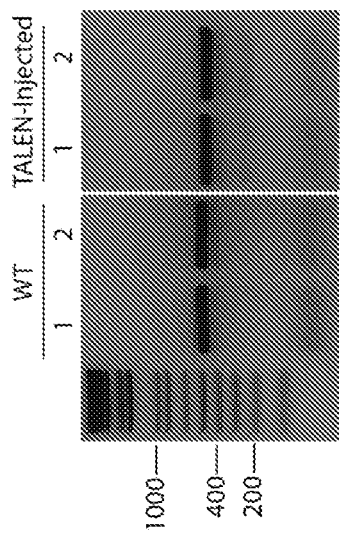
FIG. 11E. Depiction of a T7/E1 mismatch detection assay showing indels across the target locus in cdkn2b-TALEN injected embryos.
Figure 11F:
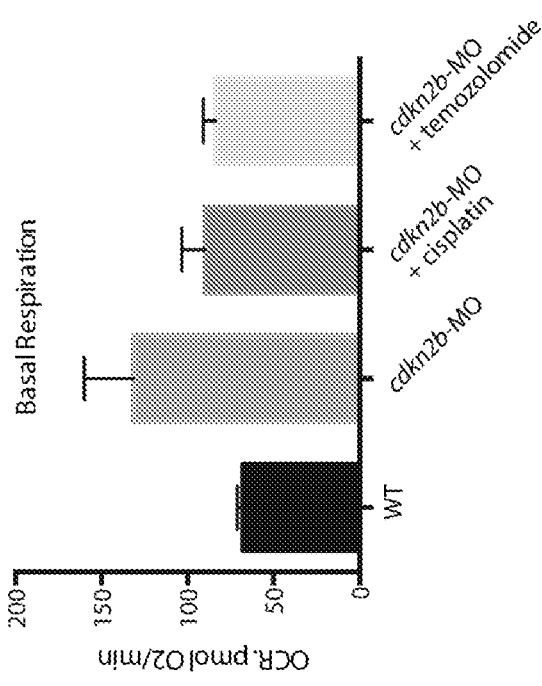
FIG. 11F. Basal respiration in cdkn2b morphants compared to wild type as well as in cdkn2b-MO treated with cisplatin and temozolomide.

FIG. 11E depicts a T7/E1 mismatch detection assay showing indels across the target locus in cdkn2b-TALEN injected embryos. The WT band is 476 by and the cut bands are 223 bp+257 bp. We detect a faint band in all four samples (arrow denotes most pronounced band). The presence of the WT band in the injected embryos suggests a heterozygous phenotype, as would be expected. From these data, we conclude that our TALEN construct is efficacious and that we are very likely to generate a germline genetic mutant in the F1 generation. FIG. 11F shows basal respiration is increased in cdkn2b morphants compared to WT controls. The addition of the glioblastoma drugs cisplatin and temozolomide reverses this increased bioenergetics to WT levels. We conclude that bioenergetics is dysregulated in this model for glioblastoma and that we can uncover efficacious therapeutics by screening for drugs that restore mitochondrial homeostasis.

FIG. 11G depicts a T7/E1 mismatch detection assay showing indels across the target locus in h3f3a-TALEN injected embryos. The WT band is 431 by and the cut bands are 231 bp+200 bp. The presence of the WT band in the injected embryos suggests a heterozygous phenotype, as would be expected. From these data, we conclude that our TALEN construct is efficacious and that we are very likely to generate a germline genetic mutant in the F1 generation. FIG. 11H shows basal respiration is increased in h3f3a morphants compared to WT controls. The addition of the glioblastoma drug temozolomide reverses this increased bioenergetics to WT levels. We conclude that bioenergetics is dysregulated in this model for glioblastoma and that we can uncover efficacious therapeutics by screening for drugs that restore mitochondrial homeostasis.

Figure 11I:
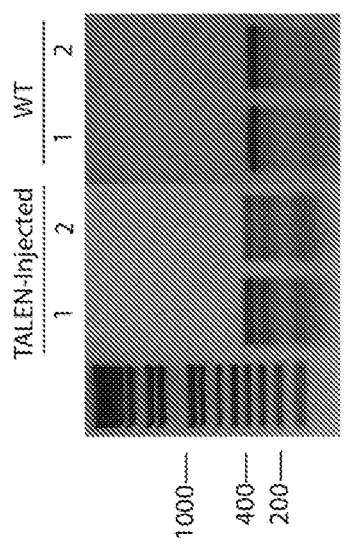
FIG. 11I. Depiction of a T7/E1 mismatch detection assay showing indels across the target locus in smarcbla-TALEN injected embryos.
Figure 11J:
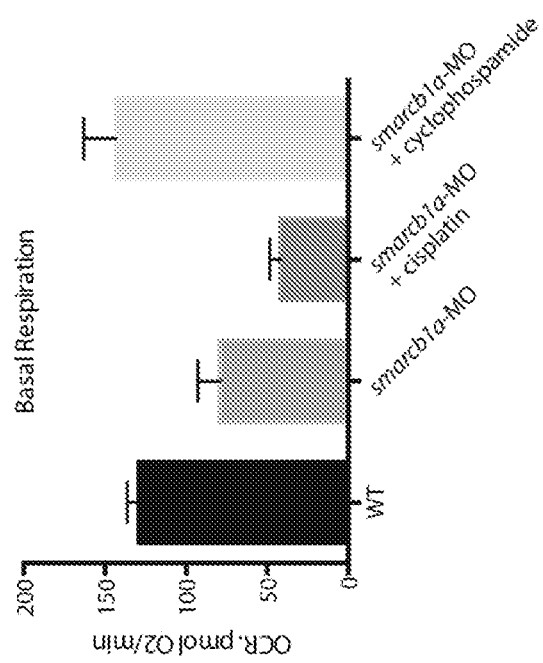
FIG. 11J. Basal respiration in smarcbla morphants compared to wild type as well as in smarcbla-MO treated with cisplatin and cyclophosphamide.

FIG. 11I depicts a T7/E1 mismatch detection assay showing indels across the target locus in smarcb1a-TALEN injected embryos. The WT band is 374 by and the cut bands are 214 bp+160 bp. The presence of the WT band in the injected embryos suggests a heterozygous phenotype, as would be expected. From these data, we conclude that our TALEN construct is efficacious and that we are very likely to generate a germline genetic mutant in the F1 generation. FIG. 11J shows basal respiration is increased in smarcb1a morphants compared to WT controls. The addition of the cancer drug cisplatin reverses this increased bioenergetics to WT levels, whereas cyclophosphamide had no effect. We conclude that bioenergetics is dysregulated in this model for AT/RT and we can uncover efficacious therapeutics by screening for drugs that restore mitochondrial homeostasis.

Figure 12A:
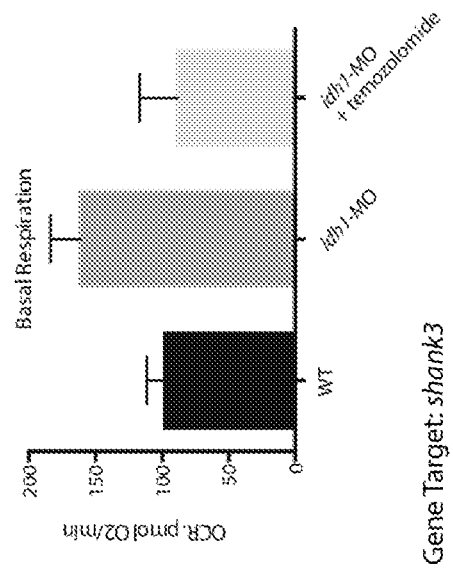
FIG. 12A. Basal respiration in idh1 morphants compared to wild type as well as in idh1-MO treated with temozolomide.
Figure 12B:
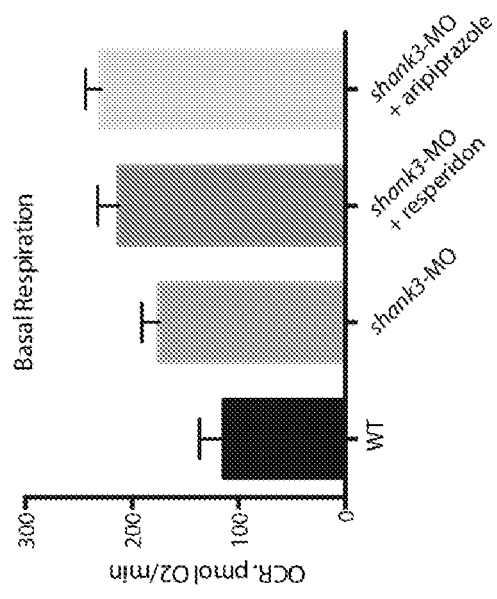
FIG. 12B. Basal respiration in shank3 morphants compared to wild type as well as in shank3-MO treated with resperidon and aripiprazole.

FIG. 12A shows that basal respiration is increased in idh1 morphants compared to WT controls. The addition of the glioma drug temozolomide reverses this increased bioenergetics to WT levels leading to the conclusion that bioenergetics is dysregulated in this model for glioma and that we can uncover efficacious therapeutics by screening for drugs that restore mitochondrial homeostasis. FIG. 12B shows that basal respiration is increased in shank3 morphants compared to WT controls. There are no FDA-approved drugs that treat the core symptoms of autism spectrum disorders. Instead, we selected drugs used to treat schizophrenia. Neither resperidon nor aripiprazole were effective in reducing basal respiration in our shank3-morphants. We conclude that bioenergetics is dysregulated in this model for ASD and schizophrenia and we predict we can uncover efficacious therapeutics by screening for drugs that restore mitochondrial homeostasis.

In conclusion, this Example demonstrates that mitochondrial bioenergetics is dysregulated in several human diseases which can be successfully recapitulated in zebrafish via genetic manipulation for use in the drug-screening methods disclosed herein.

We claim:

1. A method of identifying a compound as a candidate compound for modulating mitochondrial function in the human brain, comprising:
   a) contacting a compound with a teleost exhibiting decreased expression of a teleost gene that results in altered mitochondrial function, wherein the teleost is selected from the group consisting of: a morphant teleost comprising a morpholino that decreases expression of the teleost gene, and a knockout teleost comprising a knockout of the teleost gene; and
   b) assaying for mitochondrial function in the contacted morphant or knockout teleost,
   wherein restoration of normal mitochondrial function in the contacted morphant or knockout teleost compared to a control morphant or knockout teleost not contacted with the compound is indicative that the compound is a candidate compound for modulating mitochondrial function in the human brain.

2. The method of claim 1, wherein the teleost is a zebrafish embryo, a zebrafish larva or a zebrafish adult.

3. The method of claim 1, wherein said contacting comprises homogeneously distributing the compound in media containing the teleost or injecting said compound into the teleost.

4. The method of claim 1, wherein the compound is selected from the group consisting: of a small molecule, a nucleic acid, a peptide, a protein, a carbohydrate, and a lipid.

5. The method of claim 1, wherein the mitochondrial function is assayed by measuring one of more mitochondria outputs selected from the group consisting of ATP level, a level of an ATP metabolite, mitochondria respiration rate, reactive oxygenated species, reactive nitrogen species, mitochondrial uncoupling protein, mitochondrial permeability transition threshold, mitochondrial calcium homeostasis, mitochondrial appearance change, transcriptional changes in mitochondrial teleost genes, and mitochondrial membrane potential.

6. The method of claim 1, wherein the teleost exhibits neuronal hyperactivity or loss of neuronal function.

7. The method of claim 1, wherein the teleost gene is selected from the group consisting of: scn1a, kcna1, idh1, smarcb1a, and shank3.

8. The method of claim 1, wherein the teleost gene is scn1a.

9. The method of claim 1, wherein the teleost gene is kcna1.

* * * * *

```
                           SEQUENCE LISTING

<160> NUMBER OF SEQ ID NOS: 11

<210> SEQ ID NO 1
    <211> LENGTH: 25
    <212> TYPE: DNA
    <213> ORGANISM: Artificial sequence
    <220> FEATURE:
    <223> OTHER INFORMATION: synthetic sequence

<400> SEQUENCE: 1
gttgtcccca gccacaactg tcatc                                              25

<210> SEQ ID NO 2
    <211> LENGTH: 20
    <212> TYPE: DNA
    <213> ORGANISM: Artificial sequence
    <220> FEATURE:
    <223> OTHER INFORMATION: synthetic sequence

<400> SEQUENCE: 2
cgccattttc tcatcctgaa                                                    20

<210> SEQ ID NO 3
    <211> LENGTH: 25
    <212> TYPE: DNA
    <213> ORGANISM: Artificial sequence
    <220> FEATURE:
    <223> OTHER INFORMATION: synthetic sequence

<400> SEQUENCE: 3
tgatttggtt ctcttacccc acagc                                              25

<210> SEQ ID NO 4
    <211> LENGTH: 25
    <212> TYPE: DNA
    <213> ORGANISM: Artificial sequence
    <220> FEATURE:
    <223> OTHER INFORMATION: synthetic sequence

<400> SEQUENCE: 4
taaagcgcgt ctaaacctac ctgta                                              25

<210> SEQ ID NO 5
    <211> LENGTH: 25
    <212> TYPE: DNA
    <213> ORGANISM: Artificial sequence
    <220> FEATURE:
    <223> OTHER INFORMATION: synthetic sequence

<400> SEQUENCE: 5
catgttcata caacctccaa accgc                                              25
```

```
<210> SEQ ID NO 6
<211> LENGTH: 25
<212> TYPE: DNA
<213> ORGANISM: Artificial sequence
<220> FEATURE:
<223> OTHER INFORMATION: synthetic sequence

<400> SEQUENCE: 6
acaatataat ctcacctgaa gagcg                                              25

<210> SEQ ID NO 7
<211> LENGTH: 25
<212> TYPE: DNA
<213> ORGANISM: Artificial sequence
<220> FEATURE:
<223> OTHER INFORMATION: synthetic sequence

<400> SEQUENCE: 7
taattcaaca cttaccgtga gagga                                              25

<210> SEQ ID NO 8
<211> LENGTH: 25
<212> TYPE: DNA
<213> ORGANISM: Artificial sequence
<220> FEATURE:
<223> OTHER INFORMATION: synthetic sequence

<400> SEQUENCE: 8
ttacaaaccc tcgtcttacc ttagt                                              25

<210> SEQ ID NO 9
<211> LENGTH: 29
<212> TYPE: DNA
<213> ORGANISM: Artificial sequence
<220> FEATURE:
<223> OTHER INFORMATION: synthetic sequence

<400> SEQUENCE: 9
gcgttatgga tgtgacattt atggaccgc                                          29

<210> SEQ ID NO 10
<211> LENGTH: 27
<212> TYPE: DNA
<213> ORGANISM: Artificial sequence
<220> FEATURE:
<223> OTHER INFORMATION: synthetic sequence

<400> SEQUENCE: 10
gcgttatgga tgtgacatat tgacggc                                            27

<210> SEQ ID NO 11
<211> LENGTH: 20
<212> TYPE: DNA
<213> ORGANISM: Artificial sequence
<220> FEATURE:
<223> OTHER INFORMATION: synthetic sequence

<400> SEQUENCE: 11
gcgttatgga cgattgacgc                                                    20
```